United States Patent
Uchida et al.

(10) Patent No.: US 6,624,162 B2
(45) Date of Patent: Sep. 23, 2003

(54) IMIDAZOPYRIDINE COMPOUNDS AS 5-HT4 RECEPTOR MODULATORS

(75) Inventors: Chikara Uchida, Aichi-ken (JP); Hirohide Noguchi, Aichi-ken (JP); Alan Stobie, Sandwich (GB); Geoffrey Gymer, Sandwich (GB); David Fenwick, Sandwich (GB)

(73) Assignee: Pfizer Inc., New Yok, NY (US)

( * ) Notice: Subject to any disclaimer, the term of this patent is extended or adjusted under 35 U.S.C. 154(b) by 0 days.

(21) Appl. No.: 10/251,109

(22) Filed: Sep. 20, 2002

(65) Prior Publication Data

US 2003/0092699 A1 May 15, 2003

Related U.S. Application Data

(60) Provisional application No. 60/343,371, filed on Oct. 22, 2001.

(51) Int. Cl.[7] .................. A61K 31/437; A61K 31/5377; C07D 471/04

(52) U.S. Cl. .................... 514/233.2; 514/300; 544/127; 546/121

(58) Field of Search ......................... 544/127; 546/121; 514/233.2

(56) References Cited

U.S. PATENT DOCUMENTS

| | | |
|---|---|---|
| 5,137,893 A | 8/1992 | Becker et al. |
| 5,219,850 A | 6/1993 | Becker et al. |
| 5,434,161 A | 7/1995 | Becker et al. |
| 5,591,749 A | 1/1997 | Becker et al. |
| 5,604,239 A | 2/1997 | Becker et al. |
| 5,968,965 A | 10/1999 | Dinsmore et al. |

FOREIGN PATENT DOCUMENTS

| | | |
|---|---|---|
| EP | 0504679 | 9/1992 |
| EP | 0274867 | 4/1994 |
| EP | 1217000 | 6/2002 |
| JP | Hei 1-258674 | 10/1989 |
| JP | 2001-6877 | 1/2001 |
| WO | WO 9215593 | 9/1992 |
| WO | WO 9408998 | 4/1994 |
| WO | WO 9605166 | 2/1996 |
| WO | WO 9727852 | 8/1997 |
| WO | WO 9738665 | 10/1997 |
| WO | WO 9950247 | 10/1999 |
| WO | WO 9950264 | 10/1999 |
| WO | WO 0105763 | 1/2001 |
| WO | WO 0114331 | 3/2001 |

OTHER PUBLICATIONS

Dumuis, et al. "A 5HT Receptor in the Central Nervous System, Positively Coupled with Adnylate Cyclase, is Antagonized by ICS 205 930", *Eur. Journ. of Pharmacology* 146, pp 187–188, (1988).

Dumuis, et al. "The Gastrointestinal Prokinetic Benzamide Derivatives are Agonists at the Non–Classical 5–HT Receptor (5–HT4) Positively Coupled to Adenylate Cyclase in Neurons", *Naunyn–Schmiedeberg's Archives of Pharmacology* 340, pp. 403–410, (1989).
Bockaert, et al. "The 5–HT4 Receptor: A Place in the Sun" *TiPs Reviews* 13 pp. 141–145, (1992).
Ford, et al. "The 5–HT4 Receptor", *Medicinal Research Reviews* 13 (6), pp. 633–662, (1993).
Gullikson, et al. "Gastrointestinal Motility Responses to the S and R Enantiomers of Zacopride, a 5–HT–4 Agonist and 5–HT3 Antagonis", *Drug Development Research* 26, pp. 405–417, (1992).
Eglen, et al. "Central 5–HT4 Receptors", *TiPs Review* 16, pp. 391–398, (1995).
Bockaert, et al. "5–HT4 Receptors", *CNS Drugs* 1 (1), pp. 6–15, (1994).
Romanelli, et al. "Synthesis and Biological Activity of a Series of Aryl Tropanyl Esters and Amides Chemically Related to 1H–Indole–3–carboxylic Acid endo 8–Methyl–8–azabicyclo [3.2.1]oct–3–yl Ester", *Arzneim.–Forsch./Drug Res.* 43 (II) (8), pp. 913–918 (1993).

(List continued on next page.)

*Primary Examiner*—Robert W. Ramsuer
(74) *Attorney, Agent, or Firm*—Peter C. Richardson; Gregg C. Benson; Martha G. Munchhof

(57) ABSTRACT

This invention provides a compound of the formula (I):

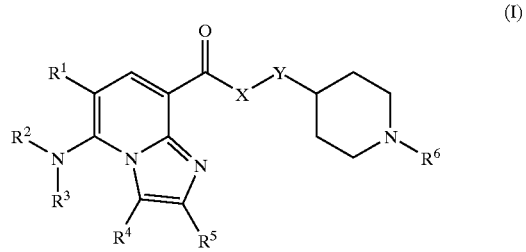

(I)

or the pharmaceutically acceptable salts thereof wherein $R^1$ is hydrogen, halo or alkyl; $R^2$ and $R^3$ are independently hydrogen, alkyl, alkenyl, alkynyl, aminoalkyl or hydroxyalkyl; or $R^2$ and $R^3$ taken together with the nitrogen atom to which they are attached may form hetrocyclic; $R^4$ is hydrogen, halo, acyl, amino, amido, aryl, arylalkyl, or heteroaryl; $R^5$ is hydrogen, halo, alkyl alkenyl, alkynyl, acyl, amino, amido, aryl, arylalkyl, or heteroaryl; $R^6$ is hydrogen, alkyl or alkoxyalkyl; X is $NR^9$ wherein $R^9$ is hydrogen or alkyl; and Y is $(CR^7R^8)_n$ wherein n is an integer from 0 to 5.

These compounds have 5-$HT_4$ receptor binding activity, and thus are useful for the treatment of gastroesophageal reflux disease, non-ulcer dyspepsia, Functional dyspepsia, irritable bowel syndrome or the like in mammalian, especially humans. This invention also provides a pharmaceutical composition comprising the above compound.

11 Claims, No Drawings

OTHER PUBLICATIONS

Kaumann, et al. "A 5–HT4–like Receptor in Human Right Atrium", *Naunyn–Schmiedeberg's Archives of Pharmacology* 344, pp. 150–159, (1991).

Mutterer, et al. "Halogenierte Pyridine V. Fluorierte und Bromierte Pyridinverbindungen", *Helv. Chim. Acta* 59 (1), pp. 23–24, (1976).

Barlow, et al. "Diels–Alder Reactions of trichloro–1,2,4–triazine: Intramolecular Additions with 1,5 and 1,6 Dienes", *J. Chem.Soc, Perkin Trans. 1*, pp. 519–524 (1995).

Lantos, et al. "Nove Cage Compounds from Inter–intra–molecular Diels–Alder Reactions of 1,2,4–Triazines with Cyclo–octa–1,5–diene", *J.Chem.Soc., Chem. Commun.*, pp. 1482–1482, (1988).

T.W. Greene, et al. "Protection for the Hydroxyl Group, Including 1,2–and 1,3–Diols", *Protective Groups in Organic Synthesis*, 2$^{nd}$ Edition, pp. 10–142, (1991).

T.W. Greene, et al. "Protection for the Amino Group", *Protective Groups in Organic Synthesis*, 2$^{nd}$ Edition, pp. 309–405 (1991).

T.W. Greene, et al. "Protection for the Carboxyl Group", *Protective Groups on ORganic Synthesis*, 3$^{rd}$ Edition, pp. 369–377.

Feibush, et al. "Chiral Separation of Heterocyclic Drugs by HPLC: Solute–Stationary Phase Base–Pair Interactions", *J.Am.Chem.Soc.* 108, pp. 3310–3318, (1986).

Baxter, et al. "5–Hydroxytryptamine4 Receptors Mediate Relaxation of the Rat Oesophageal Tunica Muscularis Mucosae", *Naunyn–Schmiedeberg's Arch. Pharmacol.* 343, pp. 439–446 (1991).

Mine, et al. "Comparison of Effect of Mosapride Citrate and Existing 5–HT4 Receptor", *JPET* 283 (3), pp. 1000–1008, (1997).

Reeves, et al. "Investigation into the 5–hydroxytryptamine Receptor Mediating Smooth Muscle Relaxation in the Rat Oesophagus", *Br. J. Pharmacol.* 104, pp. 1067–1072 (1991).

Coldwell, et al. "The Synthesis, and Dopamine D2 and Serotonin 5–HT3 Receptor Affinity of 3–Aza Analogues (Pyridyl) of 4–Amino–5–chloro–2–methoxybenzamides", *Bioorg. & Med. Chemistry Letters* 5 (1), pp. 39–42, (1995).

Itoh, et al. "Synthesis and Pharmacological Evaluation of Carboxamide Derivatives as Selective Serotoninergic 5–HT4 Receptor Agonists" *Eru. J. Med. Chem.*, 34, pp. 329–341 (1999).

Grob, et al. "Polar Substituent Effects in the Solvolysis of Primary and Tertiary Alkyl Halides. Polar Effect IX", *Helvetica Chimcia Acta* 63 (8) (226), pp. 2152–2158, (1980).

Prugh, et al. "A Simple Method of Protecting a Secondary Amine with tert Butyloxycarbonyl (BOC) in the Presence of a Primary Amien", *Synthetic Communications* 22 (16), pp. 2357–2360 (1992).

Kimpe, et al. "A Convenient Synthesis of 1–Chloro–2–alkanones", *Synthesis* 2, pp. 188–190, (1987).

Blanco, et al. "Halogenation of Enol Silyl Ethers. Synthesis of Various Types of β–Bromocarbonyl Compounds", *Synthesis*, pp 194–196 (1976).

Feibush, et al. "Chiral Separation of Heterocyclic Drugs by HPLC: Solute–Stationary Phase Base–Pair Interactions", *J.Am.Chem.Soc.*, 108, pp. 3310–3318 (1986).

Lopez–Rodriguez, et al. "Benzimidazole Derivatives. Part 1: Synthesis and Structure–Activity Relationships of New Benzimidazole–4–carboxamides and Carboxylates as Potent and Selective 5–HT4 Receptor Antagonists", *Bioorg. & Med. Chemistry* 7, pp. 2271–2281 (1999).

Klein, et al. "Design of a New Class of Orally Active Fibrinogen Receptor Antagonists", *J.Med. Chem.* 41, pp. 2492–2502, (1998).

Francis Mutterer, et al. "Halogenated pyridines v. fluorinated and brominated pyridine compounds", *Helvetica Chimica Acta*, vol. 59, Fasc. 1(1976) No. 23–24, pp. 229–235 (Translation of German article).

IMIDAZOPYRIDINE COMPOUNDS AS 5-HT4 RECEPTOR MODULATORS

CROSS-REFERENCE TO RELATED APPLICATION

This application claims priority from U.S. non-provisional application No. 60/343,371 filed on Oct. 22, 2001.

TECHNICAL FIELD

This invention relates to novel imidazopyridine compounds. These compounds have 5-HT$_4$ receptor binding activity (e.g., agonist or antagonist activities), and thus are useful for the treatment of or prevention of gastroesophageal reflux disease, gastrointestinal disease, gastric motility disorder, non-ulcer dyspepsia, Functional dyspepsia, irritable bowel syndrome, constipation, dyspepsia, esophagitis, gastroesophageral disease, nausea, central nervous system disease, alzheimers disease, cognitive disorder, emesis, migraine, neurological disease, pain, ischaemic stroke, anxiety, cardiovascular disorder or the like, in mammalian, especially human. The present invention also relates to a pharmaceutical composition comprising the above compounds.

BACKGROUND ART

Serotonin (5-HT) receptors are known to have a plurality of subtypes such as 5-HT$_1$, 5-HT$_2$, 5-HT$_3$ and 5-HT$_4$. These 5-HT$_4$ receptors are disclosed in, for example, European Journal of Pharmacology 146 (1988), 187–188, and Naunyn-Schmiedeberg's Arch. Pharmacol. (1989) 340:403–410.

5-HT$_4$ receptor modulators (e.g., agonists and antagonists) are found to be useful for the treatment of a variety of diseases such as gastroesophageal reflux disease, gastrointestinal disease, gastric motility disorder, non-ulcer dyspepsia, Functional dyspepsia, irritable bowel syndrome, constipation, dyspepsia, esophagitis, gastroesophageral disease, nausea, central nervous system disease, alzheimers disease, cognitive disorder, emesis, migraine, neurological disease, pain, and cardiovascular disorders such as cardiac failure and heart arryhthmia (See TiPs, 1992, 13, 141; Ford A. P. D. W. et al., Med. Res. Rev., 1993, 13, 633; Gullikson G. W. et al., Drug Dev. Res., 1992, 26, 405; Richard M. Eglen et al, TiPS, 1995, 16, 391; Bockaert J. et al., CNS Drugs, 1, 6; Romanelli M. N. et al., Arzheim Forsch./Drug Res., 1993, 43, 30 913; Kaumann A. et al., Naunyn-Schmiedeberg's. 1991, 344, 150; and Romanelli M. N. et al., Arzheim Forsch./Drug Res., 1993, 43, 913).

A variety of imidazopyridine compounds have been known as 5HT receptor antagonists or agonists. For example, Japanese Patent Publication Laid-Open No. H01-258,674 and H02-643,274 disclose imidazopyridine compounds as 5HT receptor antagonists. WO 96/05166 discloses imidazopyridine compounds as 5HT$_4$ agonists. WO92/15593; U.S. Pat. No. 5,260,303; U.S. Pat. No. 5,604,239; U.S. Pat. No. 5,591,749; U.S. Pat. No. 5,219,850; U.S. Pat. No. 5,434,161; U.S. Pat. No. 5,137,893; U.S. Pat. No. 5,196,547; and EP 504679 describe a variety of imidazopyridine compounds as 5HT$_3$ receptor antagonists. WO94/08998 discloses imidazopyridine compounds as 5HT$_4$ receptor antagonists.

Also, imidazopyridine compounds synthesized for different uses are described in JP2001/6877; WO01/5763; WO 99/50247; WO 97/27852, WO 9738665 and EP 274867.

It would be desirable if there were provided 5HT$_4$ receptor modulators (e.g., agonists and antagonists) which have more 5HT$_4$ receptor modulating activities (e.g., angonist or antagonist activities).

BRIEF DISCLOSURE OF THE INVENTION

The present invention provides a compound of the following formula (I):

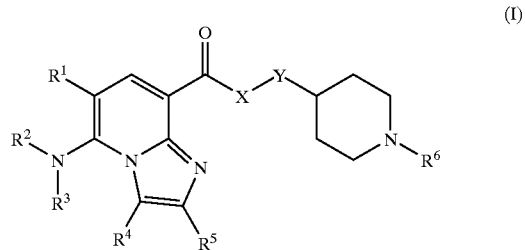

(I)

or the pharmaceutically acceptable salts thereof wherein
R$^1$ is hydrogen, halo or C$_{1-6}$ alkyl;
R$^2$ and R$^3$ are independently hydrogen, C$_{1-6}$ alkyl, C$_{2-6}$ alkenyl, C$_{2-6}$ alkynyl, mono- or di-(C$_{1-5}$)alkyl amino, amino(C$_{1-5}$)alkyl or hydroxy(C$_{1-5}$)alkyl; or R$^2$ and R$^3$ taken together with the nitrogen atom to which they are attached may form substituted or non-substituted nitrogen-containing hetrocyclic;
R$^4$ is hydrogen, halo, C$_{1-8}$ acyl, amino, amido, substituted or non-substituted aryl, substituted or non-substituted aryl(C$_{1-6}$)alkyl, or substituted or non-substituted heterocyclic;
R$^5$ is hydrogen, halo, C$_{1-6}$ alkyl, C$_{2-6}$ alkenyl, C$_{2-6}$ alkynyl, C$_{1-8}$ acyl, amino, amido, substituted or non-substituted aryl, substituted or non-substituted aryl(C$_{1-6}$)alkyl, or substituted or non-substituted heterocyclic;
R$^6$ is hydrogen, C$_{1-6}$ alkyl or C$_{1-6}$ alkoxy (C$_{1-6}$)alkyl;
X is NR$^9$ wherein R$^9$ is hydrogen or C$_{1-6}$ alkyl; and
Y is (CR$^7$R$^8$)$_n$ wherein R$^7$ and R$^8$ are independently hydrogen or C$_{1-6}$ alkyl, and n is an integer from 0 to 5.

The imidazopyridine compounds of this invention have 5-HT$_4$ receptor modulating activities (e.g., an antagonistic or agonistic function towards 5-HT$_4$ receptor), and are thus useful for the treatment or prevention of disease conditions mediated by 5-HT$_4$ receptor activities.

Thus, the present invention provides a pharmaceutical composition for the treatment of disease conditions mediated by 5-HT$_4$ receptor activities, in a mammalian subject, which comprises administering to said subject a therapeutically effective amount of a compound of formula (I).

Further, the present invention also provides a pharmaceutical composition for the treatment of gastroesophageal reflux disease, gastrointestinal disease, gastric motility disorder, upper gut motility disorder, non-ulcer dyspepsia, Functional dyspepsia, irritable bowel syndrome, constipation, dyspepsia, esophagitis, gastroesophageral disease, nausea, central nervous system disease, alzheimers disease, cognitive disorder, emesis, migraine, neurological disease, pain, ischaemic stroke, anxiety, cardiovascular disorders such as cardiac failure and heart arryhthmia, or the like, which comprises a therapeutically effective amount of the imidazopyridine compound of formula (I) or its pharmaceutically acceptable salt together with a pharmaceutically acceptable carrier.

Also, the present invention provides a method for the treatment of disease conditions mediated by 5-HT$_4$ receptor activities, in a mammalian subject, which comprises administering to said subject a therapeutically effective amount of a compound of formula (I). Further, the present invention provides a method for the treatment of the disease conditions as mentioned above. Furthermore, the present invention provides use of the compound of formula (I) in the manufacture of a medicament for the treatment or prevention of disease conditions mediated by 5-$HT_4$ receptor activity, in a mammalian subject. The conditions mediated by 5-$HT_4$ receptor activity are those diseases or disorders described as above.

DETAILED DESCRIPTION OF THE INVENTION

As used herein, the term "halo" means fluoro, chloro, bromo and iodo, preferably fluoro or chloro.

As used herein, the term "alkyl" means straight or branched chain saturated radicals, including, but not limited to methyl, ethyl, n-propyl, isopropyl, n-butyl, iso-butyl, secondary-butyl, tertiary-butyl.

As used herein, the term "alkenyl" means a hydrocarbon radical having at least one double bond including, but not limited to, ethenyl, propenyl, 1-butenyl, 2-butenyl and the like.

As used herein, the term "alkynyl" means a hydrocarbon radical having at least one triple bond including, but not limited to, ethynyl, propynyl, 1-butynyl, 2-butynyl and the like.

As used herein, the term "alkoxy" means alkyl-O—, including, but not limited to methoxy, ethoxy, n-propoxy, isopropoxy, n-butoxy, iso-butoxy, secondary-butoxy, tertiary-butoxy.

As used herein, the term "acyl" means a group having carbonyl such as R'''—C(O)— wherein R''' is $C_{1-5}$ alkyl, phenyl or $C_{3-7}$ cycloalkyl, including, but not limited to formyl, acetyl, ethyl-C(O)—, n-propyl-C(O)—, isopropyl-C(O)—, n-butyl-C(O)—, iso-butyl-C(O)—, secondary-butyl-C(O)—, tertiary-butyl-C(O)—, cyclopropyl-C(O)—, cyclobutyl-C(O)—, cyclopentyl-C(O)—, cyclohexyl-C(O)—, cycloheptyl-C(O)—, and the like.

As used herein, the term "nitrogen-containing heterocyclic" means 5- to 10-membered monocyclic or bicyclic rings having at least one nitrogen ring atom, including, but not limited to, a heterocyclic ring selected from morpholino, piperazino, piperidino, pyrrolidino, azetidino, pyrazolidino, (1,2,3,4)-tetrahydroisoqunolino and perhydroisoquinolino, preferably morpholino, piperazino and piperidino.

As used herein, the term "aryl" means a monocyclic or bicyclic aromatic carbocyclic ring of 6 to 11 carbon atoms including, but not limited to, phenyl, naphthyl, indanyl, (1,2,3,4)-tetrahydronaphthyl, indenyl and isoindenyl, preferably phenyl and naphthyl.

As used herein, the term "arylalkyl" means an alkyl radical which is substituted by an aryl group as defined above.

As used herein, the term "heterocyclic" means a 5- to 10-membered monocyclic or bicyclic ring which may be saturated, partially unsaturated, or aromatic, and which consists of carbon atoms and from 1 to 4 heteroatoms independently selected from the group consisting of N, O and S. Examples of the heterocyclics include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H, 6H-1,5,2-dithiazinyl, thiophenyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4a H-carbazole, carbazole, .beta.-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Preferable heterocyclic groups include piperidino, morpholino, thiamorpholino, pyrrolidino, pyrazolino, pyrazolidino, pyrazoryl, piperazinyl, furyl, thienyl, oxazolyl, tetrazolyl, thiazolyl, imidazolyl, imidazolinyl, pyrazolyl, pyridyl, pyrimidinyl, pyrrolyl, pyrrolidinyl and quinolyl.

As used herein, the term "substituted nitrogen-containing heterocyclic, substituted aryl, substituted arylalkyl or substituted heterocyclic" means those groups which are substituted with one to three (preferably one to two) substituents selected from halo, alkyl, amino, hydroxy, cyano, mono- or di-alkylamino, alkoxy, and alkoxyalkyl.

As used herein, the term "modulator" means compounds, agonists, antagonists, ligands, substrates and enzymes, which directly or indirectly affect regulation of the receptor activity.

In the compounds of formula (I), $R^1$ is preferably hydrogen, halo or $C_{1-3}$ alkyl, more preferably hydrogen or halo.

In the compounds of formula (I), $R^2$ and $R^3$ are preferably hydrogen, $C_{1-3}$ alkyl, mono- or di-($C_{1-5}$)alkyl amino, amino ($C_{1-5}$)alkyl or hydroxy($C_{1-5}$)alkyl; or $R^2$ and $R^3$ taken together with the nitrogen atom to which they are attached may form a substituted or non-substituted nitrogen-containing hetrocyclic ring; more preferably hydrogen or $C_{1-3}$ alkyl; or $R^2$ and $R^3$ taken together with the nitrogen atom to which they are attached may form hetrocyclic selected from morpholino, piperazino, piperidino, pyrrolidino, azetidino, pyrazolidino, (1,2,3,4)-tetrahydroisoqunolino and perhydroisoquinolino, which may be optionally substituted with halo, $C_{1-3}$ alkyl, $C_{1-3}$ alkoxy, mono- or di-($C_{1-3}$)alkyl amino or $C_{1-3}$ alkoxy($C_{1-3}$) alkyl; and most preferably hydrogen or $C_{1-3}$ alkyl; or $R^2$ and $R^3$ taken together with the nitrogen to which they are attached may form hetrocyclic selected from morpholino, piperazino and piperidino.

In the compounds of formula (I), $R^4$ is preferably hydrogen, halo, $C_{1-3}$ acyl, substituted or non-substituted aryl, substituted or non-substituted aryl($C_{1-3}$)alkyl, or substituted or non-substituted heterocyclic; more preferably hydrogen, halo, $C_{1-3}$ alkyl, $C_{1-3}$ acyl, aryl selected from phenyl and naphthyl, arylalkyl selected from phenyl $C_{1-3}$ alkyl and naphthyl $C_{1-3}$ alkyl, or heteroaryl selected from piperidino, morpholino, thiamorpholino, pyrrolidino, pyrazolino, pyrazolidino, pyrazoryl, piperazinyl, furyl, thienyl, oxazolyl, tetrazolyl, thiazolyl, imidazolyl, imidazolinyl, pyrazolyl, pyridyl, pyrimidinyl, pyrrolyl, pyrrolidinyl and quinolyl, wherein said aryl, arylalkyl or heteroaryl may optionally be substituted with halo, $C_{1-3}$ alkyl, $C_{1-3}$ alkoxy, mono- or di-$(C_{1-3})$alkyl amino or $C_{1-3}$ alkoxy $(C_{1-3})$ alkyl; more preferably hydrogen, halo, $C_{1-3}$ alkyl, $C_{1-3}$ acyl, phenyl, naphthyl, benzyl, piperidino, morpholino, pyrrolidino, pyrazolino, pyrazoryl, piperazinyl, furyl, thienyl, oxazolyl, tetrazolyl, thiazolyl, imidazolyl, pyridyl, pyrimidinyl and pyrrolyl; and most preferably hydrogen, halo or $C_{1-3}$ alkyl.

In the compounds of formula (I), $R^5$ is preferably hydrogen, halo, $C_{1-3}$ alkyl, $C_{1-3}$ acyl, amido, substituted or non-substituted aryl, substituted or non-substituted aryl$(C_{1-3})$alkyl, or substituted or non-substituted heterocyclic; more preferably hydrogen, halo, $C_{1-3}$ alkyl, $C_{1-3}$ acyl, aryl selected from phenyl and naphthyl, arylalkyl selected from phenyl $C_{1-3}$ alkyl and naphthyl $C_{1-3}$ alkyl, or heteroaryl selected from piperidino, morpholino, thiamorpholino, pyrrolidino, pyrazolino, pyrazolidino, pyrazoryl, piperazinyl, furyl, thienyl, oxazolyl, tetrazolyl, thiazolyl, imidazolyl, imidazolinyl, pyrazolyl, pyridyl, pyrimidinyl, pyrrolyl, pyrrolidinyl and quinolyl, wherein said aryl, arylalkyl or heteroaryl may optionally be substituted with halo, $C_{1-3}$ alkyl, $C_{1-3}$ alkoxy, mono- or di-$(C_{1-3})$alkyl amino or $C_{1-3}$ alkoxy$(C_{1-3})$ alkyl; more preferably hydrogen, halo, $C_{1-3}$ alkyl, $C_{1-3}$ acyl, phenyl, naphthyl, benzyl, piperidino, morpholino, pyrrolidino, pyrazolino, pyrazoryl, piperazinyl, furyl, thienyl, oxazolyl, tetrazolyl, thiazolyl, imidazolyl, pyridyl, pyrimidinyl and pyrrolyl; and most preferably hydrogen, halo or $C_{1-3}$ alkyl.

In the compounds of formula (I), $R^6$ is preferably hydrogen, $C_{1-5}$ alkyl or $C_{1-3}$ alkoxy $(C_{1-5})$alkyl; preferably $C_{1-5}$ alkyl or $C_{1-3}$ alkoxy $(C_{1-5})$alkyl; more preferably $C_{1-4}$ alkyl or $C_{1-3}$ alkoxy $(C_{1-4})$alkyl; and preferably $C_{3-4}$ alkyl or methoxy $(C_{1-4})$alkyl.

In the compounds of formula (I), X is preferably $NR^9$, wherein $R^9$ is independently hydrogen or $C_{1-3}$ alkyl; more preferably $NR^9$, wherein $R^9$ is independently hydrogen or methyl; most preferably NH.

In the compounds of formula (I), Y is preferably $(CR^7R^8)_n$, wherein $R^7$ and $R^8$ are independently hydrogen or $C_{1-3}$ alkyl, and n is an integer from 0 to 3, more preferably $(CR^7R^8)_n$ (wherein $R^7$ and $R^8$ are independently hydrogen or methyl, and n is an integer from 0 to 2; most preferably chemical bond or methylene.

Preferred compounds of this invention are those of the formula (I) wherein
  $R^1$ is hydrogen, halo or $C_{1-3}$ alkyl;
  $R^2$ and $R^3$ are independently hydrogen, $C_{1-3}$ alkyl, mono- or di-$(C_{1-5})$alkyl amino, amino$(C_{1-5})$alkyl or hydroxy $(C_{1-5})$alkyl; or $R^2$ and $R^3$ taken together with the nitrogen atom to which they are attached may form substituted or non-substituted nitrogen-containing hetrocyclic;
  $R^4$ is hydrogen, halo, $C_{1-3}$ acyl, substituted or non-substituted aryl, $(C_{1-3})$alkyl, or substituted or non-substituted heterocyclic;
  $R^5$ is hydrogen, halo, $C_{1-3}$ alkyl, $C_{1-3}$ acyl, amido, substituted or non-substituted aryl, substituted or non-substituted aryl$(C_{1-3})$alkyl, or substituted or non-substituted heterocyclic;
  $R^6$ is hydrogen, $C_{1-5}$ alkyl or $C_{1-3}$ alkoxy $(C_{1-5})$alkyl;
  X is $NR^9$; and Y is $(CR^7R^8)_n$, wherein $R^7$, $R^8$ and $R^9$ are independently hydrogen or $C_{1-3}$ alkyl, and n is an integer from 0 to 3.

More preferred compounds of this invention are those of the formula (I) wherein
  $R^1$ is hydrogen or halo;
  $R^2$ and $R^3$ are independently hydrogen or $C_{1-3}$ alkyl; or $R^2$ and $R^3$ taken together with the nitrogen atom to which they are attached may form hetrocyclic selected from morpholino, piperazino, piperidino, pyrrolidino, azetidino, pyrazolidino, (1,2,3,4)-tetrahydroisoqunolino and perhydroisoquinolino, which may be optionally substituted with halo, $C_{1-3}$ alkyl, $C_{1-3}$ alkoxy, mono- or di-$(C_{1-3})$alkyl amino or $C_{1-3}$ alkoxy$(C_{1-3})$ alkyl;
  $R^4$ is hydrogen, halo, $C_{1-3}$ acyl, aryl selected from phenyl and naphthyl, arylalkyl selected from phenyl $C_{1-3}$ alkyl and naphthyl $C_{1-3}$ alkyl, or heteroaryl selected from piperidino, morpholino, thiamorpholino, pyrrolidino, pyrazolino, pyrazolidino, pyrazoryl, piperazinyl, furyl, thienyl, oxazolyl, tetrazolyl, thiazolyl, imidazolyl, imidazolinyl, pyrazolyl, pyridyl, pyrimidinyl, pyrrolyl, pyrrolidinyl and quinolyl, wherein said aryl, arylalkyl or heteroaryl may optionally be substituted with halo, $C_{1-3}$ alkyl, $C_{1-3}$ alkoxy, mono- or di-$(C_{1-3})$alkyl amino or $C_{1-3}$ alkoxy$(C_{1-3})$ alkyl;
  $R^5$ is hydrogen, halo, $C_{1-3}$ alkyl, $C_{1-3}$ acyl, amido, aryl selected from phenyl and naphthyl, arylalkyl selected from phenyl $C_{1-3}$ alkyl and naphthyl $C_{1-3}$ alkyl, or heteroaryl selected from piperidino, morpholino, thiamorpholino, pyrrolidino, pyrazolino, pyrazolidino, pyrazoryl, piperazinyl, furyl, thienyl, oxazolyl, tetrazolyl, thiazolyl, imidazolyl, imidazolinyl, pyrazolyl, pyridyl, pyrimidinyl, pyrrolyl, pyrrolidinyl and quinolyl, wherein said aryl, arylalkyl or heteroaryl may optionally be substituted with halo, $C_{1-3}$ alkyl, $C_{1-3}$ alkoxy, mono- or di-$(C_{1-3})$alkyl amino or $C_{1-3}$ alkoxy$(C_{1-3})$ alkyl;
  $R^6$ is $C_{1-5}$ alkyl or $C_{1-3}$ alkoxy $(C_{1-5})$alkyl;
  X is $NR^9$; and Y is $(CR^7R^8)_n$, wherein $R^7$, $R^8$ and $R^9$ are independently hydrogen or methyl, and n is an integer from 0 to 2.

Also, preferred compounds of this invention are those of the formula (I) wherein
  $R^1$ is halo;
  $R^2$ and $R^3$ are independently hydrogen, $C_{1-3}$ alkyl; or $R^2$ and $R^3$ taken together with the nitrogen to which they are attached may form hetrocyclic selected from morpholino, piperazino and piperidino;
  $R^4$ is hydrogen, halo, $C_{1-3}$ acyl, phenyl, naphthyl, benzyl, piperidino, morpholino, pyrrolidino, pyrazolino, pyrazoryl, piperazinyl, furyl, thienyl, oxazolyl, tetrazolyl, thiazolyl, imidazolyl, pyridyl, pyrimidinyl and pyrrolyl;
  $R^5$ is hydrogen, halo, $C_{1-3}$ alkyl, $C_{1-3}$ acyl, amido, phenyl, naphthyl, benzyl, piperidino, morpholino, pyrrolidino, pyrazolino, pyrazoryl, piperazinyl, furyl, thienyl, oxazolyl, tetrazolyl, thiazolyl, imidazolyl, pyridyl, pyrimidinyl and pyrrolyl;
  $R^6$ is $C_{1-4}$ alkyl or $C_{1-3}$ alkoxy $(C_{1-4})$alkyl;
  X is NH; and
  Y is chemical bond or methylene.

Also, more preferred compounds of this invention are those of the formula (I) wherein
  $R^1$ is chloro; $R^2$ and $R^3$ are independently hydrogen or $C_{1-3}$ alkyl; $R^4$ is hydrogen or halo; $R^5$ is hydrogen, halo or $C_{1-3}$ alkyl; $R^6$ is $C_{3-4}$ alkyl or methoxy $(C_{1-4})$alkyl; X is NH; and Y is methylene.

Preferred individual compounds of this invention are:
  5-amino-N-[(1-butyl-4-piperidinyl)methyl]-6-chloroimidazo[1,2-a]pyridine-8-carboxamide;

5-amino-N-[(1-butyl-4-piperidinyl)methyl]imidazo[1,2-a]pyridine-8-carboxamide;

5-amino-6-chloro-N-[(1-(3-methoxypropyl)-4-piperidinyl]imidazo[1,2-a]pyridine-8-carboxamide;

5-amino-N-[(1-(3-methoxypropyl)-4-piperidinyl]imidazo[1,2-a]pyridine-8-carboxamide;

5-Amino-N-[(1-butyl-4-piperidiny)methyl]-6-chloro-2-methylimidazo[1,2-a]pyridine-8-carboxamide;

5-Amino-6-chloro-2-methyl-N-{1-[3-(methyloxy)propyl]-4-piperidinyl}imidazo[1,2-a]pyridine-8-carboxamide;

5-Amino-6-chloro-2-methyl-N-({1-[3-(methyloxy)propyl]-4-piperidinyl}methyl)imidazolo[1,2-a]pyridine-8-carboxyamide; and salts thereof.

Other preferred individual compounds of this invention are:

5-amino-N-[(1-isobutylpiperidin-4-yl)methyl]-2-methylimidazo[1,2-a]pyridine-8-carboxamide;

5-amino-6-chloro-N-{[1-(3,3-dimethylbutyl)piperidin-4-yl]methyl}-2-ethylimidazo[1,2-a]pyridine-8-carboxamide;

5-amino-6-chloro-2-ethyl-N-{[1-(2-methoxy-2-methylpropyl)piperidin-4-yl]methyl}imidazo[1,2-a]pyridine-8-carboxamide;

5-amino-6-chloro-2-methyl-N-{[1-(2-methoxy-2-methylpropyl)piperidin-4-yl]methyl}imidazo[1,2-a]pyridine-8-carboxamide; and 5-amino-6-chloro-N-[(1-isobutylpiperidin-4-yl)methyl]-2-methylimidazo[1,2-a]pyridine-8-carboxamide; and salts thereof.

General Synthesis

The imidazopyridine compounds of formula (I) of this invention may be prepared by a variety of synthetic methods. For example, the imidazopyridine compounds of formula (I) wherein X is NH, may be prepared by saponification of a carboxylate compound (II) to obtain a corresponding carboxylic acid compound (III), followed by a coupling reaction of the compound (III) with an amine compound (IV), as indicated in the following Scheme 1.

Scheme 1:

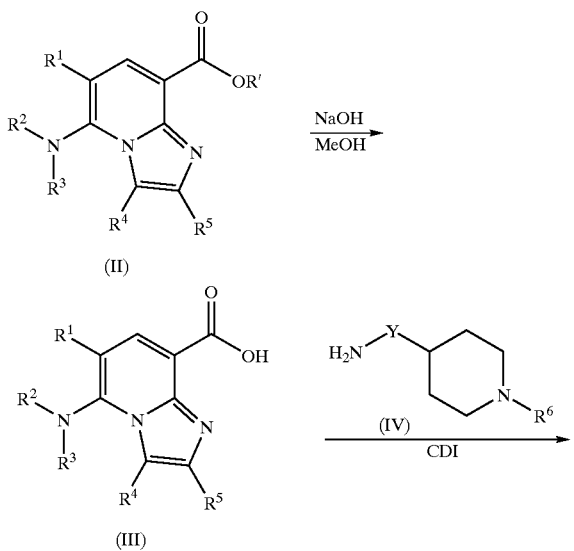

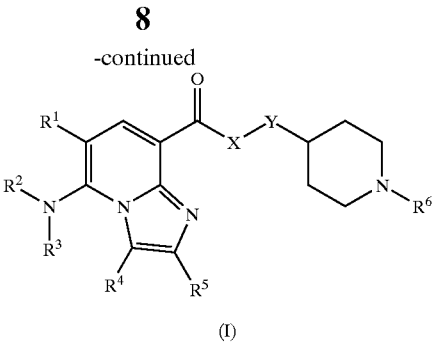

wherein R' is $C_{1-3}$ alkyl or benzyl; X is NH; and all other symbols are as already defined)

In Scheme 1, the carboxylate compound (II) may be first subjected to saponification of the ester residue at the 8-position of the imidazopyridine ring, followed by acidification to afford a corresponding carboxylic acid (III). Then, the compound (III) may be coupled with the amine compound (IV) to give an imidazopyridine compound (I) wherein X is NH.

The saponification and the acidification may be carried out by conventional procedures. In a typical procedure, the saponification is carried out by treatment with sodium hydroxide or lithium hydroxide in a suitable reaction-inert solvent. Suitable solvents include, for example, alcohols such as methanol, ethanol, propanol, butanol, 2-methoxyethanol, and ethlene gylcol; ethers such as tetrahydrofuran (THF), 1,2-dimethoxyethane (DME), and 1,4-dioxane; halogenated hydrocarbons such as chloroform, dichloroethane, and 1,2-dichloroethane; amides such as N,N-dimethylformamide (DMF) and hexamethylphospholictriamide; and sulfoxides such as dimethyl sulfoxide (DMSO). This reaction may be carried out at a temperature in the range from −20 to 100° C., usually from 20° C. to 65° C. for 30 minutes to 24 hours, usually 60 minutes to 10 hour. In a typical procedure, the acidification is carried out by treatment with diluted hydrochloric acid or 10% aqueous citric acid in a suitable reaction-inert solvent such as water at a temperature in the range from −20 to 65° C., usually from 0° C. to 30° C. for 30 minute to 10 hour, usually 30 minutes to 2 hours.

The coupling reaction may be carried out in the presence of a suitable condensation agent in a reaction-inert solvent. Suitable condensation agents include 1,1'-carbonyldiimidazole (CDI), diisopropylcarbodiimide (DIC), dicyclohexylcarbodiimide (DCC), water soluble carbodiimide (WSC), 2-ethoxy-N-ethoxycarbonyl-1,2-dihydroquinoline, benzotriazol-1-yloxy-tris (dimethylamino) phosphonium hexafluorophosphate (BOP), diethyl azodicarboxylatetriphenylphosphine, diethylcyanophosphonate (DEPC), diphenylphosphorylazide (DPPA), bromotripyrrolidino phosphonium hexafluorophosphate (PyBrop[trademark]), bis(2-oxo-3-oxazolidinyl) phosphinic chloride (BOPCl), benzotriazole-1-yl-oxy-tris-pyrrolidino-phosphonium hexafluorophosphate (PyBOP), 2-(1-H-benzotriazole-1-yl)-1,1,3,3,-tetramethyluronium hexafluorophosphate (HBTU) and ethyl chloroformate. Suitable reaction-inert solvents include aqueous or non-aqueous organic solvents such as tetrahydrofuran, N,N-dimethylformamide (DMF), dioxane, acetone, dimethoxyethane and acetonitrile; and halogenated hydrocarbons such as chloroform, dichloromethane and dichloroethane (preferably dichloromethane). This reaction may be carried out at a temperature in the range from −20 to 80° C., usually from 0° C. to 30° C. for 30 minutes to 100 hours, usually 5 hours to 24 hours.

Scheme 2:

The carboxylate compounds (II) used as starting materials in Scheme 1 may be prepared in the following reaction steps.

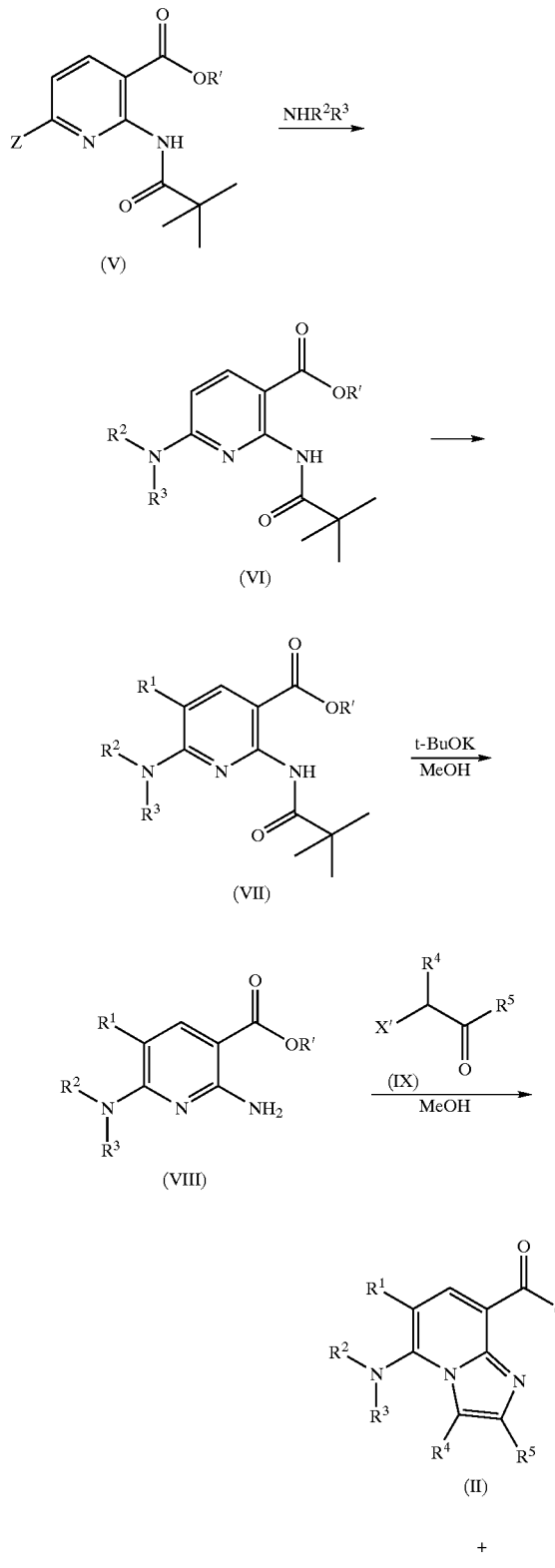

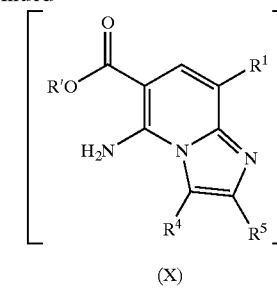

In Scheme 2, a nicotinate compound (V) wherein R' is $C_{1-3}$ alkyl or benzyl and Z is halogen; and the amino group is protected by a pivaloyl group, may be reacted with an amine compound: $NHR^2R^3$, to obtain a compound (VI). This reaction is generally carried out at a pressure from 1 to 5 atmospheres, preferably at 1 to 4 atmospheres. This reaction can be carried out in a suitable reaction-inert solvent. Suitable solvents include, for example, alcohols such as methanol, ethanol, propanol, butanol, 2-methoxyethanol and ethlene gylcol; ethers such as tetrahydrofuran, 1,2-dimethoxyethane, diethyl ether, diisopropyl ether, diphenyl ether and 1,4-dioxane; halogenated hydrocarbons such as chloroform, dichloroethane and 1,2-dichloroethane; amides such as N,N-dimethylformamide and hexamethylphospholictriamide; sulfoxides such as dimethyl sulfoxide; acetonitrile; benzene, toluene, xylene; and pyridine. This reaction may be carried out at a temperature in the range from 20 to 100° C., usually from 50° C. to 80° C. for 30 minutes to 24 hours, usually 30 minutes to 10 hours. When $R^1$ is halo, the compound (VI) is treated with halogen or N-halogenated succimide or SELECTFLUOR (trademark) under appropriate conditions, to obtain a compound (VII) wherein $R^1$ is halo. This reaction can be carried out in a suitable reaction-inert solvent such as carboxylic acids (e.g., acetic acid, propionic acid and butylic acid); halogenated hydrocarbons such as chloroform, dichloroethane and 1,2-dichloroethane; amides such as N,N-dimethylformamide and hexamethylphospholictriamide; sulfoxides such as dimethyl sulfoxide; acetonitrile; benzene, toluene, xylene; and pyridine. This reaction may be carried out at a temperature in the range from 0 to 80° C., usually from 25 to 70° C. for 5 minutes to 24 hours, usually 15 minutes to 8 hours. Then, the compound (VII) may be subject to deprotection of an amino-protecting group, to obtain a compound (VIII). The deprotection may be carried out in the presence of base (e.g., potassium tert-butoxide, sodium ethoxide and sodium hydroxide) or acids (e.g., hydrochloric acid and sulfuric acid). The deprotection can be carried out in a suitable reaction-inert solvent such as methanol at a temperature in the range from 25 to 80° C., usually from 50 to 65° C. for 10 minutes to 24 hours, usually 30 minutes to 10 hours.

Then, the compound (VIII) may be reacted with a compound (IX) wherein X' is halogen, to obtain a compound (II) and a compound (X). This reaction can be carried out in the presence of 2-halogenated aldehyde or 2-halogenated ketone (compound (IX)) in a suitable reaction-inert solvent such as methanol, ethanol, propanol and butanol at a temperature in the range from 25 to 120° C., usually from 50° C. to 65° C.

for 8 hours to 72 hours, usually 8 hours to 24 hours. The resulting mixture of the compound (II) and the compound (X) may be subjected to conventional separation techniques to obtain the compound (II). Suitable conventional separation techniques include silica gel column chromatography.

In addition, starting compounds of formula (V) are known or may be prepared from a known compound according to procedures known to those skilled in the art.

Scheme 3:

Compounds (I') (Compound (I) wherein $R^1$ is hydrogen) can be prepared by subjecting a compound (I) wherein $R^1$ is halo, to catalytic hydrogenation.

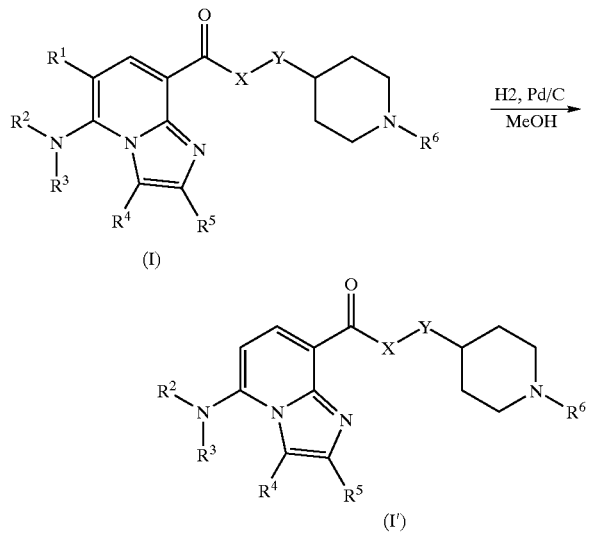

In Scheme 3, the catalytic hydrogenation can be carried out in the presence of hydrogen or hydrogen source such as ammonium formate, and a suitable metal containing catalysts such as palladium, platinum, nickel, platinum oxide and rhodium in a suitable reaction-inert solvent such as methanol. The preferred catalyst is palladium on carbon. This hydrogenation can be carried out at a temperature in the range from 20 to 100° C., usually from 25° C. to 80° C. for 5 minutes to 48 hours, usually 30 minutes to 2 hours.

Scheme 4:

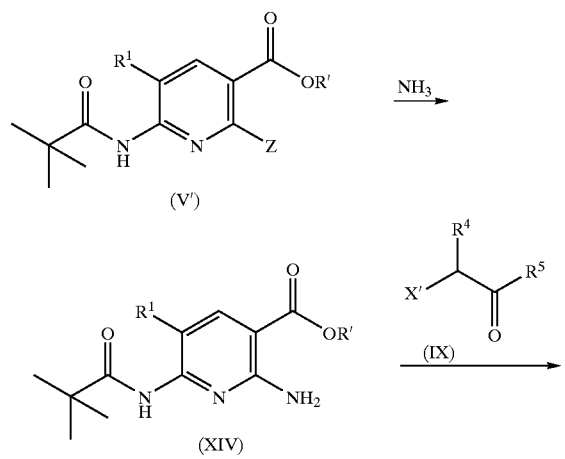

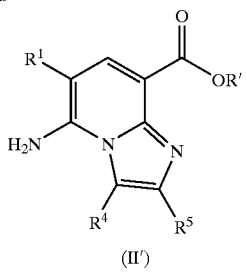

In scheme 4, the compound (V') may be reacted with an ammonia water to obtain a compound (XIV). This reaction is generally carried out in a sealed tube. This reaction can be carried out in a suitable reaction-inert solvent. Suitable solvents include, for example, alcohols such as methanol, ethanol, propanol, butanol, 2-methoxyethanol and ethlene gylcol; ethers such as THF, DME, diethyl ether, diisopropyl ether, diphenyl ether and 1,4-dioxane; halogenated hydrocarbons such as chloroform, dichloroethane and 1,2-dichloroethane; amides such as DMF and hexamethylphospholictriamide; sulfoxides such as DMSO; acetonitrile; benzene, toluene, xylene; and pyridine. This reaction may be carried out at a temperature in the range from 30 to 150° C., usually from 50° C. to 100° C. for 30 minutes to 24 hours, usually 30 minutes to 12 hours. Compounds (II') may be prepared by reacting a compound (XIV) with the compound (IX) under appropriate conditions. This reaction can be carried out in a suitable reaction-inert solvent such as methanol. This reaction may be carried out at a temperature in the range from 25 to 65° C., usually from 50° C. to 65° C. for 30 minutes to 48 hours, usually 30 minutes to 12 hours.

Scheme 5:

The nicotinate compounds (V) and (V') used as starting materials in Scheme 2,4,6 and 7 may be prepared in the following reaction steps.

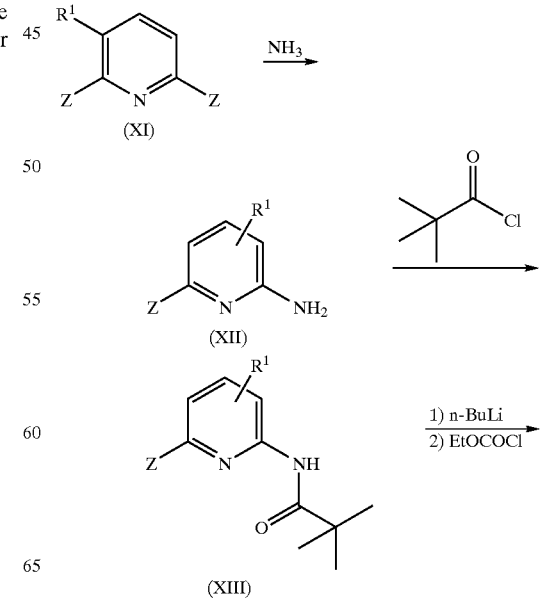

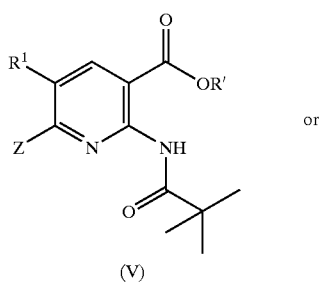

(V)

or

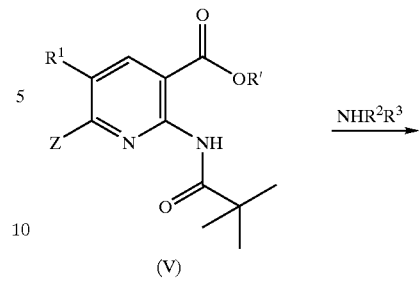

(V)

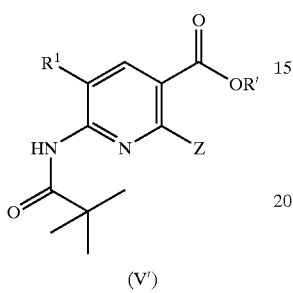

(V')

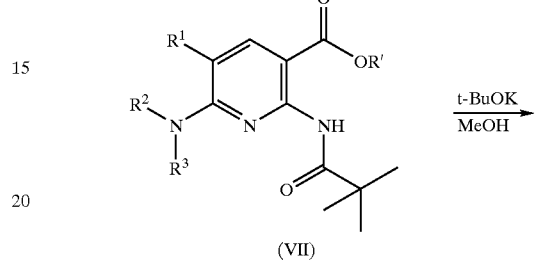

(VII)

In scheme 5, a pyridine compound (XI) wherein $R^1$ is $C_{1-6}$ alkyl and Z is halogen, may be reacted with an ammonia water to obtain a compound (XII). This reaction is generally carried out in a sealed tube. This reaction may be carried out at a temperature in the range from 50 to 200° C., usually from 100° C. to 160° C. for 30 minutes to 24 hours, usually 30 minutes to 12 hours. The compound (XII) is treated with pivaloyl chloride in the presence of base, such as diisopropylethylamine, triethylamine, pyridine and lutidine to obtain a mixture of compound (XIII). This reaction can be carried out in a suitable reaction-inert solvent. Suitable solvents include, for example, halogenated hydrocarbons such as chloroform, dichloroethane and 1,2-dichloroethane. This reaction may be carried out at a temperature in the range from −20 to 50° C., usually from −10° C. to 30° C. for 30 minutes to 24 hours, usually 30 minutes to 10 hours. The compound (XII) is treated with n-BuLi followed by ethyl chloroformate or carbobenzyloxychloride to obtain a compound (V) and (V'). This reaction can be carried out in a suitable reaction-inert solvent. Suitable solvents include, for example, ethers such as tetrahydrofuran, 1,2-dimethoxyethane, diethyl ether, diisopropyl ether, diphenyl ether and 1,4-dioxane. This reaction may be carried out at a temperature in the range from −100 to 50° C., usually from −100 to 20° C. for 5 minutes to 24 hours, usually 15 minutes to 8 hours. In addition, starting compounds of formula (XI) are known or may be prepared from a known compound according to procedures known to those skilled in the art, for example, Helv. Chim. Acta (1976), 59, 229–35, J. Chem. Soc., Perkin Trans. 1 (1996), 519–24 and J. Chem. Soc., Chem. Commun. (1988), 1482–3.

Scheme 6:

The carboxylate compounds (II) used as starting materials in Scheme 1 may be prepared in the following reaction steps.

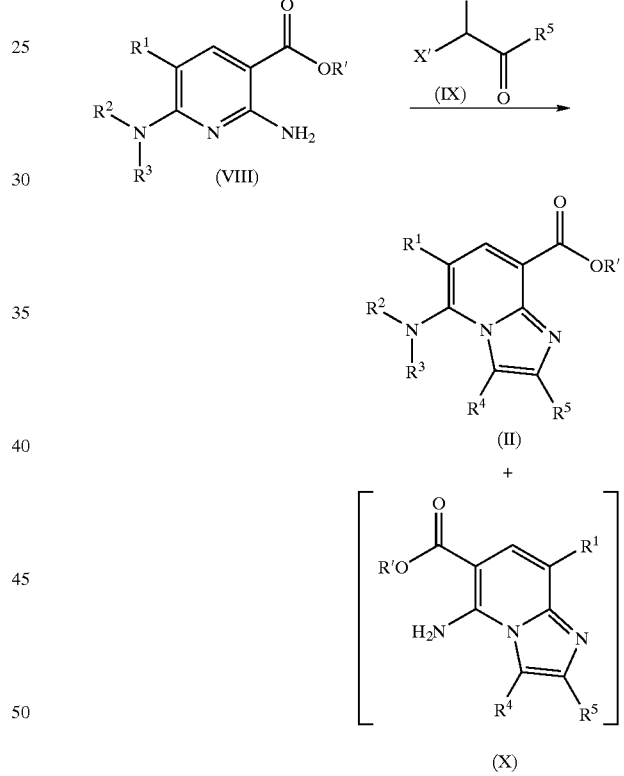

In Scheme 6, a nicotinate compound (V) wherein $R^1$ is $C_{1-6}$ alkyl, R' is $C_{1-3}$ alkyl or benzyl and Z is halogen; and the amino group is protected by a pivaloyl group, may be reacted with an amine compound: $NHR^2R^3$, to obtain a compound (VII). This reaction is generally carried out at a pressure from 1 to 5 atmospheres, preferably at 1 to 4 atmospheres. This reaction can be carried out in a suitable reaction-inert solvent. Suitable solvents include, for example, alcohols such as methanol, ethanol, propanol, butanol, 2-methoxyethanol and ethylene gylcol; ethers such as tetrahydrofuran, 1,2-dimethoxyethane, diethyl ether, diisopropyl ether, diphenyl ether and 1,4-dioxane; halogenated hydrocarbons such as chloroform, dichloroethane and 1,2-dichloroethane; amides such as N,N- dimethylformamide and hexamethylphospholictriamide; sulfoxides such as dimethyl sulfoxide; acetonitrile; benzene, toluene, xylene; and pyridine. This reaction may be carried out at a temperature in the range from 20 to 100° C., usually from 50° C. to 80° C. for 30 minutes to 24 hours, usually 30 minutes to 10 hours. Then, the compound (VII) may be subject to deprotection of an amino-protecting group, to obtain a compound (VII). The deprotection may be carried out in the presence of base (e.g., potassium tert-butoxide, sodium ethoxide and sodium hydroxide) or acids (e.g., hydrochloric acid and sulfuric acid). The deprotection can be carried out in a suitable reaction-inert solvent such as methanol at a temperature in the range from 25 to 80° C., usually from 50 to 65° C. for 10 minutes to 24 hours, usually 30 minutes to 10 hours.

Then, the compound (VIII) may be reacted with a compound (IX) to obtain a compound (II) and a compound (X). This reaction can be carried out in the presence of 2-halogenated aldehyde or 2-halogenated ketone (compound (IX)) in a suitable reaction-inert solvent such as methanol, ethanol, propanol and butanol at a temperature in the range from 25 to 120° C., usually from 50° C. to 65° C. for 8 hours to 72 hours, usually 8 hours to 24 hours. The resulting mixture of the compound (II) and the compound (X) may be subjected to conventional separation techniques to obtain the compound (II). Suitable conventional separation techniques include silica gel column chromatography.

Scheme 7:

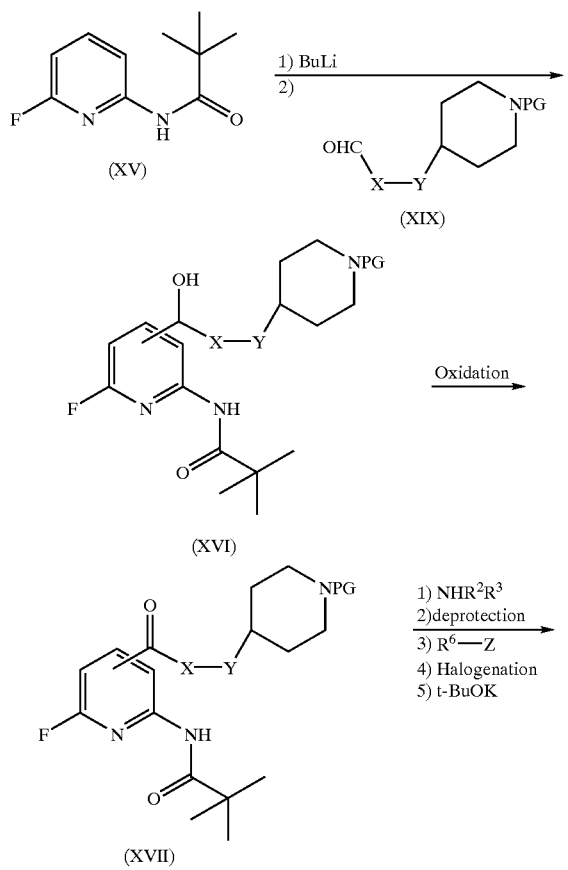

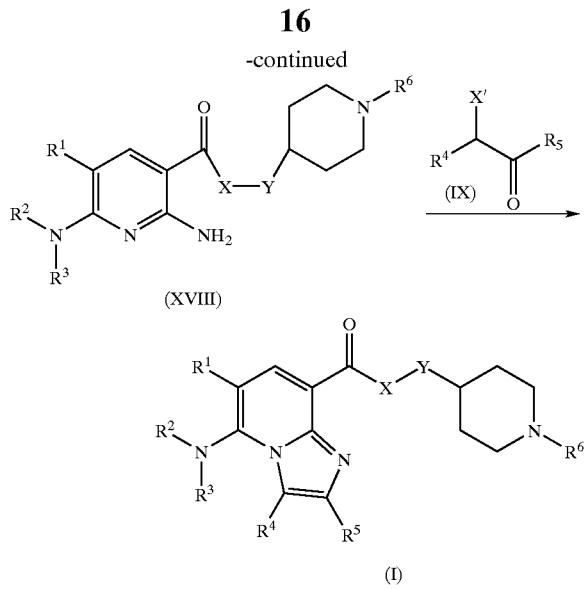

In Scheme 7, a pyridine compound (XV) may be treated with n-BuLi followed by an aldehyde compound (XIX) wherein PG is a suitable protecting group, for example, methoxycarbonyl, ethoxycarbonyl, tert-butoxycarbonyl (Boc), benzyloxycarbonyl(Z), or the like, to obtain a compound (XVI). This reaction can be carried out in a suitable reaction-inert solvent. Suitable solvents include, for example, ethers such as tetrahydrofuran, 1,2-dimethoxyethane, diethyl ether, diisopropyl ether, diphenyl ether and 1,4-dioxane. This reaction may be carried out at a temperature in the range from −100 to 100° C., usually from −100° C. to 80° C. for 30 minutes to 24 hours, usually 30 minutes to 10 hours. The compound (XVI) may be treated with an oxidizing agent, for example, pyridinium chlorochromate(PCC), pyridinium dichromate(PDC), manganese dioxide, tetrapropylammonium perruthenate(TPAP), or the like, to obtain a compound (XVII). Also, the compound (XVI) may be subjected to a dimethylsulfoxide oxidation to obtain a compound (XVII). This reaction can be carried out in a suitable reaction-inert solvent such as halogenated hydrocarbons such as chloroform, dichloroethane and 1,2-dichloroethane. This reaction may be carried out at a temperature in the range from 0 to 80° C., usually from 25 to 70° C. for 5 minutes to 24 hours, usually 15 minutes to 8 hours. Then, the compound (XVII) may be subject to amination according to the similar procedure described in Scheme 2. The obtained amino compound may be subjected to deprotection of an amino-protecting group, to obtain a compound (VIII). The deprotection may be carried out by a number of standard procedures known to those skilled in the art (e.g., "Protection for the Hydroxy Group and the Amino Group", in *Protective Groups in Organic Synthesis*, 2nd Edition, T. W. Greene and P. G. M. Wuts, Ed., John Wiley and Sons, Inc. 1991, pp. 10–142, 309–405). Then, alkylation of amino group in piperidine ring may be carried out under the conventional conditions. The compound may be treated with appropriate alkyl halides ($R^6$—Z) in the presence of a base such as diisopropylethylamine, triethylamine, pyridine, lutidine, potassium carbonate, sodium bicarbonate, sodium carbonate or the like, in a reaction inert solvent such as dichloromethane, THF or DMF at about 0° C. to about 100°

C. for about 5 minutes to about 48 hours. Then, when R¹ is halo, the obtained compound may be subjected to halogenation and deprotection. These reactions may be carried out under the similar conditions described in Scheme 2. Compounds (I) may be prepared by reacting a compound (XVIII) with the compound (IX) under appropriate conditions. This reaction can be carried out in a suitable reaction-inert solvent such as methanol. This reaction may be carried out at a temperature in the range from 25 to 65° C., usually from 50° C. to 65° C. for 30 minutes to 48 hours, usually 30 minutes to 12 hours.

Scheme 8:

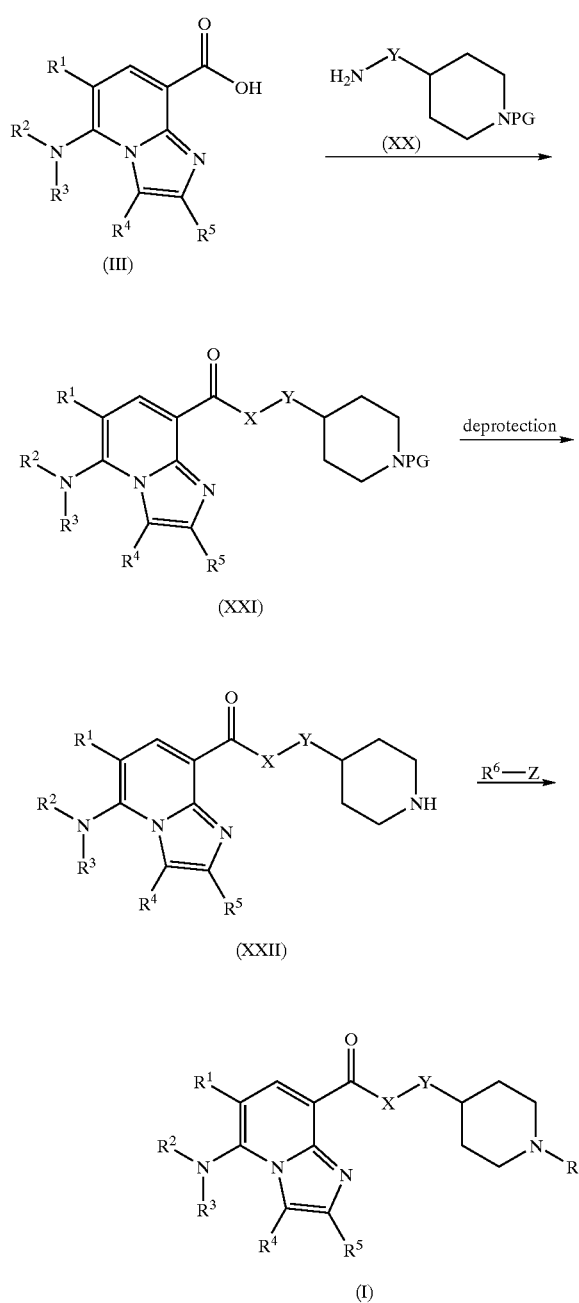

wherein R' is $C_{1-3}$ alkyl; X is NH; and all other symbols are as already defined)

In Scheme 8, the carboxylic acid compound (III) may be coupled with the amine compound (XX) to give an imidazopyridine compound (XXI) wherein X is NH. Then, the compound (XXI) may be subjected to deprotection of the protecting group of nitrogen atom in the piperidinering, followed by alkylation to afford an imidazopyridine compound (I) wherein X is NH.

The coupling reaction may be carried out in the presence of a suitable condensation agent in a reaction-inert solvent. Suitable condensation agents include 1,1'-carbonyldiimidazole (CDI), diisopropylcarbodiimide (DIC), dicyclohexylcarbodiimide (DCC), water soluble carbodiumide (WSC), 2-ethoxy-N-ethoxycarbonyl-1,2-dihydroquinoline, benzotriazol-1-yloxy-tris (dimethylamino) phosphonium hexafluorophosphate (BOP), diethyl azodicarboxylatetriphenylphosphine, diethylcyanophosphonate (DEPC), diphenylphosphorylazide (DPPA), bromotripyrrolidino phosphonium hexafluorophosphate (PyBrop[trademark]), bis(2-oxo-3-oxazolidinyl) phosphinic chloride (BOPCl), benzotriazole-1-yl-oxy-tris-pyrrolidino-phosphonium hexafluorophosphate (PyBOP), 2-(1-H-benzotriazole-1-yl)-1,1,3,3,-tetramethyluronium hexafluorophosphate (HBTU) and ethyl chloroformate. Suitable reaction-inert solvents include aqueous or non-aqueous organic solvents such as tetrahydrofuran, N,N-dimethylforrnamide (DMF), dioxane, acetone, dimethoxyethane and acetonitrile; and halogenated hydrocarbons such as chloroform, dichloromethane and dichloroethane (preferably dichloromethane). This reaction may be carried out at a temperature in the range from −20 to 80° C., usually from 0° C. to 30° C. for 30 minutes to 100 hours, usually 5 hours to 24 hours.

The obtained amino compound may be subjected to deprotection of an amino-protecting group, to obtain a compound (XXII). The deprotection may be carried out by a number of standard procedures known to those skilled in the art (e.g., "Protection for the Hydroxy Group and the Amino Group", in *Protective Groups in Organic Synthesis*, 2nd Edition, T. W. Greene and P. G. M. Wuts, Ed., John Wiley and Sons, Inc. 1991, pp. 10–142, 309–405). Then, alkylation of amino group in piperidine ring may be carried out under the conventional conditions. The compound may be treated with appropriate alkyl halides(R⁶—Z) in the presence of a base such as diisopropylethylamine, triethylamine, pyridine, lutidine, potassium carbonate, sodium bicarbonate, sodium carbonate or the like, in a reaction inert solvent such as dichrolomethane, THF or DMF at about 0° C. to about 100° C. for about 5 minutes to about 48 hours.

Scheme 9:

The carboxylate compounds (II'), wherein X' is may be prepared in the following reaction steps.

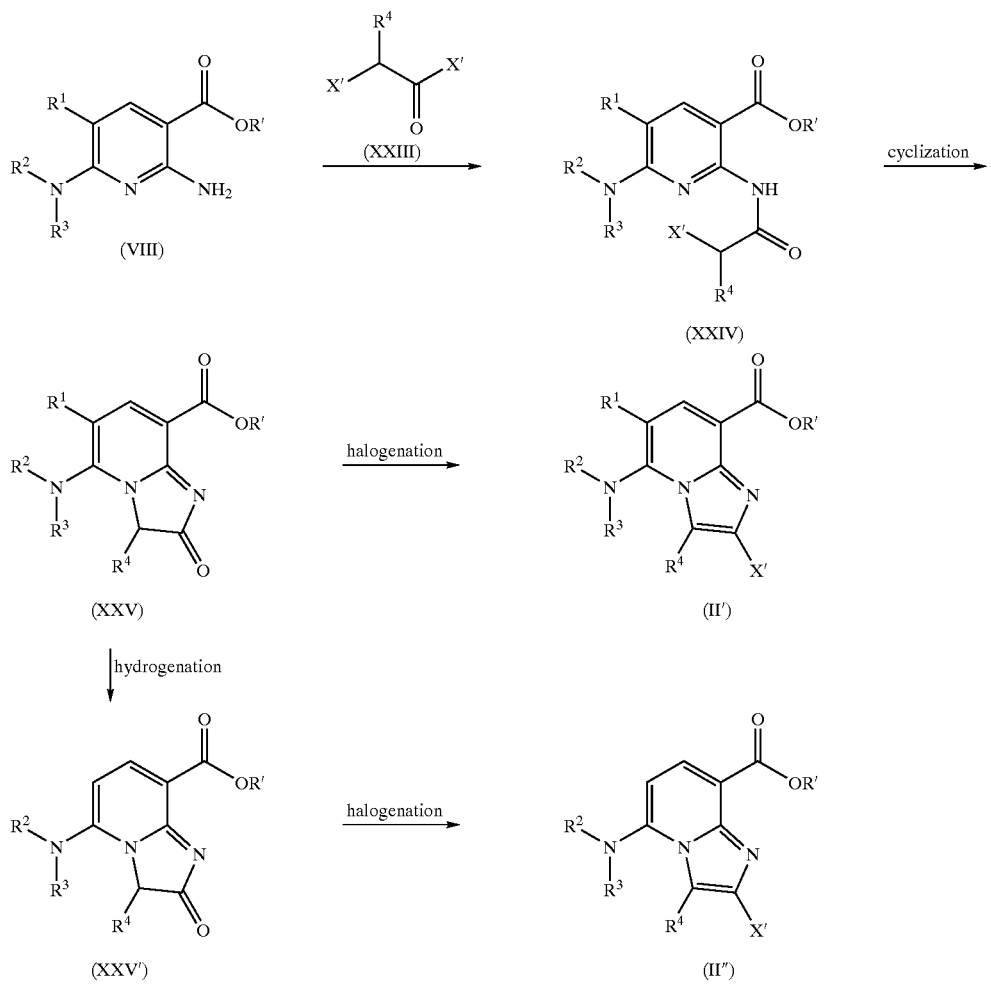

In Scheme 9, the compound (VIII) may be reacted with a compound (XXIII) wherein X' is halogen, to obtain a compound (XXIV). This reaction may be carried out in the presence of a base. Example of such bases include: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride. This reaction can be carried out in a suitable reaction-inert solvent such as tetrahydrofuran (THF), dimethylformamide (DMF), acetonitrile, dichloromethane, dimethylsulfoxide (DMSO), methylethylketone, methanol, ethanol, propanol and butanol at a temperature in the range from −50 to 100° C., usually from −10° C. to 50° C. for 1 minute to 24 hours, usually 5 minutes to 10 hours. The resulting compound (II) and the compound (XXIV) may be subjected to a cylization to obtain the compound (XXV). This reaction can be carried out in a suitable reaction-inert solvent such as tetrahydrofuran, dimethylformamide (DMF), acetonitrile, dichloromethane, dichloroethane, dimethylsulfoxide (DMSO), methylethylketone, methanol, ethanol, propanol, butanol, iso-butanol, sec-butanol and tert-butanol at a temperature in the range from −50 to 250° C., usually from 0° C. to 200° C. for 1 hour to 100 hours, usually 10 hours to 80 hours.

Then, when $R^5$ is halo, the obtained compound (XXV) may be subjected to halogenation. The compound (XXV) may be treated with phosphorus oxyhalide (POX'$_3$) to provide halogenated compound (II'). This reaction may be carried out at a temperature in the range from 0 to 200° C., usually from 20° C. to 150° C. for 1 minute to 24 hours, usually 5 minutes to 12 hours. Alternatively, compound (II'') (compound (II') wherein $R^1$ is hydrogen) can be prepared by subjecting a compound (XXV) wherein $R^1$ is halo, to catalytic hydrogenation followed by halogenation. The catalytic hydrogenation can be carried out in the presence of hydrogen or hydrogen source such as ammonium formate or triethylsilane and a suitable metal containing catalysts such as palladium, platinum, nickel, platinum oxide and rhodium in a suitable reaction-inert solvent such as methanol. The preferred catalyst is palladium on carbon. This hydrogenation can be carried out at a temperature in the range from 20 to 100° C., usually from 25° C. to 80° C. for 5 minutes to 48 hours, usually 30 minutes to 2 hours. The halogenation of compound (XXV') may be carried out under the same condition as described in the preparation of compound (II').

In addition, starting compounds of formula (V) are known or may be prepared from a known compound according to procedures known to those skilled in the art.

Scheme 10:

An amino compound (XXX) wherein $R^a$ and $R^b$ are $C_{1-4}$ alkyl and $R^c$ is $C_{1-6}$ alkyl, may be prepared in the following reaction steps.

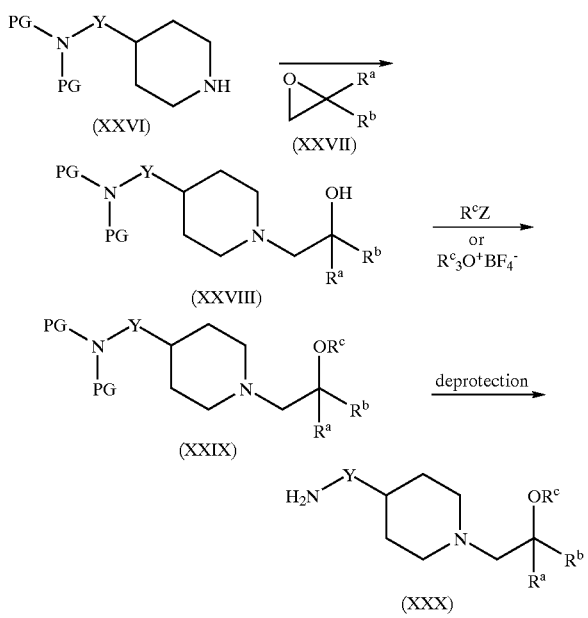

In scheme 10, piperidine compound (XXVI) may be reacted with an epoxide compound (XXVII) to obtain a hydroxy compound (XXVIII). This reaction can be carried out in a suitable reaction-inert solvent such as tetrahydrofuran, dimethylformamide (DMF), acetonitrile, dichloromethane, dichloroethane, dimethylsulfoxide (DMSO), methylethylketone, methanol, ethanol, propanol, butanol, iso-butanol, sec-butanol and tert-butanol at a temperature in the range from −50 to 250° C., usually from 0° C. to 200° C. for 30 minutes to 100 hours, usually 1 hour to 80 hours. This reaction may be carried out in the presense of a methal halide sucha as sodium iodide, potassium iodide and lithium iodide. The conversion of hydroxy compound (XXVIII) to an alkoxy compound (XXIX) may be carried out under the conventional method. The alkylation of a hydroxy group may be carried out under the conventional conditions. The compound may be treated with appropriate alkyl halides($R^6$—Z) in the presence of a base such as sodium methoxide, sodium ethoxide, potassium tert-butoxide, sodium hydride or potassium hydride, or the like, in a reaction inert solvent such as diethyl ether, dimthoxyethane, DMSO, THF or DMF at about 0° C. to about 200° C., usually from 0° C. to 200° C., for about 5 minutes to about 100 hours, usually 1 hour to 80 hours. Alternatively, hydroxy compound (XXVIII) may be treated with $R^cO^+BF_4^-$ to provide the compound (XXIX). This reaction can be carried out in a suitable reaction-inert solvent such as dichloromethane, dichloroethane, benzene, toluene and nitromethane at a temperature in the range from −50 to 200° C., usually from 0° C. to 100° C. for 30 minutes to 100 hours, usually 1 hour to 80 hours. The obtained compound (XXIX) may be subjected to deprotection of an amino-protecting group, to obtain a compound (XXX). The deprotection may be carried out by a number of standard procedures known to those skilled in the art (e.g., "Protection for the Hydroxy Group and the Amino Group", in *Protective Groups in Organic Synthesis*, 2nd Edition, T. W. Greene and P. G. M. Wuts, Ed., John Wiley and Sons, Inc. 1991, pp. 10–142, 309–405).

Scheme 11:

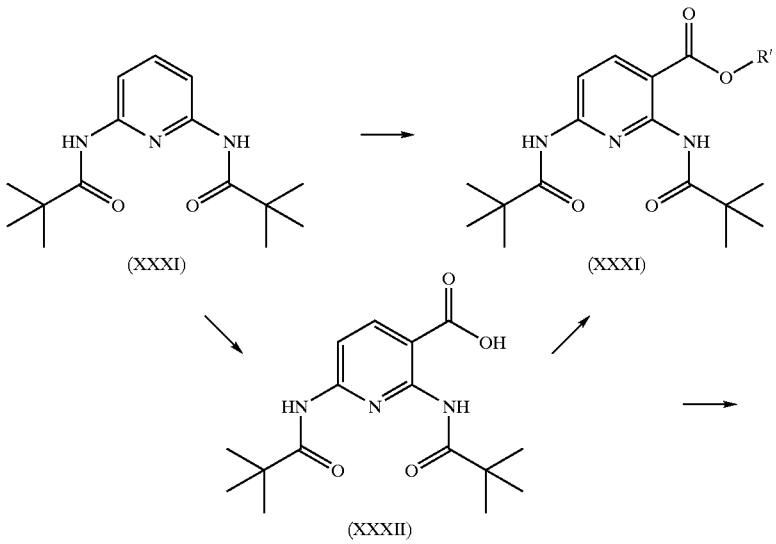

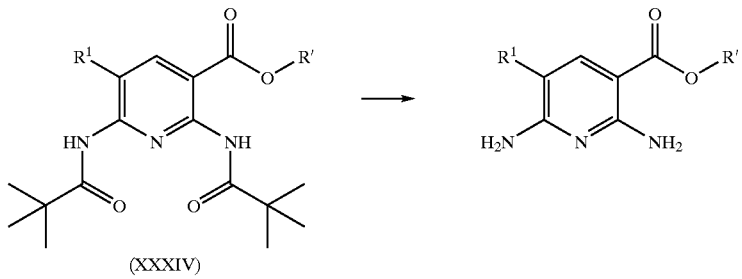

(XXXIV)

The nicotinate compounds (XXXV) may be prepared in the following reaction steps.

In scheme 11, a pyridine compound (XXXI) may be treated with n-BuLi followed by R'COZ or R'COR' wherein R' is $C_{1-3}$ alkyl or benzyl and Z is halogen, to obtain a compound (XXXIII). This reaction can be carried out in a suitable reaction-inert solvent. Suitable solvents include, for example, ethers such as tetrahydrofuran, 1,2-dimethoxyethane, diethyl ether, diisopropyl ether, diphenyl ether and 1,4-dioxane. This reaction may be carried out at a temperature in the range from −100 to 50° C., usually from −100 to 20° C. for 5 minutes to 24 hours, usually 15 minutes to 8 hours. Alternatively, the compound (XXXIII) may be prerpareed from the pyridine compound (XXXI) by carboxylation followed by esterification. The pyridine compound (XXXI) may be treated with n-BuLi followed by carbondioxide (gas or dry ice) to obtain a carboxylic acid compound (XXXII). This reaction can be carried out in a suitable reaction-inert solvent. Suitable solvents include, for example, ethers such as tetrahydrofuran, 1,2-dimethoxyethane, diethyl ether, diisopropyl ether, diphenyl ether and 1,4-dioxane. This reaction may be carried out at a temperature in the range from −100 to 50° C., usually from −100 to 20° C. for 5 minutes to 24 hours, usually 15 minutes to 8 hours. The compound (XXXII) may be subjected to esterification to obtain the compound (XXXIII). The esterification may be carried out by a number of standard procedures known to those skilled in the art (e.g., *Protective Groups in Organic Synthesis*, Third eddition. ed. T. W. Green and P. G. M. Wuts, Wiley-Interscience., pp 373–377.). Typical esterificaion can be carried out with a suitable $C_{1-3}$ alkylhalide or benzylhalide in the presense of a base in a suitable reaction-inert solvent. Suitable solvents include, for example, ethers such as tetrahydrofuran, 1,2-dimethoxyethane, diethyl ether, diisopropyl ether, diphenyl ether, DMF, DMSO, R'OH and 1,4-dioxane. Suitable bases include, for example, $K_2CO_3$, $Cs_2CO3$, $NaHCO_3$ and DBU. This reaction may be carried out at a temperature in the range from −100 to 200° C., usually from −10 to 100° C. for 1 to 72 hours, usually 2 to 60 hours. The esterification also carried out with trimethylsilyldiazomethane in a suitable reaction-inert solvent. Suitable solvents include, for example, methanol, benzene and toluene. This reaction may be carried out at a temperature in the range from −100 to 200° C., usually from −10 to 100° C. for 1 minute to 72 hours, usually 0.5 to 60 hours. The esterification also carried out with diazomethane in a suitable reaction-inert solvent. Suitable solvents include, for example, diethyl ether. This reaction may be carried out at a temperature in the range from −100 to 200° C., usually from −50 to 100° C. for 1 minute to 72 hours, usually 0.5 to 60 hours. Alternatively, the esterification may be carried out with R'OH, in the presense of a coupling agent and a tertiaryamine in a suitable solvent. Suitable coupling agents include, for example, DCC, WSC, diisoproopylcyanophosphonate (DIPC), BOPCl and 2,4,6-trichlorobenzoic acid chloride. Suitable tertiaryamines include, for example, i-$Pr_2$NEt, $Et_3$N. Suitable solvents include, for example, DMF, THF, diethyl ether, DME, dichloromethane and DCE. This reaction may be carried out at a temperature in the range from −100 to 200° C., usually from −50 to 100° C. for 1 minute to 100 hours, usually 0.5 to 80 hours. When $R^1$ is halo, the compound (XXXIII) can be treated with halogen or N-halogenated succimide or SELECTFLUOR(trademark) under appropriate conditions, to obtain a compound (XXXIV) wherein $R^1$ is halo. This reaction can be carried out in a suitable reaction-inert solvent such as carboxylic acids (e.g., acetic acid, propionic acid and butylic acid); halogenated hydrocarbons such as chloroform, dichloroethane and 1,2-dichloroethane; amides such as N,N-dimethylformamide and hexamethylphospholictriamide; sulfoxides such as dimethyl sulfoxide; acetonitrile; benzene, toluene, xylene; and pyridine. This reaction may be carried out at a temperature in the range from 0 to 80° C., usually from 25 to 70° C. for 5 minutes to 24 hours, usually 15 minutes to 8 hours. Then, the compound (XXXIV) may be subject to deprotection of an amino-protecting group, to obtain a compound (XXXV). The deprotection may be carried out in the presence of base (e.g., potassium tert-butoxide, sodium ethoxide and sodium hydroxide) or acids (e.g., hydrochloric acid and sulfuric acid). The deprotection can be carried out in a suitable reaction-inert solvent such as methanol at a temperature in the range from 25 to 80° C., usually from 50 to 65° C. for 10 minutes to 24 hours, usually 30 minutes to 10 hours.

In addition, starting compound of formula (XXXI) is known or may be prepared from a known compound according to procedures known to those skilled in the art, for example, *J. Am. Chem. Soc.* (1986), 108(12), 3310–18.

The present invention includes salt forms of the compounds (I) as obtained above. Insofar as the imidazopyridine compounds of this invention are basic compounds, they are capable of forming a wide variety of different salts with various inorganic or organic acids.

The acids which are used to prepare the pharmaceutically acceptable acid addition salts of the aforementioned imidazopyridine base compounds of formula (I) are those which form non-toxic acid addition salts, i.e., salts containing pharmaceutically acceptable anions, such as the chloride, bromide, iodide, nitrate, sulfate or bisulfate, phosphate or acid phosphate, acetate, lactate, citrate or acid citrate, tartrate or bi-tartrate, succinate, malate, fumarate, gluconate, saccharate, benzoate, methanesulfonate, ethanesulfonate, benzenesulfonate, p-toluenesulfonate and pamoate (i.e., 1.1'-methylene-bis-(2-hydroxy-3-naphthoate). The acid addition salts can be prepared by conventional procedures.

The compounds of formula (I) of this invention may contain one or more asymmetric centers. Thus, the compounds can exist in separated (+)- and (−)-optically active forms, as well as in the racemic form thereof. The present invention includes all such forms within its scope. Individual isomers can be obtained by known methods, such as optically selective reaction or chromatographic separation in the preparation of the final product or its intermediate.

In addition, when the compounds of this invention form hydrates or solvates they are also within the scope of this invention.

The imidazopyridine compounds of this invention have 5-HT$_4$ receptor binding activity (e.g., agonist or antagonist activities), and thus are useful for the treatment or prevention of gastroesophageal reflux disease, gastrointestinal disease, gastric motility disorder, upper gut motility disorder, non-ulcer dyspepsia, Functional dyspepsia, irritable bowel syndrome, constipation, dyspepsia, esophagitis, gastroesophageral disease, nausea, central nervous system disease, alzheimers disease, cognitive disorder, emesis, migraine, neurological disease, pain, ischaemic stroke, anxiety, cardiovascular disorders such as cardiac failure and heart arryhthmia, or the like in mammalian, especially human.

The compounds of the invention may advantageously be employed in combination with one or more other therapeutic ingredients selected from an antibiotic, anti-fungal and antiviral agent.

Method for Assessing Biological Activities

The 5-HT$_4$ receptor binding affinity of the compounds of this invention are determined by the following procedures.
Membrane Preparation Pig heads were supplied from an abattoir. Striatal tissues were dissected, weighed and homogenized in 15 volumes of 50 mM ice-cold HEPES (pH 7.5) in a Polytron homogenizer (30 sec at full speed). Suspension was centrifuged at 48,000 g and 4° C. for 15 min. The resulting pellet was resuspended in an appropriate volume of 50 mM ice-cold HEPES, dispensed into aliquots and stored at −80° C. until use.

Bovine heads were also supplied from an abattoir. Striatal tissues were dissected, weighed and homogenized in 20 volumes of 50 mM ice-cold Tris-HCl (pH 7.4) in a Polytron homogenizer (30 sec at full speed). Suspension was centrifuged at 20,000 g and 4° C. for 30 min. The resulting pellet was resuspended in 15 volumes of 50 mM ice-cold Tris-HCl, homegenized and centrifuged again in the same way. The final pellet was resuspended in an appropriate volume of 50 mM Tris-HCl, dispensed into aliquots and stored at −80° C. until use.

Cerebral cortical tissues were removed from male Sprague-Dawley (SD) rats (Japan SLC), weighed and placed in 10 volumes of 50 mM ice-cold Tris-HCl (pH 7.5). This was homogenized in a Polytron homogenizer (30 sec at full speed) and subsequently centrifuged at 48,000 g and 4° C. for 15 min. The resulting pellet was resuspended in 50 mM ice-cold Tris-HCl, homegenized and centrifuged again in the same way. The final pellet was resuspended in an appropriate volume of 50 mM Tris-HCl, dispensed into aliquots and stored at −80° C. until use.

The protein concentrations of homogenates were determined by Bradford method or BCA protein method (Pierce) with BSA as a standard.
Binding Assays Affinity of compounds for pig or bovine 5-HT4 and rat 5-HT3 receptors were assessed with using radiolabeled specific ligands, GR 113808 ({1-[2-(methylsulfonyl)ethyl]-4-piperidinyl}[methyl-$^3$H]-1H-indole-3-carboxylate) and BRL 43694 (1-Methyl-N-(9-[methyl-$^3$H]-9-azabicyclo[3.3.1]non-3-yl)-1H-indazole-3-caboxamide). Compounds were incubated with 25–100 pM of [$^3$H]-GR 113808 (Amersham) and 0.6–1 mg protein of pig or bovine striatal membranes suspended in a final volume of 0.8–1 ml of 50 mM Tris-HCl (pH 7.5). Nonspecific binding was determined with 10–50 μM 5-HT. The binding of 0.3 nM [$^3$H]-BRL 43694 (NEN) was measured using 400 μg protein of rat cortical membranes suspended in a final volume of 500 μl of 50 mM Tris-HCl (pH 7.5). Nonspecific binding was determined with 10 μM 5-HT.

The plates were incubated at room temperature on a plate shaker for 30 min. The assays were stopped by rapid filtration using a Brandell cell harvester through Wallac-B filters pre-soaked in 0.2% poly(ethylenimine) at 4° C. for 60–90 min. The filters were washed three times with 1 ml of ice-cold 50 mM HEPES, and were dried in a microwave or at room temperature. They were bagged and heated with meltilex scintillant (Wallac) or soaked in BetaplateScint (Wallac). Receptor-bound radioactivity was quantified using Big-spot counter, Betaplate counter (Wallac) or LS counter (Packard).
Human 5-HT4 Binding Human 5-HT$_{4(d)}$ transfected HEK293 cells were prepared and grown in-house. The collected cells were suspended in 50 mM HEPES (pH 7.4 at 4° C.) supplemented with protease inhibitor cocktail (Boehringer, 1:1000 dilution) and homogenized using a hand held Polytron PT 1200 disrupter set at full power for 30 sec on ice. The homogenates were centrifuged at 40,000×g at 4° C. for 30 min. The pellets were then resuspended in 50 mM HEPES (pH 7.4 at 4° C.) and centrifuged once more in the same manner. The final pellets were resuspended in an appropriate volume of 50 mM HEPES (pH 7.4 at 25° C.), homogenized, aliquoted and stored at −80° C. until use. An aliquot of membrane fractions was used for protein concentration determination using BCA protein assay kit (PIERCE) and ARVOsx plate reader (Wallac).

For the binding experiments, 25 μl of test compounds were incubated with 25 μl of [$^3$H]-GR113808 (Amersham, final 0.2 nM) and 150 μl of membrane homogenate and WGA-SPA beads (Amersham) suspension solutions (10 μg protein and 1 mg SPA beads/well) for 60 minutes at room temperature. Nonspecific binding was determined by 1 μM GR113808 (Tocris) at the final concentration. Incubation was terminated by centrifugation at 1000 rpm. Receptor-bound radioactivity was quantified by counting with Micro-Beta plate counter (Wallac).

All compounds prepared in the working examples as described below were tested by this method, and they showed IC$_{50}$ values from 0.5 nM to 150 nM with respect to inhibition of binding at the 5-HT$_4$ receptor.
Functional Assay:

The presence of 5-HT$_4$ receptors in the rat oesophagus and the ability to demonstrate partial agonism in the TMM preparation are reported in the literature (See G. S. Baxter et al. Naunyn-Schmiedeberg's Arch Pharmacol (1991) 343: 439–446; M. Yukiko et al. JPET (1997) 283: 1000–1008; and J. J. Reeves et al. Br. J. Pharmacol. (1991) 103: 1067–1072). More specifically, partial agonist activity can be measured according to the following procedures.

Male SD rats (Charles River) weighing 250–350 g were stunned and then killed by cervical dislocation. The oesophagus was dissected from immediately proximal to the stomach (including piece of stomach to mark distal end) up to the level of the trachea and then placed in fresh Krebs' solution.

The outer skeletal muscle layer was removed in one go by peeling it away from the underlying smooth muscle layer using forceps (stomach to tracheal direction). The remaining inner tube of smooth muscle was known as the TMM. This was trimmed to 2 cm from the original 'stomach-end' and the rest discarded.

The TMMs were mounted as whole 'open' tubes in longitudinal orientation in 5 ml organ baths filled with warm (32° C.) aerated Krebs. Tissues were placed under an initial tension of 750 mg and allowed to equilibrate for 60 minutes. The tissues were re-tensioned twice at 15 minute intervals during the equilibration period. The pump flow rate was set to 2 ml/min during this time.

Following equilibration, the pump was switched off. The tissues were exposed to 1 $\mu$M carbachol and contracted and reached a steady contractile plateau within 15 minutes. Tissues were then subject to 1 $\mu$M 5-HT (this was to prime the tissues). The tissues relaxed in response to 5-HT fairly rapidly—within 1 minute. As soon as maximal relaxation has occurred and a measurement taken, the tissues were washed at maximum rate (66 ml/min) for at least 1 minute and until the original baseline (pre-carbachol and 5-HT) has returned (usually, the baseline drops below the original one following initial equilibration). The pump flow rate was reduced to 2 ml/min and the tissues left for 60 minutes.

A cumulative concentration-effect-curve (CEC) to 5-HT was constructed across the range 0.1 nM to 1 $\mu$M, in half-log unit increments (5-HT curve 1 for data analysis). Contact time between doses was 3 minutes or until plateau established. Tissues responded quicker as concentration of 5-HT in the bath increases. At the end of the curve, the tissues were washed (at maximum rate) as soon as possible to avoid desensitisation of receptors. Pump rate was reduced to 2 ml/min and the tissues left for 60 minutes.

A second CEC was carried out—either to 5-HT (for time control tissues), another 5-HT$_4$ agonist (standard) or a test compound (curve 2 for data analysis). Contact time varied for other 5-HT$_4$ agonists and test compounds and was tailored according to the tissues' individual responses to each particular agent. In tissues exposed to a test compound, a high concentration (1 $\mu$M) of a 5-HT$_4$ antagonist (SB 203,186: 1H-Indole-3-carboxylic acid, 2-(1-piperidinyl) ethyl ester, Tocris) was added to the bath following the last concentration of test compound. This was to see if any agonist-induced relaxation (if present) could be reversed. SB 203,186 reversed 5-HT induced relaxation, restoring the tissue's original degree of carbachol-induced tone.

Agonist activity of test compounds was confirmed by pre-incubating tissues with 100 nM standard 5HT$_4$ antagonist such as SB 203,186. SB 203,186 was added to the bath 5 minutes before the addition of carbachol prior to curve 2. Tissues must be 'paired' for data analysis i.e. the test compound in the absence of SB 203,186 in one tissue was compared with the test compound in the presence of SB 203,186 in a separate tissue. It was not possible to carry out a curve 3 i.e. 5-HT curve 1, followed by the test compound curve 2 (−SB 203,186), followed by the test compound curve 3 (+SB 203,186).

Agonist-induced cAMP Elevation in Human 5-HT$_{4(d)}$ Transfected HEK293 Cells

Human 5-HT$_{4(d)}$ transfected HEK293 cells were established in-house. The cells were grown at 37° C. and 5% CO$_2$ in DMEM supplemented with 10% FCS, 20 mM HEPES (pH 7.4), 200 $\mu$g/ml hygromycin B (Gibco), 100 units/ml penicillin and 100 $\mu$g/ml streptomycin.

The cells were grown to 60–80% confluence. On the previous day before treatment with compounds dialyzed FCS (Gibco) was substituted for normal and the cells were incubated overnight.

Compounds were prepared in 96-well plates (12.5 $\mu$l/well). The cells were harvested with PBS/1 mM EDTA, centrifuged and washed with PBS. At the beginning of the assay, cell pellet was resuspended in DMEM supplemented with 20 mM HEPES, 10 $\mu$M pargyline (Sigma) and 1 mM 3-isobutyl-1-methylxanthine (Sigma) at the concentration of $1.6 \times 10^5$ cells/ml and left for 15 minutes at room temperature. The reaction was initiated by addition of the cells into plates (12.5 $\mu$l/well). After incubation for 15 minutes at room temperature, 1% Triton X-100 was added to stop the reaction (25 $\mu$l/well) and the plates were left for 30 minutes at room temperature. Homogenous time-resolved fluorescence-based cAMP (Schering) detection was made according to the manufacturer's instruction. ARVOsx multilabel counter (Wallac) was used to measure HTRF (excitation 320 nm, emission 665 nm/620 nm, delay time 50 $\mu$s, window time 400 $\mu$s).

Data was analyzed based on the ratio of fluorescence intensity of each well at 620 nm and 665 nm followed by cAMP quantification using cAMP standard curve. Enhancement of cAMP production elicited by each compound was normalized to the amount of cAMP produced by 1000 nM serotonin (Sigma).

According to the procedures as shown above, the compounds prepared in Examples 1 to 30 were identified as 5HT$_4$ agonists. Introducing an amino group to 5-position of imidazopyridine ring contributed to this agonist activity.

The imidazopyridine compounds of formula (I) of this invention can be administered via either the oral, parenteral or topical routes to mammals. In general, these compounds are most desirably administered to humans in doses ranging from 0.3 mg to 750 mg per day, preferably from 10 mg to 500 mg per day, although variations will necessarily occur depending upon the weight and condition of the subject being treated, the disease state being treated and the particular route of administration chosen. However, for example, a dosage level that is in the range of from 0.06 mg to 2 mg per kg of body weight per day is most desirably employed for treatment of inflammation.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral-pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath temperature of up to 60° C.; reactions were monitored by thin layer chromatography (tlc) and reaction times are given for illustration only; melting points (m.p.) given are uncorrected (polymorphism may result in different melting points); the structure and purity of all isolated compounds were assured by at least one of the following techniques: tlc (Merck silica gel 60 $F_{254}$ precoated TLC plates or Merck $NH_2$ $F_{254s}$ precoated HPTLC plates), mass spectrometry, nuclear magnetic resonance (NMR), infrared red absorption spectra (IR) or microanalysis. Yields are given for illustrative purposes only. Flash column chromatography was carried out using Merck silica gel 60 (230–400 mesh ASTM) or Fuji Silysia Chromatorex® DU3050 (Amino Type, 30~50 μm). Low-resolution mass spectral data (EI) were obtained on a Automass 120 (JEOL) mass spectrometer. Low-resolution mass spectral data (ESI) were obtained on a Quattro II (Micromass) mass spectrometer. NMR data was determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br.=broad, etc. IR spectra were measured by a Shimazu infrared spectrometer (IR-470). Optical rotations were measured using a JASCO DIP-370 Digital Polarimeter (Japan Spectroscopic CO, Ltd.). Chemical symbols have their usual meanings; b.p. (boiling point), m.p. (melting point), l (liter(s)), ml (milliliter (s)), g (gram(s)), mg(milligram(s)), mol (moles), mmol (millimoles), eq. (equivalent(s)).

Example 1

5-Amino-N-[(1-butil-4-piperidinyl)methyl]-6-chloroimidazo[1,2-a]pyridine-8-carboxamide

METHOD A:

Step 1. Ethyl 2-Amino-6-[(2,2-dimethylpropanoyl)amino]nicotinate

To a stirred solution of ethyl 6-[(2,2-dimethylpropanoyl)amino]-2-fluoronicotinate (M. C. Coldwell et al., *Bioorg. Med. Chem. Lett.*, 1995, 39, 5, 1.5 g, 5.59 mmol) was added 25% aqueous ammonia (4 mL) and the mixture was heated in a sealed tube at 70° C. for 4.5 h. After cooling to room temperature, water was added and the mixture was extracted with ethyl acetate. The separated organic layer was concentrated in vacuo and the residue was chromatographed on a column of silica gel eluting with ethyl acetate/pentane (1:6 to 1:2) to give 810 mg (55%) of the title compound as a white solid.

MS (TSP+) m/z: 266 (M+H). $^1$H-NMR (CDCl$_3$) δ: 1.35 (9H, s), 1.36 (3H, t), 4.30 (2H, q), 7.54 (1H, d), 7.80 (1H, br s), 8.12 (1H, d). A signal due to NH2 was not observed.

Step 2. Ethyl 2-Amino-5-chloro-6-[(2,2-dimethylpropanoyl)amino]nicotinate

To a solution of ethyl 2-amino-6-[(2,2-dimethylpropanoyl)amino]nicotinate (EXAMPLE 1, METHOD A, Step 1, 805 mg, 3.03 mmol) in acetic acid (15 ml) was added a solution of chlorine in acetic acid (0.89 M, 8.5 mL, 7.6 mmol), and the mixture was stirred at room temperature for 15 min. The solvent was removed in vacuo. The obtained residue was taken up in ethyl acetate (150 mL) and washed with saturated sodium bicarbonate, dried over magnesium sulfate, and evaporated in vacuo. The residue was chromatographed on a column of silica gel eluting with ethyl acetate/pentane (1:2) to give 685 mg (76%) of the title compound as a white crystal.

MS (TSP+) m/z: 300 (M+H). $^1$H-NMR (CDCl$_3$) δ: 1.35 (9H, s), 1.38 (3H, t, J=7.1 Hz), 4.30 (2H, q, J=7.1 Hz), 8.09 (1H, s), 8.20 (1H, br s). A signal due to NH$_2$ was not observed.

Step 3. Ethyl 5-Amino-6-chloroimidazo[1,2-a]pyridine-8-carboxylate

To a solution of ethyl 2-amino-5-chloro-6-[(2,2-dimethylpropanoyl)amino]nicotinate (EXAMPLE 1, METHOD A, Step 2, 685 mg, 2.12 mmol) in ethanol (10 mL) was added 50% aqueous chloroacetaldehyde (430 μL, 3.4 mmol), and the mixture was refluxed with stirring overnight. The mixture was treated with charcoal and filtered. The filtrate was dry-loaded onto silica gel and chromatographed on a column of silica gel eluting with dichloromethane/methanol/25% aqueous ammonia (97:3:1 to 95:5:0.5) to give 220 mg (40%) of the title compound as a white solid.

MS (TSP+) m/z: 240 (M+H). $^1$H-NMR (DMSO-d$_6$) δ: 1.29 (3H, t, J=7.1 Hz), 4.25 (2H, q, J=6.9 Hz), 7.60 (1H, s) 7.80 (2H, br), 7.89 (1H, s), 8.09 (1H, s).

Step 4. 5-Amino-6-chloroimidazo[1,2-a]pyridine-8-carboxylic Acid

To a stirred solution of ethyl 5-amino-6-chloroimidazo[1,2-a]pyridine-8-carboxylate (EXAMPLE 1, METHOD A, Step 3, 217 mg, 0.91 mmol) in methanol (5 mL) was added 1N aqueous lithium hydroxide (500 μL) and the mixture was stirred overnight at room temperature. The solvent was removed in vacuo and acidified with 1N hydrochloric acid. The resultant precipitate was collected by filtration to give 165 mg (86%) of the title compound as a white solid.

MS (TSP+) m/z: 212 (M+H). $^1$H-NMR (DMSO-d$_6$) δ: 8.00 (1H, s), 8.21 (1H, s), 8.57 (1H, s), 8.90 (2H, br s).

Step 5. 5-Amino-N-[(1-butyl-4-piperidinyl)methyl]-6-chloroimidazo[1,2-a]pyridine-8-carboxamide To a suspension of ethyl 5-amino-6-chloroimidazo[1,2-a]pyridine-8-carboxylate (EXAMPLE 1, METHOD A, Step 4, 159 mg, 0.75 mmol) in N,N-dimethylformamide (5 mL) was added 1,1'-carbonyldiimidazole (134 mg, 0.83 mmol) and the mixture was stirred at room temperature for 20 min. To the resulting solution was added 1-(1-butyl-4-piperidinyl)methanamine dihydrochloride (K. Itoh et al., Eur. *J. Med. Chem. Chim. Ther.*, 1999, 34, 4, 183 mg, 0.75 mmol), followed by triethylamine (314 μL, 2.25 mmol), and the mixture was stirred overnight at room temperature. The mixture was diluted with dichloromethane (150 mL) and washed with water (50 mL×3), dried over magnesium sulfate, decolorized with charcoal and concentrated in vacuo. The obtained residue was chromatographed on a column of silica gel eluting with dichloromethane/methanol/25% aqueous ammonia (95:5:0.5) to give 220 mg (40%) of the title compound as a white solid.

MS (EI) m/z: 364 (M+H). $^1$H-NMR (CDCl$_3$) δ: 0.90 (3H, t, J=7.2 Hz), 1.38–1.22 (2H, m), 1.55–1.38 (3H, m), 1.98–1.60 (6H, m), 2.34–2.26 (2H, m), 2.95 (2H, br d, J=11.1 Hz), 3.45 (2H, t, J=6.3 Hz), 5.20 (2H, br s), 7.46 (1H, s), 7.65 (1H, s), 8.23 (1H, s), 10.09 (1H, s), 10.09 (1H, br). Anal. Calcd. for C$_{18}$H$_{26}$ClN$_5$O.0.1 diethyl ether: C, 59.52; H, 7.33; N, 18.86. Found: C, 59.33; H, 7.37; N, 18.69.

METHOD B: Preparation of Methyl 5-Amino-6-chloroimidazo[1,2-a]pyridine-8-carboxylate.

Step 1, Methyl 2,6Diamino-5-chloronicotinate.

A mixture of ethyl 2-amino-5-chloro-6-[(2,2-dimethylpropanol)amino]nicotinate (EXAMPLE 1, METHOD A, Step 2, 300 mg, 1.0 mmol) and potassium tert-butoxide (337 mg, 3.0 mmol) in methanol (10 mL) was refluxed for 45 min. After evaporation of solvent, water (20 mL) was added. The mixture was extracted with ethyl acetate (10 mL×3), washed with brine (5 mL×3), dried over magnesium sulfate and evaporated. Drying in vacuo gave 177 mg (88%) of the title compound as a cream-white solid.

MS (EI) m/z: 202 (M$^+$). $^1$H-NMR (DMSO-d$_6$) δ: 3.71 (3H, s), 6.77 (2H, br s), 6.94 (2H, br s), 7.72 (1H, s).

Step 2, Methyl 5-Amino-6-chloroimidazo[1,2-a]pyridine-8-carboxylate

A mixture of methyl 2,6-diamino-5-chloronicotinate (EXAMPLE 1, METHOD B, Step 1, 2.0 g, 9.92 mmol) and chloroacetaldehyde (1.2 mL, 10.91 mmol) in methanol (100 mL) was refluxed for 135 min. A further chloroacetaldehyde (1.2 mL, 10.91 mmol) was added and refluxing continued over 21 hours. The solvent was evaporated and the resulting solid co-evaporated with methanol (75 mL×2) prior to drying under vacuum, giving 2.62 g of crude material. The residue was chromatographed on a column of silica gel eluting with dichloromethane/methanol/25% aqueous ammonia (96.5:3.5:0.5 to 93:7:1) to give 1.52 g (68%) of the title compound as an off white powder.

MS (EI) m/z: 225 (M$^+$). $^1$H-NMR (DMSO-d$_6$) δ: 3.35 (3H, s), 7.62 (1H, s), 7.85 (2H, br s), 7.92 (1H, s), 8.13 (1H, s).

Example 2

5-Amino-N-[(1-butyl-4-piperidinyl)methyl]imidazo[1,2-a]pyridine-8-carboxamide

A mixture of 5-amino-N-[(1-butyl-4-piperidinyl)methyl]-6-chloroimidazo[1,2-a]pyridine-8-carboxamide (EXAMPLE 1, METHOD A, Step 5, 70 mg, 0.19 mmol), ammonium formate (120 mg, 1.9 mmol) and 10% palladium on carbon (50 mg) in methanol (5 mL) was stirred at room temperature under nitrogen atmosphere for 2 h. The mixture was filtered through a pad of Celite, and the filtrate was basified with 25% aqueous ammonia. This was chromatographed on a column of silica gel eluting with dichloromethane/methanol/25% aqueous ammonia (90:10:1) to give 40 mg (63%) of the title compound as a gum.

MS (EI) m/z: 330 (M+H). $^1$H-NMR (CDCl$_3$) δ: 0.85 (3H, t), 1.30–1.20 (2H, m), 1.50–1.32 (4H, m), 1.75–1.60 (1H, m), 1.80 (2H, br d), 1.90 (2H, br t), 2.32–2.25 (2H, m), 2.94 (2H, br d), 3.40 (2H, m), 4.79 (2H, br s), 6.18 (1H, d), 7.40 (1H, s), 7.60 (1H, s), 8.14 (1H, d), 10.04 (1H, br s).

Example 3

5-Amino-6-chloro-N-[1-(3-methoxypropyl)-4-piperidinyl]imidazo[1,2-a]pyridine-8-carboxamide To a suspension of the 5-amino-6-chloroimidazo[1,2-a]pyridine-8-carboxylic acid (EXAMPLE 1, METHOD A, Step 4, 210 mg, 0.99 mmol) in N,N-dimethylformamide (5 mL) was added 1,1'-carbonyldiimidazole (177 mg, 1.09 mmol) and stirred at room temperature for 20 min. To this resulting solution was added 1-(3-methoxypropyl)-4-piperidinamine (A. Karasawa et al., WO 9950264, 188 mg, 1.09 mmol) and the mixture was stirred overnight under nitrogen at room temperature. The mixture was concentrated in vacuo, chromatographed on a column of silica gel eluting with dichloromethane/methanol/25% aqueous ammonia (95:5:0.5) to afford a yellow oil, which was dissolved in dichloromethane (300 mL), washed with water (75 mL×3), brine (75 mL) and dried over magnesium sulfate. After treatment with charcoal, removal of solvent gave a cream solid, which was recrystallized from diethyl ether to afford 175 mg (48%) of the title compound as a solid.

MS (TSP+) m/z: 366 (M+H). $^1$H-NMR (CDCl$_3$) δ: 1.80–1.70 (4H, m), 2.05 (2H, br d), 2.21 (2H, dt), 2.42 (2H, t), 2.82 (2H, br d), 3.31 (3H, s), 3.40 (2H, t), 4.10 (1H, m), 5.05 (2H, br s), 7.40 (1H, s), 7.61 (1H, s), 8.21 (1H, s), 10.00 (1H, d). Anal. Calcd. for C$_{17}$H$_{24}$ClN$_5$O$_2$: C, 55.81; H, 6.63; N, 19.13. Found: C, 55.70; H, 6.75; N, 18.65.

Example 4

5-Amino-N-[1-(3-methoxypropyl)-4-piperidinyl]imidazo[1,2-a]pyridine-8-carboxamide The title compound was prepared according to the procedure of EXAMPLE 2 using 5-amino-6-chloro-N-[1-(3-methoxypropyl)-4-piperidinyl]imidazo[1,2-a]pyridine-8-carboxamide (EXAMPLE 3), instead of 5-amino-N-[(1-butyl-4-piperidinyl)methyl]-6-chloroimidazo[1,2-a]pyridine-8-carboxamide.

MS (TSP+) m/z: 332 (M+H). $^1$H-NMR (CDCl$_3$) δ: 1.81–1.60 (4H, m), 2.10 (2H, br d), 2.22 (2H, dt), 2.42 (2H, m), 2.85 (2H, br s), 3.30 (3H, s), 3.45 (2H, t), 4.09 (1H, m), 4.61 (2H, br s), 6.20) 1H, d), 7.40 (1H, s), 7.62 (1H, s), 8.20 (1H, d), 10.13 (1H, br d).

Example 5

5-Amino-N-[(1-butyl-4-piperidinyl)methyl]-6-chloro-2-methylimidazo[1,2-a]pyridine-8-carboxamide Step1. Methyl 5-Amino-6-chloro-2-methylimidazo[1,2-a]pyridine-8-carboxylate and methyl 5-Amino-8-chloro-2-methylimidazo[1,2-a]pyridine-6-carboxylate.

The title compounds were prepared according to the procedure described in the step 2 of EXAMPLE 1

(METHOD B) using bromoacetone instead of chloroacetaldehyde. Methyl 5-amino-6-chloro-2-methylimidazo[1,2-a]pyridine-8-carboxylate.

MS (FAB) m/z: 240 (M+1). $^1$H-NMR (DMSO-d$_6$) δ: 2.34 (3H, s), 3.80 (3H, s), 7.70 (2H, br s), 7.83 (1H, s), 7.85 (1H, s). Methyl 5-amino-8-chloro-2-methylimidazo[1,2-a]pyridine-6-carboxylate.

MS (FAB) m/z: 240 (M+1). $^1$H-NMR (DMSO-d$_6$) δ: 2.34 (3H, s), 3.82 (3H, s), 7.60 (1H, s), 8.02 (1H, s), 8.23 (2H, br s).

Step 2. 5-Amino-6-chloro-2-methylimidazo[1,2-a]pyridine-8-carboxylic Acid.

The title compound was prepared according to the procedure described in the step 4 of EXAMPLE 1 (METHOD A) using methyl 5-amino-6-chloro-2-methylimidazo[1,2-a]pyridine-8-carboxylate (EXAMPLE 5, Step 1) instead of ethyl 5-amino-6-chloroimidazo[1,2-a]pyridine-8-carboxylate.

MS (EI) m/z: 225 (M$^+$). $^1$H-NMR (DMSO-d$_6$) δ: 2.38 (3H, s), 7.88 (1H, s), 7.92 (1H, s), 8.00 (2H, br s). A signal of COOH was not observed.

Step 3. 5-Amino-N-[(1-butyl-4-piperidinyl)methyl]-6-chloro-2-methylimidazol[1,2-a]pyridine-8-carboxamide To a mixture of 5-amino-6-chloro-2-methylimidazo[1,2-a]pyridine-8-carboxylic acid (EXAMPLE 5, Step 2, 50 mg, 0.22 mmol), and 1-(1-butyl-4-piperidinyl)methanamine (42 mg, 0.24 mmol) in N,N-dimethylformamide (2 mL) were added diethyl phosphorocyanidate (37 μL, 0.24 mmol) and triethylamine (34 μL, 0.24 mmol) at 0° C. The mixture was allowed to warm up to room temperature and stirred for 12 h. Water was added to the mixture. The formed solid was collected by filtration and washed with water and ethyl acetate. Purification by preparative thin layer chromatography developing with dichloromethane/methanol (5:1) gave 46 mg (54%) of the title compound as a brown-white solid.

MS (EI) m/z: 377 (M$^+$). m.p.: 188–191° C. IR (KBr) v: 3153, 2927, 2862, 2808, 2773, 1638, 1560, 1547, 1512, 1431, 1321, 1261, 1230, 1145, 718, 662 cm$^{-1}$. $^1$H-NMR (DMSO-d$_6$) δ: 0.86 (3H, t, J=7.2 Hz), 1.50–1.22 (7H, m), 1.69–1.65 (2H, m), 1.85–1.78 (2H, m), 2.22 (2H, m), 2.37 (3H, s), 2.86–2.51 (2H, m), 3.28 (2H, t, J=6.3 Hz), 7.58 (2H, br s), 7.85 (1H, s), 7.87 (1H, s), 9.91 (1H, br t). Anal. Calcd. for C$_{19}$H$_{28}$ClN$_5$O·0.65H$_2$O: C, 58.57; H, 7.58; N, 17.97. Found: C, 58.88; H, 7.72; N, 17.71.

Example 6

5-Amino-6-chloro-2-methyl-N-({1-[3-(methoxy)propyl]-4-piperidinyl}imidazo[1,2-a]pyridine-8-carboxamide The title compound was prepared according to the procedure described in the step 3 of EXAMPLE 5 using 1-[3-(methoxy)propyl]-4-piperidinamine instead of 1-(1-butyl-4-piperidinyl)methanamine.

MS (EI) m/z: 379 (M$^+$). m.p.: 190° C. IR (KBr) v: 3477, 3304, 3148, 2932, 2808, 1636, 1601, 1560, 1545, 1512, 1439, 1381, 1319, 1234,1119 cm$^{-1}$. $^1$H-NMR (DMSO-d$_6$) δ: 1.56–1.45 (2H, m), 1.66 (2H, quint, J=6.9 Hz), 1.92–1.88 (2H, m), 2.21–2.14 (2H, m), 2.34 (2H, t, J=7.4 Hz), 2.38 (3H, s), 2.75–2.65 (2H, m), 3.22 (3H, s), 3.37–3.32 (2H, m), 3.91–3.86 (1H, m), 7.58 (2H, br s), 7.84 (1H, s), 7.87 (1H, d, J=0.9 Hz), 9.99 (1H, d, J=8.1 Hz). Anal. Calcd. for C$_{18}$H$_{26}$ClN$_5$O$_2$: C, 56.91; H, 6.90; N, 18.44. Found: C, 56.87; H, 6.92; N, 18.40.

Example 7

5-Amino-6-chloro-2-methyl-N-({1-[3-(methoxy)propyl]-4-piperidinyl}methyl)imidazo[1,2-a]pyridine-8-carboxamide The title compound was prepared according to the procedure described in the step 3 of EXAMPLE 5 using {1-[3-(methyloxy)propyl]-4-piperidinyl}methylamine* instead of 1-(1-butyl-4-piperidinyl)methanamine.

MS (EI) m/z: 393 (M$^+$). m.p.: 167° C. IR (KBr) v: 3321, 3198, 3061, 2936, 1643, 1628, 1605, 1578, 1562, 1512, 1431, 1323, 1$^2$63, 1123, 1097, 723 cm$^{-1}$. $^1$H-NMR (DMSO-d$_6$) δ: 1.30–1.15 (2H, m), 1.55–1.40 (1H, m), 1.68–1.60 (4H, m), 1.85–1.78 (2H, m), 2.27 (2H, t, J=7.2 Hz), 2.37 (3H, s), 2.83 (2H, m), 3.20 (3H, s), 3.33–3.26 (4H, mn), 7.85 (1H, s), 7.58 (2H, br s), 7.87 (1H, s), 9.91 (1H, t, J=5.4 Hz). Anal. Calcd. for C$_{19}$H$_{28}$ClN$_5$O$_2$·2.5H$_2$O: C, 51.99; H, 7.58; N, 15.95. Found: C, 52.32; H, 7.54; N, 15.85.

* Preparation of {1-[3-(methyloxy)propyl]-4-piperidinyl}methylamine.

Step 1. 1-[3-(Methyloxy)propyl]4-piperidinecarboxamide

A mixture of 4-piperidinecarboxamide (10.6 g, 82.3 mmol), 1-bromo-3-(methyloxy)propane (C. A. Grob and A. Waldner, Helv. Chim. Acta, 1980, 63, 2152–2158, 12.6 g, 82.3 mmol), and potassium carbonate (22.8 g, 165 mmol) in ethanol (60 mL) was refluxed for 23 h. After cooling to room temperature, ethanol was removed in vacuo. Water (500 mL) was added and the water layer was extracted with dichloromethane (300 mL×13). The combined organic layer was dried over magnesium sulfate and concentrated in vacuo to give 8.04 g (49%) of the title compound as a white solid.

MS (ESI) m/z: 201 (M$^+$). $^1$H-NMR (CDCl$_3$) δ: 1.82–1.70 (4H, m), 2.04–1.84 (4H, m), 2.21–2.10 (1H, m), 2.45–2.37 (2H, m), 2.97 (2H, br d, J=11.7 Hz), 3.33 (3H, s), 3.42 (2H, t, J=6.6 Hz), 5.70 (2H, br).

Step 2. {1-[3-(Methyloxy)propyl]4-piperidinyl}methylamine

To a suspension of lithium aluminum hydride (3.32 g, 70.0 mmol) in tetrahydrofuran (200 mL) was added dropwise a solution of 1-[3-(methyloxy)propyl]-4-piperidinecarboxamide (Step 1, 7.00 g, 35.0 mmol) in tetrahydrofuran (50 mL) at 0° C. over 15 min. The mixture was stirred at 0° C. for 30 min and at 40° C. for 1.5 h. After cooling to 0° C., water (3.3 mL), 15% aqueous sodium hydroxide (3.3 mL) and then water (10 mL) were carefully added dropwise. The mixture was filtered through a pad of Celite, which was washed with tetrahydrofuran. The filtrate was concentrated in vacuo to give 6.31 g (97%) of the title compound as a pale yellow oil. Rf value: 0.14 (dichloromethane/methanol/25% ammonia=10/1/0.2).

$^1$H-NMR (CDCl$_3$) δ: 1.32–1.18 (3H, m), 1.97–1.67 (6H, m), 2.39 (2H, dd, J=7.4, 9.7 Hz), 2.57 (2H, d, J=5.6 Hz), 2.94 (2H, d, J=11.7 Hz), 3.33 (3H, s), 3.41 (3H, t, J=6.4 Hz). A signal due to NH$_2$ was not observed.

Example 8

N-[(1-Butylpiperidin-4-yl)methyl]-6-chloro-5-(methylamino)imidazo[1,2-a]pyridine-8-carboxamide Step 1. Ethyl 2-Amino-6-(methylamino)nicotinate A mixture of ethyl 2-[(2,2-dimethylpropanoyl)amino]-6-fluoronicotinate (WO9407859, 2.50 g, 9.32 mmol), 40% methylamine in methanol (10 mL), and tetrahydrofuran (10 mL) was heated overnight at 80° C. in a sealed tube. After cooling to room temperature, the mixture was concentrated in vacuo. The residue was dissolved in dichloromethane (100 mL), and the organic layer was washed with water (50 mL×2), dried over sodium sulfate, and concentrated in vacuo. The residue was triturated with diethyl ether/hexane (1:4, 50 mL), and the formed solid was collected by filtration to give 1.28 g (70%) of the title compound as a white solid. The filtrate was concentrated in vacuo, and the residue was chromatographed on a column of silica gel eluting with ethyl acetate/hexane (1:2) to give 495 mg (27%) of the title compound as a white solid. Rf value: 0.2 (ethyl acetate/hexane, 1:5).

$^1$H-NMR (CDCl$_3$) δ: 1.34 (3H, t, J=7.1 Hz), 2.92 (3H, d, J=5.1 Hz), 4.26 (2H, q, J=7.1 Hz), 4.70 (1H, br), 5.73 (1H, d, J=8.6 Hz), 7.98 (1H, d, J=8.6 Hz), 7.89 (1H, d, J=8.6 Hz). A signal due to NH$_2$ was not observed.

Step 2. Ethyl 2-Amino-5-chloro-6-(methylamino) nicotinate

To a stirred solution of ethyl 2-amino-6-(methylamino) nicotinate (EXAMPLE 8, Step 1, 1.78 g, 9.12 mmol) in N,N-dimethylformamide (18 mL) was added N-chlorosuccinimide (1.27 g, 9.54 mmol), and the mixture was stirred at 80° C. for 2 h. After cooling to room temperature, water (50 mL) was added, and the aqueous layer as extracted with diethyl ether (50 mL×3). The combined organic layer was dried over sodium sulfate, and concentrated in vacuo. The residue was chromatographed on a column of silica gel eluting with ethyl acetate/hexane (1:5) to give 1.95 g (93%) of the title compound as a white solid.

MS (EI) m/z: 229 (M$^+$). $^1$H-NMR (CDCl$_3$) δ: 1.35 (3H, t, J=7.1 Hz), 3.01 (3H, d, J=4.9 Hz), 4.26 (2H, q, J=7.2 Hz), 5.27 (1H, br), 7.85 (1H, s). A signal due to NH2 was not observed.

Step 3. Ethyl 6-Chloro-5-(methylamino)imidazo[1,2-a]pyridine-8-carboxylate

A mixture of ethyl 2-amino-5-chloro-6-(methylamino) nicotinate (EXAMPLE 8, Step 2, 1.95 g, 8.49 mmol) and 40% aqueous chloroacetaldehyde (1.53 g, 7.79 mmol) in methanol (65 mL) was refluxed for 14 h. Further 40% aqueous chloroacetaldehyde (0.36 g, 1.83 mmol) was added to the mixture, and the resulting mixture was refluxed further 12 h. After cooling to room temperature, the mixture was concentrated in vacuo. The residue was diluted with dichloromethane (100 mL) and 25% aqueous ammonia (30 mL), and the separated aqueous layer was extracted with dichloromethane (100 mL×2), and the combined organic layer was washed with water (100 mL), dried over sodium sulfate, and concentrated in vacuo. The residue was chromatographed on a column of silica gel eluting with methanol/dichloromethane (1:15) to give 1.43 g (66%) of the title compound as a pale brown solid.

MS (EI) m/z: 253 (M$^+$). $^1$H-NMR (CDCl$_3$) δ: 1.44 (3H, t, J=7.1 Hz), 3.22 (3H, br s), 4.48 (2H, q, J=7.1 Hz), 4.79 (1H, br), 7.72 (1H, d, J=1.5 Hz), 7.76 (1H, d, J=1.3 Hz), 8.05 (1H, s).

Step 4. 6-Chloro-5-(methylamino)imidazo[1,2-a]pyridine-8-carboxylic Acid Hydrochloride A mixture of ethyl 6-chloro-5-(methylamino)imidazo[1,2-a]pyridine-8-carboxylate (EXAMPLE 8, Step 3, 1.0 g, 3.94 mmol) and 1N aqueous lithium hydroxide (10 mL) in methanol (10 mL) was stirred at room temperature overnight. After methanol was added, the formed precipitate was collected by filtration. This solid was washed with methanol to give a white solid. This solid was treated with 4 N hydrogen chloride in ethyl acetate (15 mL) at room temperature for 1 h. Diethyl ether was added to the mixture, and the precipitate was collected by filtration. This was washed with diethyl ether to give 979 mg of the title compound as a white solid.

MS (ESI) m/z: 226 (M+H$^+$), 224 (M−H$^-$). $^1$H-NMR (DMSO-d$_6$) δ: 3.44 (3H, d, J=5.0 Hz), 8.06 (1H, d, J=2.4 Hz), 8.22 (1H, s), 8.88 (1H, d, J=2.4 Hz). Signals due to NH and COOH were not observed.

Step 5. N-[(1-Butylpiperidin-4-yl)methyl]-6-chloro-5-(methylamino)imidazo[1,2-a]pyridine-8-carboxamide The title compound was prepared, according to the procedure described in the step 3 of EXAMPLE 5, from 6-chloro-5-(methylamino)imidazo[1,2-a]pyridine-8-carboxylic acid hydrochloride (EXAMPLE 8, Step 4) and 1-(1-butyl-4-piperidinyl)methanamine (EXAMPLE 1, METHOD A, Step 5).

MS (ESI) m/z: 378 (M+H$^+$), 376 (M−H$^-$). m.p.: 148° C. IR (KBr) ν: 3315, 2941, 2928, 1641, 1558, 1504, 1366, 1329, 1315, 1223, 1157, 1103, 704, 677 cm$^{-1}$. $^1$H-NMR (CDCl$_3$) δ: 0.91 (3H, t, J=7.2 Hz), 1.25–1.55 (6H, m), 1.75–2.00 (5H, m), 2.30 (2H, br t, J=7.6 Hz), 2.95 (2H, br d, J=11.4 Hz), 3.14 (3H, d, J=5.8 Hz), 3.45 (2H, t, J=6.3 Hz), 4.55–4.67 (1H, m), 7.64 (1H, d, J=1.5 Hz), 7.69 (1H, d, J=1.5 Hz), 8.23 (1H, s), 10.13 (1H, br s). Anal. Calcd. for C$_{19}$H$_{28}$ClN$_5$O.0.2H$_2$O: C, 59.82; H, 7.50; N, 18.36. Found: C, 60.17; H, 7.60; N, 18.00.

Example 9

6-Chloro-N-{[1-(3-methoxypropyl)piperidine-4-yl]methyl}-5-(methylamino)imidazo[1,2-a]pyridine-8-carboxamide The title compound was prepared, according to the procedure described in the step 3 of EXAMPLE 5, from 6-chloro-5-(methylamino)imidazo[1,2-a]pyridine-8-carboxylic acid hydrochloride (EXAMPLE 8, Step 4) and {1-[3-(methyloxy)propyl]-4-piperidinyl}methylamine (EXAMPLE 7, Step 2).

MS (ESI) m/z: 394 (M+H$^+$), 392 (M−H$^-$). m.p.: 125° C. IR (KBr) ν: 3325, 2924, 1645, 1558, 1506, 1423, 1396, 1331, 1261, 1227, 1119, 698, 658 cm$^{-1}$. $^1$H-NMR (CDCl$_3$) δ: 1.30–1.49 (2H, m), 1.68–1.88 (5H, m), 1.88–2.00 (2H, br t, J=11.7 Hz), 2.39(2H, t, J=7.4 Hz), 2.94(2H, d, J=11.5 Hz), 3.15(3H, d, J=5.8 Hz), 3.32 (3H, s), 3.41 (2H, t, J=4.6 Hz), 3.45 (2H, t, J=6.3 Hz), 4.56–4.65 (1H, m), 7.64 (1H, d, J=1.5 Hz), 7.70(1H, d, J=1.2 Hz), 8.23 (1H, s), 10.1 (1H, br s). Anal. Calcd. for C$_{19}$H$_{28}$ClN$_5$O$_2$.0.25H$_2$O: C, 57.28; H, 7.21; N, 17.58. Found: C, 57.08; H, 7.23; N, 17.26.

Example 10

5-Amino-N-[(1-butyl4-piperidinyl)methyl]-2-ethylimidazo[1,2-a]pyridine-8-carboxamide Step 1, 5-Amino-6-chloro-2-ethylimidazo[1,2-a]pyridine-8-carboxylate The title compound was prepared according to the procedure described in the step 2 of EXAMPLE 1 (METHOD B) using methyl 2,6-diamino-5-chloro-3-pyridinecarboxylate (EXAMPLE 1, METHOD B, Step 1) and 1-bromo-2-butanone instead of ethyl 2-amino-5-chloro-6-(methylamino)nicotinate and chloroacetaldehyde.

MS (EI) m/z: 253 (M$^+$). $^1$H-NMR (DMSO-d$_6$) δ: 1.27 (3H, t, J=7.5 Hz), 2.72 (2H, q, J=7.5 Hz), 3.80 (3H, s), 7.72 (2H, s), 7.86 (1H, s), 7.87 (1H, s).

Step 2, 5-Amino-6-chloro-2-ethylimidazo[1,2-a]pyridine-8-carboxylic Acid

The title compound was prepared according to the procedure described in the step 4 of EXAMPLE 1 (METHOD A) using methyl 5-amino-6-chloro-2-ethylimidazo[1,2-a]pyridine-8-carboxylate (EXAMPLE 10, Step 1).

MS (EI) m/z: 239 (M$^+$). $^1$H-NMR (DMSO-d$_6$) δ: 1.27 (3H, t, J=7.2 Hz), 2.74 (2H, q, J=7.2 Hz), 7.88 (1H, s), 7.95 (1H, s). A signal of COOH was not observed.

Step 3, 5-Amino-N-[(1-butyl-4-piperidinyl)methyl]-6-chloro-2-ethylimidazo[1,2-a]pyridine-8-carboxamide The title compound was prepared according to the procedure described in the step 3 of EXAMPLE 5 from 5-amino-6-chloro-2-ethylimidazo[1,2-a]pyridine-8-carboxylic acid (EXAMPLE 10, Step 2) and 1-(1-butyl-4-piperidinyl)methanamine (EXAMPLE 1, METHOD A, Step 5).

MS (EI) m/z: 391(M$^+$). m.p.: 168° C. IR (KBr) ν: 3200, 2927, 1629, 1606, 1577, 1560, 1544, 1509, 1433, 1334, 1266, 728, 668 cm$^{-1}$. $^1$H-NMR (DMSO-d$_6$) δ: 0.86 (3H, t, J=7.2 Hz), 1.20–1.30 (4H, m), 1.29 (3H, t, J=7.4 Hz), 1.32–1.54 (3H, m), 1.67–1.71 (2H, m), 1.78–1.85 (2H, m), 2.19–2.24 (2H, m), 2.73 (2H, q, J=7.4 Hz), 2.82–2.86 (2H, m), 3.26–3.30 (2H, m), 7.57 (2H, br s), 7.85 (1H, s), 7.91 (1H, s), 9.99 (1H, br). Anal. Calcd. for C$_{20}$H$_{30}$ClN$_5$O.1.5H$_2$O: C, 57.34; H, 7.94; N, 16.72. Found: C, 57.45; H, 8.17; N, 16.56.

Step 4, 5-Amino-N-[(1-butyl-4-piperidinyl)methyl]-2-ethylimidazo[1,2-a]pyridine-8-carboxamide The title compound was prepared according to the procedure described in EXAMPLE 2 from 5-amino-N-[(1-butyl-4-piperidinyl)methyl]-6-chloro-2-ethylimidazo[1,2-a]pyridine-8-carboxamide (EXAMPLE 10, Step 3).

MS (EI) m/z: 393(M$^+$). m.p.: 139–145° C. IR (KBr) ν: 3177, 3087, 2933, 2861, 1640, 1564, 1550, 1517, 1442, 1320, 1139, 772 cm$^{-1}$. $^1$H-NMR (DMSO-d$_6$) δ: 0.86 (3H, t, J=7.2 Hz), 1.29 (3H, t, J=7.5 Hz), 1.20–1.50 (7H, m), 1.68–1.72 (2H, m), 1.78–1.85 (2H, m), 2.22 (2H, t, J=7.1 Hz), 2.73 (2H, q, J=7.5 Hz), 2.82–2.86 (2H, m), 3.27 (2H, t, J=6.2 Hz), 6.04 (1H, d, J=8.1 Hz), 7.27 (2H, br s), 7.71 (1H, s), 7.85 (1H, d, J=8.1 Hz), 10.07 (1H, br). Anal. Calcd. for C$_{20}$H$_{31}$N$_5$O.1.2H$_2$O.0.1C$_4$H$_{10}$O: C, 63.36; H, 9.02; N, 18.11. Found: C, 63.29; H, 8.94; N, 18.13.

Example 11

5-Amino-N-[(1-butylpiperidin-4-yl)methyl]-3-chloro-2-ethylimidazo[1,2-a]piridine-8-carboxamide To a solution of 5-amino-N-[(1-butylpiperidin-4-yl)methyl]-2-ethylimidazo[1,2-a]pyridine-8-carboxamide (EXAMPLE 10, Step 4, 170 mg, 0.48 mmol) in ethanol (4 mL) was added N-chlorosuccinimide (76 mg, 0.57 mmol) at room temperature. After stirring at room temperature for 1 h, water (50 mL) was added to the mixture. The aqueous layer was extracted with dichloromethane (60 mL×3). The combined organic layer was dried over magnesium sulfate and concentrated in vacuo. The residue was suspended in diethyl ether and the insoluble solid was collected by filtration to give 71 mg (38%) of the title compound as a gray solid.

MS (ESI) m/z: 392 (M+H$^+$), 390 (M−H$^-$). m.p.: 86–90° C. IR (KBr) ν: 3414, 3310, 3186, 2932, 2870, 2818, 1701, 1638, 1560, 1514, 1375, 1186, 1092, 818, 768, 640 cm$^{-1}$. $^1$H-NMR (CDCl$_3$) δ: 0.91 (3H, t, J=7.1 Hz), 1.25–2.05 (11H, m), 1.32 (3H, t, J=7.6 Hz), 2.25–2.40 (2H, m), 2.65–2.77 (2H, m), 2.90–3.05 (2H, m), 3.42 (2H, t, J=6.4 Hz), 5.49 (2H, br s), 5.97 (1H, d, J=7.9 Hz), 8.07 (1H, d, J=8.1 Hz), 10.1 (1H, br). Anal. Calcd. for C$_{20}$H$_{30}$ClN$_5$O.1.7H$_2$O: C, 52.45; H, 7.35; N, 15.29. Found: C, 52.46; H, 7.20; N, 15.03.

Example 12

5-Amino-6-chloro-2-ethyl-N-{[1-(3-methoxypropyl)piperidin-4-yl methyl}imidazo[1,2-A]pyridine-8-carboxamide Hydrochloride Salt Step 1, 5-Amino-6-chloro-2-ethyl-N-{[1-(3-methoxypropyl)piperidin-4-yl]methyl}imidazo[1,2-a]pyridine-8-carboxamide The title compound was prepared according to the procedure described in the step 3 of EXAMPLE 5 using 5-amino-6-chloro-2-ethylimidazo[1,2-a]pyridine-8-carboxylic acid (EXAMPLE 10, Step 2) and {1-[3-(methyloxy)propyl]-4-piperidinyl}methylamine (EXAMPLE 7, Step 2).

MS (EI) m/z: 407 (M$^+$). $^1$H-NMR (DMSO-d$_6$) δ: 1.18–1.33 (2H, m), 1.30 (3H,t, J=7.6 Hz), 1.40–1.54 (1H, m), 1.57–1.71 (4H, m), 1.78–1.86 (2H, m), 2.26 (2H, t, J=7.3 Hz), 2.74 (2H, q, J=7.6 Hz), 2.81–2.85 (2H, m), 3.20 (3H, s), 3.26–3.33 (4H, m), 7.57 (2H, br s), 7.86 (1H, s), 7.91 (1H, s), 9.99 (1H, br).

Step 2, 5-Amino-6-chloro-2-ethyl-N-{[1-(3-methoxypropyl)piperidin-4-yl]methyl}imidazo[1,2-a]pyridine-8-carboxamide Hydrochloride Salt 5-amino-6-chloro-2-ethyl-N-{[1-(3-methoxypropyl)piperidin-4-yl]methyl}imidazo[1,2-a]pyridine-8-carboxamide (EXAMPLE 12, Step 1, 118 mg, 0.29 mmol) was treated with hydrogen chloride/methanol reagent 10 (105 mg), concentrated and crystallized from methanol and diethyl ether. 73 mg (55%) of the title compound was obtained.

MS (EI) m/z: 407 (M$^+$). m.p.: 265–269° C. IR (KBr) ν: 3250, 3288, 3140, 2928, 2542, 1657, 1638, 1578, 1516, 1429, 1323, 1229, 1111, 719 cm$^{-1}$. $^1$H-NMR (DMSO-d$_6$) δ: 1.30 (3H, t, J=7.5 Hz), 1.42–1.58 (2H, m), 1.73–1.91 (5H, m), 2.75 (2H, q, J=7.5 Hz), 2.79–3.08 (4H, m), 3.23 (3H, s), 3.28–3.52 (6H, m), 7.64 (2H, br s), 7.87 (1H, s), 7.94 (1H, s), 9.99 (1H, br). Anal. Calcd. for C$_{20}$H$_{30}$ClN$_5$O$_2$.HCl: C, 54.05; H, 7.03; N, 15.76. Found: C, 54.06; H, 7.09; N, 15.66.

Example 13

5-Amino-2-ethyl-N-{[1-(3-methoxypropyl)piperidin-4-yl]methyl}imidazo[1,2-a]pyridine-8-carboxamide Hydrochloride Salt The title compound was prepared, according to the procedure described in EXAMPLE 2 and the step 2 in EXAMPLE 12, from 5-amino-6-chloro-2-ethyl-N-{[1-(3-methoxypropyl)piperidin-4-yl]methyl}imidazo[1,2-a]pyridine-8-carboxamide (EXAMPLE 12, Step 1).

MS (EI) m/z: 373(M$^+$). IR (KBr) ν: 3348, 3308, 3248, 3180, 2932, 2685, 1647, 1560, 1516, 1456, 1431, 1379, 1329, 1321, 1285, 1121 cm$^{-1}$. $^1$H-NMR (DMSO-d$_6$) δ: 1.30 (3H, t, J=7.5 Hz), 1.44–1.60 (2H, m), 1.73–1.87 (1H, m), 1.87–1.93 (4H, m), 2.74 (2H, q, J=7.5 Hz), 2.80–3.06 (4H, m), 3.23 (3H, s), 3.25–3.50 (6H, m), 6.05 (1H, d, J=8.1 Hz), 7.34 (2H, br s), 7.74 (1H, s), 7.87 (1H, d, J=8.1 Hz), 10.08 (1H, br). Anal. Calcd. for C$_{20}$H$_{31}$N$_5$O$_2$.HCl.0.1H$_2$O: C, 58.34; H, 7.88; N, 17.01. Found: C, 58.27; H, 7.96; N, 16.81.

Example 14

5-Amino-6-chloro-2-ethyl-N-{1-[3-(methoxy)propyl]4-piperidinyl}imidazo[1,2-a]pyridine-8-carboxamide The title compound was prepared according to the procedure described in the step 3 in EXAMPLE 5 using 5-amino-6-chloro-2-ethylimidazo[1,2-a]pyridine-8-carboxylic acid (EXAMPLE 10, Step 2) and 1-[3-(methyloxy)propyl]-4-piperidinamine (EXAMPLE 3).

MS (EI) m/z: 393 (M$^+$). m.p.: 179° C. IR (KBr) ν: 3329, 3169, 3055, 2938, 1653, 1630, 1583, 1540, 1513, 1427, 1337, 1324, 1122, 745 cm$^{-1}$. $^1$H-NMR (DMSO-d$_6$) δ: 1.31 (3H, t, J=7.5 Hz), 1.40–1.55 (2H, m), 1.66 (2H, quint, J=6.9

Hz), 1.87–1.92 (2H, m), 2.16–2.28 (2H, m), 2.33 (2H, t, J=7.4 Hz), 2.66–2.71 (2H, m), 2.74 (2H, q, J=7.5 Hz), 3.22 (3H, s), 3.33–3.42 (2H, m), 3.88–3.95 (1H, m), 7.84 (1H, s), 7.90 (1H, s), 10.07 (1H, d, J=7.5 Hz). Anal. Calcd. for $C_{19}H_{28}ClN_5O_2.0.1C_4H_{10}O$: C, 58.06; H, 7.28; N, 17.45. Found: C, 58.08; H, 7.51; N, 17.08.

Example 15

5-Amino-6-chloro-2-ethyl-N-(piperidin-4-ylmethyl)imidazo[1,2-a]pyridine-8-carboxamide Step 1. tert-Butyl 4-({[1(5-Amino-6-chloro-2-ethylimidazo[1,2-a]pyridin-8-yl)carbonyl]amino}methyl)piperidine-1-carboxylate A mixture of 5-amino-6-chloro-2-ethylimidazo[1,2-a]pyridine-8-carboxylic acid (EXAMPLE 10, Step 2, 10.00 g, 41.72 mmol), tert-butyl 4-(aminomethyl)piperidine-1-carboxylate (J. Prugh, L. A. Birchenough and M. S. Egbertson, *Synth. Commun.*, 1992, 22, 2357–60) (15.20 g, 70.93 mmol), diethyl phosphorocyanidate (10.76 mL, 70.93 mmol) and diisopropylethylamine (18.17 mL, 104.4 mmol) in N,N-dimethylformamide (267 mL) was stirred at room temperature for 43 h. The solvent was removed by evaporation. The residue was basified with aqueous sodium bicarbonate (40 mL), and extracted with dichloromethane (5×100 mL). The combined extract was washed with brine, dried over magnesium sulfate, and concentrated in vacuo. Flash chromatography of the residue eluting with dichloromethane/methanol (100:1 to 20:1) afforded 19.08 g (90%) of the title compound as a yellow oil.

$^{11}$H-NMR (CDCl$_3$) δ: 1.35 (3H, t, J=7.6 Hz), 1.45 (9H, s), 1.88–1.28 (5H, m), 2.88–2.64 (2H, m), 3.52–3.38 (2H, m), 4.30–3.97 (4H, m), 5.17 (2H, br s), 7.21 (1H, s), 8.19 (1H, s), 10.21 (1H, br s).

Step 2. 5-Amino-6-chloro-2-ethyl-N-(piperidin-4-ylmethyl)imidazo[1,2-a]pyridine-8-carboxamide To a stirred solution of tert-butyl 4-({[(5-amino-6-chloro-2-ethylimidazo[1,2-a]-pyridin-8-yl)carbonyl]amino}methyl)piperidine-1-carboxylate (EXAMPLE 15, Step 1, 13.71 g, 31.44 mmol) in 10% hydrochloric acid methanol solution (314 mL) was added concentrated hydrochloric acid (10 mL). After stirring at room temperature for 26 h, the mixture was concentrated to about 50 mL in vacuo. The residue was basified with an excess of sodium carbonate and then insoluble material was filtered off. The filtrate was concentrated azeotropically with ethanol and diluted with a mixture of dichloromethane and methanol (5:1, 200 mL). The formed inorganic solid was filtered off again. The filtrate was concentrated in vacuo to give a pale yellow amorphous, which was crystallized from ethanol to afford 4.79 g (45%) of the title compound as an off-white solid. Furthermore, 5.09 g (48%) of the compound was obtained from the mother liquid.

MS (ESI) m/z: 336 (M+H)$^+$, 334 (M−H)$^−$. m.p. (TG/DTA): 153° C. IR (KBr) v: 3387, 3300, 3188, 2964, 1639, 1605, 1562, 1514 cm$^{-1}$. $^1$H-NMR (DMSO-d$_6$) δ: 1.30–0.90 (2H, m), 1.30 (3H, t, J=7.6 Hz), 1.74–1.50 (3H, m), 2.55–2.36 (2H, m), 2.75 (2H, q, J=7.6 Hz), 3.04–2.86 (2H, m), 3.27 (2H, t, J=5.9 Hz), 7.86 (1H, s), 7.94 (1H, s), 10.05–9.94 (1H, m). Anal. Calcd. for $C_{16}H_{22}ClN_5O.2.5H_2O.0.8EtOH$: C, 50.70; H, 7.49; N, 16.80. Found: C, 50.57; H, 7.27; N, 16.80.

Example 16

5-Amino-N-[(1-butyl-4-piperidinyl)methyl]-6 chloro-2-propylimidazo[1,2-a]pyridine-8-carboxamide p-Toluenesulfonate Salt Step 1, Methyl 5-Amino-6-chloro-2-propylimidazo[1,2-a]pyridine-8-carboxylate The title compounds were prepared according to the procedure described in the step 2 EXAMPLE 1 (METHOD B) using methyl 2,6-diamino-5-chloro-3-pyridinecarboxylate (EXAMPLE 1, METHOD B, Step 1), 1-chloropentane-2-one (Synthesis, 1987, 2, 188–190) and sodium iodide.

MS (EI) m/z: 267 (M$^+$). $^1$H-NMR (DMSO-d$_6$) δ: 0.97 (3H, t, J=7.4 Hz), 1.64–1.76 (2H, m), 2.66 (2H, t, J=7.4 Hz), 3.81 (3H, s), 7.72 (2H, br s), 7.86 (1H, s), 7.87 (1H, s).

Step 2, 5-Amino-6-chloro-2-propylimidazo[1,2-a]pyridine-8-carboxylic Acid

The title compound was prepared according to the procedure described in the step 4 in EXAMPLE 1 (METHOD A) using methyl 5-Amino-6-chloro-2-propylimidazo[1,2-a]pyridine-8-carboxylate (EXAMPLE 16, Step 1). $^1$H-NMR (DMSO-d$_6$) δ: 0.98 (3H. t, J=7.4 Hz), 1.66–1.78 (2H, m), 2.71 (2H, t, J=7.4 Hz), 7.92 (1H, s), 7.99 (1H, s), 8.09 (2H, br s). A signal of COOH was not observed.

Step 3, 5-Amino-N-[(1-butyl4-piperidinyl)methyl]-6-chloro-2-propylimidazo[1,2-a]pyridine-8-carboxamide The title compound was prepared according to the procedure described in the step 3 in EXAMPLE 5 using 5-amino-6-chloro-2-propylimidazo[1,2-a]pyridine-8-carboxylic acid (EXAMPLE 16, Step 2) and 1-(1-butyl-4-piperidinyl)methanamine (EXAMPLE 1, METHOD A, Step 5).

MS (EI) m/z: 405(M$^+$). $^1$H-NMR (DMSO-d$_6$) δ: 0.86 (3H, t, J=7.4 Hz), 0.97 (3H, t, J=7.5 Hz), 1.20–1.50 (6H, m), 2.15–2.15 (2H, m), 2.69 (2H, t, J=7.4 Hz), 2.75–2.89 (2H, m), 3.28 (2H, t, J=6.0 Hz), 7.57 (2H, br s), 7.85 (1H, s), 7.90 (1H, s), 10.00 (1H, br).

Step 4, 5-Amino-N-[(1-butyl-4-piperidinyl)methyl]-6-chloro-2-propylimidazo[1,2-a]pyridine-8-carboxamide p-Toluenesulfonate Salt 5-Amino-N-[(1-butyl-4-piperidinyl)methyl]-6-chloro-2-propylimidazo[1,2-a]pyridine-8-carboxamide (EXAMPLE 16, Step 3, 185 mg, 0.46 mmol) was treated with p-toluenesulfonic acid (86.6 mg, 0.46 mmol) in methanol, concentrated and washed with diethyl ether and hexane. 200 mg (76%) of the title compound was obtained.

MS (EI) m/z: 405 (M$^+$). m.p.: 165° C. IR (KBr) v: 3188, 2961, 2934, 1638, 1607, 1558, 1514, 1435, 1335, 1231, 1170, 1123, 1034, 1011, 683, 569 cm$^{-1}$. $^1$H-NMR (DMSO-d$_6$) δ: 0.90 (3H, t, J=7.4 Hz), 0.99 (3H, t, J=7.2 Hz), 1.26–1.33 (2H, m), 1.40–1.65 (4H, m), 1.68–1.96 (5H, m), 2.29 (3H, s), 2.70 (2H, t, J=7.7 Hz), 2.81–3.04 (4H, m), 3.23–3.39 (2H, m), 3.51–3.54 (2H, m), 7.11 (2H, d, J=8.1 Hz), 7.48 (2H, d, J=8.1 Hz), 7.63 (2H, br s), 7.87 (1H, s), 7.93 (1H, s), 8.85 (1H, br s), 9.99 (1H, br). Anal. Calcd. for $C_{21}H_{32}ClN_5O.C_7H_8O_3S$. 0.3H$_2$O: C, 57.63; H, 7.01; N, 12.00. Found: C, 57.42; H, 7.08; N, 11.99.

Example 17

5-Amino-N-[(1-butyl-4-piperidinyl)methyl]-2-propylimidazo[1,2-a]pyridine-8-carboxamide The title compound was prepared according to the procedure described in EXAMPLE 2 from 5-amino-N-[(1-butyl-4-piperidinyl)methyl]-6-chloro-2-propylimidazo[1,2-a]pyridine-8-carboxamide (EXAMPLE 16, Step 3).

MS (EI) m/z: 371(M$^+$). m.p.: 172° C. IR (KBr) v: 3356, 3184, 2963, 2932, 1639, 1562, 1518, 1441, 1379, 1319, 1281, 1136, 772, 714 cm$^{31\ 1}$. $^1$H-NMR (DMSO-d$_6$) δ: 0.86 (3H, t, J=7.2 Hz), 0.97 (3H, t, J=7.3 Hz), 1.20–1.55 (7 H, m), 1.65–1.85 (6H, m), 2.22 (2H, t, J=7.3 Hz), 2.68 (2H, t, J=7.4

Hz), 2.82–2.86 (2H, m), 3.17 (3H, s), 3.27 (2H, t, J=5.9 Hz), 6.04 (1H, d, J=8.1 Hz), 7.27 (2H, br s), 7.71 (1H, s), 7.85 (1H, d, J=8.1 Hz), 10.08 (1H, br). Anal. Calcd. for $C_{21}H_{33}N_5O \cdot 0.8H_2O$: C, 65.36; H, 9.04; N, 18.15. Found: C, 64.91; H, 9.20; N, 18.11.

Example 18

5-Amino-6-chloro-2-propyl-N-{1-[3-(methoxy)propyl]-4-piperidinyl}imidazo[1,2-a]pyridine-8-carboxamide Hydrochloride Salt Step 1, 5-Amino-6-chloro-2-propyl-N-{1-[3-(methoxy)propyl]-4-piperidinyl}imidazo[1,2-a]pyridine-8-carboxamide The title compound was prepared according to the procedure described in the step 3 in EXAMPLE 5 using 5-amino-6-chloro-2-propylimidazo[1,2-a]pyridine-8-carboxylic acid (EXAMPLE 16, Step 2) and 1-[3-(methyloxy)propyl]-4-piperidinamine (EXAMPLE 3).

MS (EI) m/z: 407 (M$^+$). $^1$H-NMR (DMSO-d$_6$) o: 0.99 (3H, t, J=7.4 Hz), 1.43–1.57 (2H, m), 1.61–1.80 (4H, m), 1.82–1.96 (2H, m), 2.17–2.37 (4H, m), 2.59–2.72 (2H, m), 2.70 (2H, t, J=7.2 Hz), 3.22 (3H, s), 3.27–3.48 (2H, m), 3.85–4.01 (1H, m), 7.57 (2H, br s), 7.84 (1H, s), 7.90 (1H, s), 10.10 (1H, br).

Step 2, 5-Amino-6chloro-2-propyl-N-{1-[3-(methoxy)propyl]-4-piperidinyl}imidazo[1,2-a]pyridine-8-carboxamide Hydrochloride Salt The title compound was prepared according to the procedure described in the step 2 in EXAMPLE 12 using 5-amino-6-chloro-2-propyl-N-{1-[3-(methoxy)propyl]-4-piperidinyl}imidazo[1,2-a]pyridine-8-carboxamide (EXAMPLE 18, Step 1).

MS (EI) m/z: 407 (M$^+$). m.p.: 243° C. IR (KBr) v: 3165, 2926, 2629, 2517, 1645, 1634, 1605, 1553, 1510, 1427, 1227, 1119, 746 cm$^{-1}$. $^1$H-NMR (DMSO-d$_6$) δ: 1.00 (3H, t, J=7.5 Hz), 1.68–1.98 (6H, m), 2.13–2.28 (2H, m), 2.64–2.76 (2H, m), 3.00–3.19 (2H, m), 3.26 (2H, t, J=7.2 Hz), 3.32–3.63 (8H, m), 3.98–4.14 (1H, m), 7.67 (2H, br s), 7.86 (1H, s), 7.94 (1H, s), 10.00 (1H, br). Anal. Calcd. for $C_{20}H_{30}ClN_5O_2 \cdot HCl$: C, 54.05; H, 7.03; N, 15.76. Found: C, 54.01; H, 7.21; N, 15.61.

Example 19

5-Amino-N-[1-(3-methoxypropyl)piperidin-4-yl]-2-propylimidazo[1,2-a]pyridine-8-carboxamide Hydrochloride Salt Step 1, 5-Amino-N-[1-(3-methoxypropyl)piperidin-4-yl]-2-propylimidazo[1,2-a]pyridine-8-carboxamide The title compound was prepared according to the procedure described in EXAMPLE 2 using 5-amino-6-chloro-N-[1-(3-methoxypropyl)piperidin-4-yl]-2-propylimidazo[1,2-a]pyridine-8-carboxamide (EXAMPLE 18, Step 1).

MS (EI) m/z: 373 (M$^+$). $^1$H-NMR (DMSO-d$_6$) δ: 0.99 (3H, t, J=7.4 Hz), 1.42–1.53 (2H, m), 1.60–1.89 (6H, m), 2.14–2.34 (4H, m), 2.58–2.70 (4H, m), 3.20 (3H, s), 3.31–3.35 (2H, m), 3.86–3.98 (1H, m), 6.04 (1H, d, J=8.1 Hz), 7.28 (2H, br s), 7.71 (1H, s), 7.85 (1H, d, J=8.1 Hz), 10.19 (1H, br).

Step 2, 5-Amino-N-[1-(3-methoxypropyl)piperidin-4-yl]-2-propylimidazo[1,2-a]pyridine-8-carboxamide Hydrochloride Salt The title compound was prepared according to the procedure described in the step 2 in EXAMPLE 12 using 5-amino-N-[1-(3-methoxypropyl)piperidin-4-yl]-2-propylimidazo[1,2-a]pyridine-8-carboxamide (EXAMPLE 19, Step 1).

MS (EI) m/z: 373 (M$^+$). m.p.: 238° C. IR (KBr) v: 3447, 3377, 3339, 3177, 2932, 2714, 2648, 1632, 1566, 1518, 1437, 1377, 1308, 1296, 1277, 1236, 1117, 773 cm$^{-1}$. $^1$H-NMR (DMSO-d$_6$) δ: 1.00 (3H, t, J=7.4 Hz), 1.69–2.00 (6H, m), 2.15–2.19 (2H, m), 2.67–2.72 (2H, m), 3.02–3.14 (2H, m), 3.25 (3H, s), 3.32–3.58 (6H, m), 4.02–4.10 (1H, m), 6.06 (1H, d, J=8.0 Hz), 7.40 (2H, br s), 7.75 (1H, s), 7.87 (1H, d, J=8.0 Hz), 10.12 (1H, br s). Anal. Calcd. for $C_{20}H_{31}N_5O_2 \cdot HCl \cdot 1.4H_2O$: C, 55.20; H, 8.06; N, 16.09. Found: C, 55.53; H, 7.99; N, 16.16.

Example 20

5-Amino-N-[(1-butyl-4-piperidinyl)methyl]-6-chloro-2-isopropylimidazo[1,2-a]pyridine-8-carboxamide Step 1, Methyl 5-Amino-6-chloro-2-isopropylimidazo[1,2-a]pyridine-8-carboxylate The title compound was prepared according to the procedure described in the step 2 in EXAMPLE 1 (METHOD B) from methyl 2,6-diamino-5-chloro-3-pyridinecarboxylate (EXAMPLE 1, METHOD B, Step 1) and 1-bromo-3-methylbutan-2-one (Synthesis, 1976, 194–196) using N,N-dimethylformamide as a solvent.

MS (EI) m/z: 267 (M$^+$). $^1$H-NMR (DMSO-d$_6$) δ: 1.29 (6H, d, J=6.9 Hz), 2.93–3.02 (1H, m), 3.81 (3H, s), 7.73 (2H, br s), 7.87 (1H, s), 7.89 (1H, s).

Step 2, 5-Amino-6-chloro-2-isopropylimidazo[1,2-a]pyridine-8-carboxylic Acid

The title compound was prepared according to the procedure described in the step 4 in EXAMPLE 1 (METHOD A) from methyl 5-amino-6-chloro-2-isopropylimidazo[1,2-a]pyridine-8-carboxylate (EXAMPLE 20, Step 1). Rf value: 0.33 (CH$_2$Cl$_2$:MeOH, 20:1, v/v)

$^1$H-NMR (DMSO-d$_6$) δ: 1.32 (6H, d, J=7.0 Hz), 3.04–3.13 (1H, m), 7.96 (1H, s), 8.09 (1H, s), 8.22 (2H, br s). A signal due to COOH was not observed.

Step 3, 5-Amino-N-[(1-butyl-4-piperidinyl)methyl]-6-chloro-2-isopropylimidazo[1,2-a]pyridine-8-carboxamide The title compounds were prepared according to the procedure described in the step 3 in EXAMPLE 5 using 5-Amino-6-chloro-2-isopropylimidazo[1,2-a]pyridine-8-carboxylic acid (EXAMPLE 20, Step 2) and 1-(1-butyl-4-piperidinyl)methanamine (EXAMPLE 1, METHOD A, Step 5).

MS (EI) m/z: 405(M$^+$). m.p.: 168° C. IR (KBr) v: 3325, 3196, 2959, 2932, 1641, 1609, 1560, 1514, 1462, 1425, 1271, 1236, 773, 750, 700, 656 cm$^{-1}$. $^1$H-NMR (DMSO-d$_6$) δ: 0.86 (3H, t, J=7.0 Hz), 1.19–1.56 (13H, m), 1.69–1.85 (4H, m), 2.21 (2H, t, J=7.2 Hz), 2.79–2.89 (2H, m), 2.93–3.07 (1H, m), 3.29 (2H, t, J=5.9 Hz), 7.57 (2H, br s), 7.85 (1H, s), 7.92 (1H, s), 10.06 (1H, br). Anal. Calcd. for $C_{21}H_{32}ClN_5O \cdot 0.6H_2O$: C, 60.52; H, 8.03; N, 16.80. Found: C, 60.33; H, 8.10; N, 16.73.

Example 21

5-Amino-N-[(1-butyl-4-piperidinyl)methyl]-2-isopropylimidazo[1,2-a]pyridine-8-carboxamide The title compound was prepared according to the procedure described in EXAMPLE 2 using 5-amino-N-[(1-butyl-4-piperidinyl)methyl]-6-chloro-2-isopropylimidazo[1,2-a]pyridine-8-carboxamide (EXAMPLE 20, Step 3).

MS (EI) m/z: 371(M+). m.p.: 138° C. IR (KBr) ν: 3342, 3198, 2955, 2928, 1641, 1611, 1560, 1516, 1441, 1379, 1290, 773, 696 cm$^{-1}$. $^1$H-NMR (DMSO-d$_6$) δ: 0.86 (3H, t, J=7.2 Hz), 1.18–1.52 (13H, m), 1.70–1.74 (2H, m), 1.79–1.86 (2H, m), 2.20–2.25 (2H, m), 2.83–2.87 (2H, m), 2.93–3.06 (1H, m), 3.25–3.29 (2H, m), 6.03 (1H, d, J=8.0 Hz), 7.28 (2H, br s), 7.72 (1H, s), 7.85 (1H, d, J=8.0 Hz), 10.14 (1H, br). Anal. Calcd. for C$_{21}$H$_{33}$N$_5$O.1.3H$_2$O: C, 63.87; H, 9.09; N, 17.73. Found: C, 63.72; H, 8.94; N, 17.56.

Example 22

5-Amino-N-[(1-butyl-4-piperidinyl)methyl]-6-chloro-2-phenylimidazo[1,2-A]pyridine-8-carboxamide Hydrochloride Salt Step 1, Methyl 5-Amino-6-chloro-2-phenylimidazo[1,2-a]pyridine-8-carboxylate The title compounds were prepared according to the procedure described in the step 2 in EXAMPLE 1 (METHOD B) using methyl 2,6-diamino-5-chloro-3-pyridinecarboxylate (EXAMPLE 1, METHOD B, Step 1), 2-bromoacetophenone and sodium iodide.

MS (EI) m/z: 301 (M+). $^1$H-NMR (DMSO-d$_6$) δ: 3.86 (3H, s), 7.33–7.39 (1H, m), 7.46–7.52 (2H, m), 7.85 (2 H, br s), 7.93–7.95 (3H, m), 8.58 (1H, s).

Step 2, 5-Amino-6-chloro-2-phenylimidazo[1,2-a] pyridine-8-carboxylic Acid

The title compounds were prepared according to the procedure described in the step 4 in EXAMPLE 1 (METHOD A) using methyl 5-Amino-6-chloro-2-phenylimidazo[1,2-a]pyridine-8-carboxylate (EXAMPLE 22, Step 1).

$^1$H-NMR (DMSO-d$_6$) δ: 7.39–7.44 (1H, m), 7.50–7.55 (2H, m), 7.89–7.92 (2H, m), 7.97 (1H, s), 8.16 (2H, br s), 8.66 (1H, s). A signal due to COOH was not observed.

Step 3, 5-Amino-N-[(1-butyl-4-piperidinyl)methyl]-6-chloro-2-phenylimidazo[1,2-a]pyridine-8-carboxamide The title compounds were prepared according to the procedure described in the step 3 in EXAMPLE 5 from 5-amino-6-chloro-2-phenylimidazo[1,2-a]pyridine-8-carboxylic acid (EXAMPLE 22, Step 2) and 1-(1-butyl-4-piperidinyl)methanamine (EXAMPLE 1, METHOD A, Step 5).

$^1$H-NMR (DMSO-d$_6$) δ: 0.86 (3H, t, J=7.2 Hz), 1.22–1.65 (7H, m), 1.74–1.90 (4H, m), 2.24 (2H, t, J=7.2 Hz), 2.86–2.90 (2H, m), 3.30–3.37 (2H, m), 7.36–7.42 (1H, m), 7.51 (2H, t, J=7.3 Hz), 7.70 (2H, br s), 7.92–7.94 (3H, m), 8.62 (1H, s), 10.01 (1H, br).

Step 4, 5-Amino-N-[(1-butyl-4-piperidinyl)methyl]-6-chloro-2-phenylimidazo[1,2-a]pyridine-8-carboxamide Hydrochloride Salt The title compound was prepared according to the procedure described in the step 2 in EXAMPLE 12 using 5-amino-N-[(1-butyl-4-piperidinyl)methyl]-6-chloro-2-phenylimidazo[1,2-a]pyridine-8-carboxamide (EXAMPLE 22, Step 3).

MS (EI) m/z: 439 (M+). m.p.: 263° C. IR (KBr) ν: 3508, 3173, 2959, 1647, 1607, 1587, 1556, 1510, 1452, 1425, 1340, 743, 729 cm$^{-1}$. $^1$H-NMR (DMSO-d$_6$) δ: 0.90 (3H, t, J=7.5 Hz), 1.23–1.36 (2H, m), 1.52–1.68 (4H, m), 1.82–1.97 (3H, m), 2.82–3.01 (4H, m), 3.32–3.51 (4H, m), 7.38–7.43 (1H, m), 7.50–7.55 (2H, m), 7.80 (2H, br s), 7.93–7.95 (3H, m), 8.71 (1H, s), 9.60 (1H, br s), 10.02 (1H, br). Anal. Calcd. for C$_{24}$H$_{30}$ClN$_5$O.HCl.1.5H$_2$O: C, 57.26; H, 6.81; N, 13.91. Found: C, 57.58; H, 6.72; N, 13.88.

Example 23

5-Amino-N-[(1-butyl-4-piperidinyl)methyl]-2-phenylimidazo[1,2-a]pyridine-8-carboxamide Step 1, 5-Amino-N-[(1-butyl-4-piperidinyl)methyl]-2-phenylimidazo[1,2-a]pyridine-8-carboxamide The title compound was prepared according to the procedure described in EXAMPLE 2 using 5-amino-N-[(1-butyl-4-piperidinyl)methyl]-6-chloro-2-phenylimidazo[1,2-a]pyridine-8-carboxamide (EXAMPLE 22, Step 3).

MS (EI) m/z: 405(M+). m.p.: 221 ° C. IR (KBr) ν: 3327, 3152, 2930, 1641, 1558, 1379, 1294, 773, 739, 712 cm$^{-1}$. $^1$H-NMR (DMSO-d$_6$) δ: 0.86 (3H, t, J=7.1 Hz), 1.23–1.64 (7H, m), 1.75–1.90 (4H, m), 2.22–2.27 (2H, m), 2.87–2.90 (2H, m), 3.27–3.40 (2H, m), 6.12 (1H, d, J=8.1 Hz), 7.35–7.53 (5H, m), 7.92–7.94 (3H, m), 8.44 (1H, s), 10.10 (1H, br). Anal. Calcd. for C$_{24}$H$_{31}$N$_5$O.0.1H$_2$CO$_3$. 1.7H$_2$O: C, 65.44; H, 7.88; N, 15.83. Found: C, 65.79; H, 7.48; N, 15.63.

Example 24

5-Amino-N-[(1-butyl-4-piperidinyl)methyl]-2,6-dichloroimidazo[1,2-a]pyridine-8-carboxamide Step 1, Ethyl 5-Chloro-2-[(chloroacetyl)amino]-6-[(2,2-dimethylpropanoyl)amino]nicotinate To a solution of ethyl 2-amino-5-chloro-6-[(2,2-dimethylpropanoyl)amino]nicotinate (EXAMPLE 1, METHOD A, Step 2, 5 g, 16.7 mmol) in tetrahydrofuran (150 mL) were added potassium carbonate (5.1 g, 36.6 mmol) and chloroacetyl chloride (2.7 mL, 33.3 mmol) at 0° C. under nitrogen. The mixture was stirred at 0° C. for 2 h and at room temperature for 15 h. After addition of water, the mixture was extracted with ethyl acetate and washed with brine. The combined organic layer was dried over sodium sulfite and concentrated to give the title compound as a pale yellow solid.

H-NMR (CDCl$_3$) δ: 1.36 (9H, s), 1.42 (3H, t, J=7.1 Hz), 4.41 (2H, q, J=7.1 Hz), 4.81 (1H, br s), 8.30 (1H, s), 8.43 (1H, br s), 11.14 (1H, br s).

Step 2, Ethyl 5-Amino-6-chloro-2-oxo-2,3-dihydroimidazo[1,2-a]pyridine-8-carboxylate A solution of ethyl 5-chloro-2-[(chloroacetyl)amino]-6-[(2,2-dimethylpropanoyl)amino]nicotinate (EXAMPLE 24, Step 1, 6.55 g) in t-butyl alcohol (150 mL) was refluxed for 42 h. The formed precipitate was collected by filtration and washed with ethyl acetate to afford 1.28 g (29%) of the title compound as a pale purple solid.

MS (EI) m/z: $^1$H-NMR (DMSO-d$_6$) δ: 1.28 (3H, t, J=7.2 Hz), 4.34 (2H, q, J=7.2 Hz), 4.75 (2H, s), 8.38 (1H, s), 9.49 (2H, br s).

Step 3, Ethyl 5-Amino-2,6-dichloroimidazo[1,2-a] pyridine-8-carboxylate

A solution of ethyl 5-Amino-6-chloro-2-oxo-2,3-dihydroimidazo[1,2-a]pyridine-8-carboxylate (EXAMPLE 24, Step 2, 0.50 g, 2.00 mmol) in phosphorus oxychloride (4 mL) was refluxed for 4 h. After cooling, the mixture was evaporated. The obtained residue was carefully treated with water and 25% aqueous ammonia. The formed solid was collected by filtration to give 385 mg (72%) of the title compound.

MS (ESI+) m/z: 274 (M+1) $^1$H-NMR (DMSO-d$_6$) δ: 1.29 (3H, t, J=7.1 Hz), 4.27 (2H, q, J=7.1 Hz), 7.93 (2H, br s), 7.94 (1H, s), 8.19 (1H, s).

Step 4, 5-Amino-2,6-dichloroimidazo[1,2-a]pyridine-8-carboxylic Acid

The title compounds were prepared according to the procedure described in the step 4 in EXAMPLE 1 (METHOD A) using methyl 5-Amino-2,6-chloroimidazo[1,2-a]pyridine-8-carboxylate (EXAMPLE 24, Step 3).

MS (ES1-) m/z: 244 (M-1). $^1$H-NMR (DMSO-d$_6$) δ: 7.35 (2H, br s), 7.91 (1H, s), 8.13 (1H, s). A signal due to COOH was not observed.

Step 5, 5-Amino-N-[(1-butyl-4-piperidinyl)methyl]-2,6-dichloroimidazo[1,2-a]pyridine-8-carboxamide The title compounds were prepared according to the procedure described in the step 3 in EXAMPLE 5 using 5-amino-2,6-dichloroimidazo[1,2-a]pyridine-8-carboxylic acid (EXAMPLE 24, Step 4) and 1-(1-butyl-4-piperidinyl)methanamine (EXAMPLE 1, METHOD A, Step 5).

MS (EI) m/z: 397(M$^+$). IR (KBr) ν: 3323, 3165, 2951, 2936, 1634, 1607, 1576, 1556, 1491, 1312, 1258, 968, 723, 669 cm$^{-1}$. $^1$H-NMR (DMSO-d$_6$) δ: 0.86 (3H, t, J=6.9 Hz), 1.11–1.53 (7H, m), 1.64–1.68 (2H, m), 1.77–1.86 (2H, m), 2.19–2.24 (2H, m), 2.81–2.86 (2H, m), 3.16–3.29 (2H, m), 7.75 (2H, br s), 7.97 (1H, s), 8.23 (1H, s), 9.25 (1H, br). Anal. Calcd. for C$_{18}$H$_{25}$Cl$_2$N$_5$O.2H$_2$O: C, 49.77; H, 6.82; N, 16.12. Found: C, 49.71; H, 6.82; N, 15.76.

Example 25

5-Amino-N-[(1-butyl4-piperidinyl)methyl]-2-chloroimidazo[1,2-a]pyridine-8-carboxamide Step 1, Ethyl 5-Amino-2-oxo-2,3-dihydroimidazo[1,2-a]pyridine-8-carboxylate The title compound was prepared according to the procedure described in EXAMPLE 2 using ethyl 5-amino-6-chloro-2-oxo-2,3-dihydroimidazo[1,2-a]pyridine-8-carboxylate (EXAMPLE 24, Step 2).

MS (ESI+) m/z: 222 (M+1). $^1$H-NMR (DMSO-d$_6$) δ: 1.24 (3H, t, J=7.1 Hz), 4.09 (2H, s), 4.18 (2H, q, J=7.1 Hz), 6.01 (1H, d, J=9.0 Hz), 7.96 (1H, d, J=9.0 Hz), 8.06 (2H, br s).

Step 2, Ethyl 5-Amino-2-chloroimidazo[1,2-a]pyridine-8-carboxylate

The title compound was prepared according to the procedure described in the step 3 in EXAMPLE 24 using ethyl 5-amino-2-oxo-2,3-dihydroimidazo[1,2-a]pyridine-8-carboxylate (EXAMPLE 25, Step 1).

MS (ESI+) m/z: 240 (M+1). $^1$H-NMR (DMSO-d$_6$) δ: 1.30 (3H, t, J=7.0 Hz), 4.27 (2H, q, J=7.0 Hz), 6.12 (1H, d, J=8.6 Hz), 7.66 (2H, br s), 7.95 (1H, d, J=8.6 Hz), 8.01 (1H, s).

Step 3, 5-Amino-2,6-dichloroimidazo[1,2-a]pyridine-8-carboxylic Acid

The title compound was prepared according to the procedure described in the step 4 in EXAMPLE 1 (METHOD A) from ethyl 5-amino-2-chloroimidazo[1,2-a]pyridine-8-carboxylate (EXAMPLE 25, Step 2).

MS (ESI+) m/z: 212 (M+1). $^1$H-NMR (DMSO-d$_6$) δ: 6.19 (1H, d, J=8.4 Hz), 7.80 (2H, br s), 7.96 (1H, d, J=8.4 Hz), 8.07 (1H, s), 12.38 (1H, br s).

Step 4, 5-Amino-N-[(1-butyl-4-piperidinyl)methyl]-2-chloroimidazo[1,2-a]pyridine-8-carboxamide The title compound was prepared according to the procedure described in the step 3 in EXAMPLE 5 using 5-amino-2-chloroimidazo[1,2-a]pyridine-8-carboxylic acid (EXAMPLE 25, Step 3) and 1-(1-butyl-4-piperidinyl)methanamine (EXAMPLE 1, METHOD A, Step 5).

MS (ESI+) m/z: 364 (M+1). m.p.: 113° C. IR (KBr) ν: 3348, 3263, 3150, 2954, 2934, 2872, 2824, 1647, 1562, 1495, 1306, 1256, 1134, 966 cm$^{-1}$. $^1$H-NMR (DMSO-d$_6$) δ: 0.86 (3H, t, J=7.2 Hz), 1.20–1.55 (7H, m), 1.64–1.68 (2H, m), 1.78–1.86 (2H, m), 2.20–2.26 (2H, m), 2.83–2.87 (2H, m), 3.26–3.30 (2H, m), 6.17 (1H, d, J=8.3 Hz), 7.50 (2H, br s), 7.97 (1H, d, J=8.3 Hz), 8.06 (1H, s), 9.31 (1H, br). Anal. Calcd. for C$_{18}$H$_{26}$ClN$_5$O.1.1H$_2$O: C, 56.34; H, 7.41; N, 18.25. Found: C, 56.14; H, 7.71; N, 17.92.

Example 26

5-Amino-6-chloro-N-[(1-isobutylpiperidin-4-yl)methyl]-2-methylimidazo[1,2-a]pyridine-8-carboxamide Step 1, Methyl 2,6-bis[(2,2-dimethylpropanoyl)amino]nicotinate In a 5 L, 4-necked round bottom flask, immersed in ice-cold ethanol-isopropanol (isopropanol 13%, −15° C.) bath, to a solution of 2,6-bis[(2,2-dimethylpropanoyl)amino]pyridine (J. Am. Chem. Soc. 1986, 108, 3310–3318, 126 g, 454 mmol) in anhydrous tetrahydrofuran (1.5 L) was added 2.66 M solution of n-buthyllithium in hexane (598 mL) dropwise from a dropping funnel (1 L) during the period of 6 h under nitrogen atmosphere (internal temperature was maintained at −15° C.~−5° C.). The resulting solution was stirred at 0° C. (internal temperature) for 12 h under nitrogen atmosphere. The formation of yellowish precipitate was noticed. Then the suspension was cooled to −15° C., dimethyl carbonate (194 mL, 2.3 mmol) was added in one portion. The reaction solution was stirred at 0° C. for 1 h, quenched with 1. 5 L of 1 N aqueous hydrochloric acid, pH value was controlled to ~4.5 by adding 1 N aqueous hydrochloric acid, then 600 mL of ethyl acetate was added. After the layers were separated, the organic layer was washed with 1 L of 0.2 N aqueous NaOH (1 L) and brine (500 mL). Each aqueous layer was extracted with ethyl acetate (300 mL) twice. Combined organic layer was dried over sodium sulfate (~300 g) and concentrated. The residue was diluted with diisopropylether (300 mL) and the solution was evaoprated to remove the residual ethyl acetate azeotropically. The residue was dissolved with diisopropylether (360 mL) at 60° C. with gentle stirring, and then the small portion of the crystalline of the desired product (~5 mg) was added as seed. The formation of a pale yellow precipitate was noticed. The resulting suspension was cooled to room temperature (during the period of 2 h), and stirred at room temperature for 2 h. The suspension was filtered through paper filter, then the cake was washed with diisopropylether (80 mL). The solid was dried under reduced pressure at room temperature for 1 day to give the title compound (120 g, 358 mmol, 79%) as a pale yellow solid.

MS (EI) m/z: 335 (M$^+$) $^1$H-NMR (CDCl$_3$) δ: 1.32 (9H, s), 1.35 (9H, s), 3.93 (3H, s), 8.04 (1H, d, J=8.8 Hz), 8.31 (1H, d, J=8.8 Hz), 9.32 (1H, br s), 11.47 (1H, br s).

Step 2, Methyl 5-Chloro-2,6-bis[(2,2-dimethylpropanoyl)amino]nicotinate

To a solution of methyl 2,6-bis[(2,2-dimethylpropanoyl)amino]nicotinate (EXAMPLE 26, Step 1, 186 g, 555 mmol) in anhydrous N,N-dimethylformamide (930 mL) was added a solution of N-chlorosuccinimide (81.5 g, 610 mmol) in anhydrous N,N-dimethylformamide (560 mL) dropwise from a dropping funnel (1 L) during the period of 2.5 h at 70° C. (internal temperature) under nitrogen atmosphere. The resulting pale yellow solution was stirred at 70° C. for 2 h and allowed to cool to room temperature. The reaction solution was quenched with a solution of 250 g of ammonium chloride and 100 g of sodium hydrogen sulfite in 3 L of water and extracted with a mixture of ethyl acetate and hexane (3 L, 3: 1). After the layers were separated, the organic layer was washed with water (2 L), dried over sodium sulfite (300 g) and evaporated. The residual pale yellow solid was added isopropylether (1.4 L) and the resulting mixture was stirred at 60° C. for 2 h. After the mixture was cooled to room temperature, the mixture was filtered through paper filter, and the cake was washed with isopropylether (200 mL), dried under reduced pressure at room temperature to give (153.9 g, 416 mmol) of the title compound as a white solid.

MS (ESI+) m/z: 370 (M+1) $^1$H-NMR (CDCl$_3$) δ: 1.34 (18H, s), 3.94 (3H, s), 8.30 (1H, s), 8.51 (1H, br s), 11.12 (1H, br s).

Step 3, Methyl 2,6-Diamino-5-chloronicotinate

To a colorless solution of methyl 5-chloro-2,6-bis[(2,2-dimethylpropanoyl)amino]nicotinate (EXAMPLE 26, Step 2, 153.9 g, 416 mmol) in methanol (1.5 L) was added a solution of potassium tert-butoxide (185 g, 1.65 mol) in methanol (500 mL) dropwise during the period of 20 min at room temperature under nitrogen atmosphere. Dissolving potassium tert-butoxide in methanol was exothermic, so potassium tert-butoxide must be added portionwise from powder addition funnel to methanol during the period of 2 h with ice-cold water bath. After the addition was completed, the reaction solution was stirred at reflux temperature for 1 h under nitrogen atmosphere, and cooled to room temperature. The resulting suspension was evaporated and ca. 1.3 L of methanol was removed (ca. 700 mL of methanol was remained). To this mixture was added water (1.2 L) and stirred at room temperature for 1 h with water bath (internal temperature was maintained at 20° C.), then the resulting suspension was filtered through paper filter and the pale yellow solid was dried under reduced pressure at 50° C. for 12 h to give 74.3 g (368.9 mmol, 89%) of the title compound as a pale yellow crystal. Rf value: 0.28 (ethyl acetate/hexane=1:2).

$^1$H-NMR (DMSO-d$_6$) δ: 3.71 (3H, s), 6.77 (2H, br s), 6.94 (2H, br s), 7.72 (1H, s).

Step 4, Methyl 5-Amino-6-chloro-2-methylimidazo[1,2-a]pyridine-8-carboxylate

A mixture of methyl 2,6-diamino-5-chloronicotinate (EXAMPLE 26, Step 3, 15 g, 74.4 mmol), bromoacetone (10.4 mL, 112 mmol) and sodium iodide (16.7 g, 112 mmol) in methanol (700 mL) was stirred under reflux for 22 h. Another 2.5 mL (33 mmol) of bromoacetone was added and the stirring was continued for 24 h. The reaction mixture was quenched with saturated aqueous sodium carbonate and removed methanol in vacuo. The residue was extracted with ethyl acetate (250 mL×10) adding a small amount of methanol to dissolve the organic solid. The organic extracts were dried over sodium sulfate and concentrated. Purification by column chromatography on silica gel eluting with dichloromethane/methanol (20:1) gave a dark brown solid, which was washed with ethyl acetate and filtered to afford 10.5 g (43.9 mmol, 59%) of the title compound as a pale brown solid.

MS (FAB) m/z: 240 (M+). $^1$H-NMR (DMSO-d$_6$) δ: 2.34 (3H, s), 3.80 (3H, s), 7.70 (2H, br s), 7.83 (1H, s), 7.85 (1H, s).

Step 5, Methyl 5-Amino-6-chloro-2-methylimidazo[1,2-a]pyridine-8-carboxylic Acid A mixture of methyl 5-Amino-6-chloro-2-methylimidazo[1,2-a]pyridine-8-carboxylate (EXAMPLE 26, Step 4, 10.5 g, 43.9 mmol,) and 1 N lithium hydroxide (87.7 mL, 87.7 mmol) in methanol (100 mL) was stirred under reflux for 1 h. After removal of the solvent in vacuo, the residue was suspended with water and treated with 2 N hydrochloric acid to adjust to pH 4. The resulting solid was filtered, washed with water and diethyl ether and dried in vacuo with heating to give 9.5 g (42.2 mmol, 96%) of the title compound as a brown solid.

MS (EI) m/z: 225 (M+). $^1$H-NMR (DMSO-d$_6$) δ: 2.38 (3H, s), 7.88 (1H, s), 7.92 (1H, s), 8.00 (2H, br s). A signal due to COOH was not observed.

Step 6, 5-Amino-6-chloro-N-[(1 -isobutylpiperidin-4-yl)methyl]-2-methylimidazo[1,2-a]pyridine-8-carboxamide To a suspension of 5-amino-6-chloro-2-methylimidazo[1,2-a]pyridine-8-carboxylic acid (EXAMPLE 26, Step 5, 7.0 g, 31.0 mmol) in N,N-dimethylformamide (140 mL) was added 1,1'-carbonyldiimidazole (6.0 g, 37.2 mmol) at room temperature. After stirring for 5 min, the temperature was raised to 60° C. and the stirring was continued for 2.5 h. Another 2.5 g (15.5 mmol) of 1,1'-carbonyldiimidazole was added at room temperature and the mixture was stirred at the temperature for 40 min and at 60° C. for 2 h. Then a N,N-dimethylformamide (25 mL) solution of (1-isobutylpiperidin-4-yl)methylamine (Bioorg. Med. Chem. 1999, 7, 2271–2281, 6.3 g, 37.2 mmol) was added at room temperature and the stirring was continued for 18 h. The mixture was quenched with water (165 mL). The resulting precipitate was collected by filtration and washed with water (200 mL). The filtrate was extracted with ethyl acetate (150 mL×2). The precipitate and the organic extracts were combined and concentrated. The residue was purified by column chromatography (basic silica gel) eluting with ethyl acetate/hexane (1:1 to 2:1) to give a pale yellow solid (8.39 g), which was washed with diethyl ether (200 mL) to give 7.3 g (19.4 mmol, 63%) of the title compound as a white solid.

MS (EI) m/z: 377(M+). m.p.: 216–219° C. IR (KBr) ν: 3472, 3246, 2951, 2920, 1638, 1607, 1562, 1545, 1437, 1321, 1265, 1148, 1101, 710 cm$^{-1}$. $^1$H-NMR (DMSO-d$_6$) δ: 0.82 (6H, d, J=6.6 Hz), 1.18–1.31 (2H, m), 1.41–1.55 (1H, m), 1.61–1.83 (5H, m), 1.97 (2H, d, J=7.2 Hz), 2.37 (3H, s), 2.78–2.81 (2H, m), 3.28 (2H, t, J=6.0 Hz), 7.58 (2H, br s), 7.86 (1H, s), 7.88 (1H, s), 9.92 (1H, br). Anal. Calcd. for $C_{19}H_{28}ClN_5O$: C, 60.39; H, 7.47; N, 18.53. Found: C, 60.33; H, 7.68; N, 18.43.

Example 27

5-Amino-N-[(1-isobutylpiperidi-4-yl)methyl]-2-methylimidazo[1,2-a]pyridine-8-carboxamide Step 1, 5-Amino-N-[(1-isobutylpiperidin-4-yl)methyl]-2-methylimidazo[1,2-a]pyridine-8-carboxamide A mixture of 5-amino-6-chloro-N-[(1-isobutylpiperidin-4-yl)methyl]-2-methylimidazo[1,2-a]pyridine-8-carboxamide (EXAMPLE 26, Step 6, 134 mg, 0.36 mmol), 10% palladium charcoal (67 mg) and ammonium formate (224 mg, 3.6 mmol) in methanol (5 mL) was stirred at room temperature for 4 h. The mixture was filtered through a pad of Celite and the filtrate was concentrated. The residue was treated with 25% aqueous ammonia (10 mL), extracted with dichloromethane (20 mL×2) and washed with brine (20 mL). Removal of the solvent gave 92.4 mg (0.37 mmol, 76%) of the title compound as a yellow amorphous.

MS (EI) m/z: 343(M+). IR (KBr) ν: 3327, 3180, 2953, 2924, 1638, 1558, 1516, 1431, 1290 cm$^{-1}$. $^1$H-NMR (DMSO-d$_6$) δ: 0.83 (6H, d, J=6.5 Hz), 1.17–1.32 (2H, m), 1.40–1.54 (1H, m), 1.61–1.85 (5H, m), 1.99 (2H, d, J=7.3 Hz), 2.36 (3H, s), 2.79–2.83 (2H, m), 3.25–3.29 (2H, m), 6.04 (1H, d, J=8.1 Hz), 7.26 (2H, br s), 7.68 (1H, s), 785 (1H, d, J=8.1 Hz), 10.00 (1H, br). Anal. Calcd. for $C_{19}H_{29}N_5O \cdot 0.05C_4H_8O \cdot 0.5H_2O$: C, 64.62; H, 8.59; N, 19.62. Found: C, 64.89; H, 8.64; N, 19.36.

Example 28

5-Amino-6-chloro-N-{[1-(3,3-dimethylbutyl) piperidin-4-yl]methyl}-2-ethylimidazo[1,2-a] pyridine-8-carboxamide Step1. Methyl 5-Amino-6-chloro-2-ethylimidazo[1,2-a] pyridine-8-carboxylate The title compound was prepared according to the procedure described in the step 4 in EXAMPLE 26 from methyl 2,6-diamino-5-chloro-3-pyridinecarboxylate (EXAMPLE 26, Step 3) and 1-bromo-2-butanone.

MS (EI) m/z: 253 (M$^+$). $^1$H-NMR (DMSO-d$_6$) δ: 1.27 (3H, t, J=7.5 Hz), 2.72 (2H, q, J=7.5 Hz), 3.80 (3H, s), 7.72 (2H, s), 7.86 (1H, s), 7.87 (1H, s).

Step 2. 5-Amino-6-chloro-2-ethylimidazo[1,2-a]pyridine-8-carboxylic Acid

The title compound was prepared, according to the procedure described in the step 5 in EXAMPLE 26, from methyl 5-amino-6-chloro-2-ethylimidazo[1,2-a]pyridine-8-carboxylate (EXAMPLE 28, Step 1).

MS (EI) m/z: 239 (M$^+$). $^1$H-NMR (DMSO-d$_6$) 8:1.27 (3H, t, J=7.2 Hz), 2.74 (2H, q, J=7.2 Hz), 7.88 (1H, s), 7.95 (1H, s). A signal due to COOH was not observed.

Step 3. tert-Butyl 4-({[(5-Amino-6-chloro-2-ethylimidazo[1,2-a]pyridin-8-yl)carbonyl]amino}methyl) piperidine-1-carboxylate A mixture of 5-amino-6-chloro-2-ethylimidazo[1,2-a] pyridine-8-carboxylic acid (EXAMPLE 28, Step 2, 10.00 g, 41.72 mmol), tert-butyl 4-(aminomethyl)piperidine-1-carboxylate (J. Prugh, L. A. Birchenough and M. S. Egbertson, *Synth. Commun.*, 1992, 22, 2357–60, 15.20 g, 70.93 mmol), DEPC (10.76 mL, 70.93 mmol) and diisopropylethylamine (18.17 mL, 104.4 mmol) in N,N-dimethylformamide (267 mL) was stirred at room temperature for 43 h. The solvent was removed by evaporation. The residue was basified with aqueous sodium bicarbonate (40 mL), and extracted with dichloromethane (5×100 mL). The combined extract was washed with brine, dried over magnesium sulfate, and concentrated in vacuo. Flash chromatography of the residue eluting with dichloromethane/ methanol (100:1 to 20:1) afforded 19.08 g (90%) of the title compound as a yellow oil.

$^1$H-NMR (CDCl$_3$) δ: 1.35 (3H, t, J=7.6 Hz), 1.45 (9H, s), 1.88–1.28 (5H, m), 2.88–2.64 (2H, m), 3.52–3.38 (2H, m), 4.30–3.97 (4H, m), 5.17 (2H, br s), 7.21 (1H, s), 8.19 (1H, s), 10.21 (1H, bv).

Step 4. 5-Amino-6-chloro-2-ethyl-N-(piperidin-4-ylmethyl)imidazo[1,2-a]pyridine-8-carboxamide To a stirred solution of tert-butyl 4-({[(5-amino-6-chloro-2-ethylimidazo[1,2-a]-pyridin-8-yl)carbonyl] amino}methyl)piperidine-1-carboxylate (EXAMPLE 28, Step 3, 13.71 g, 31.44 mmol) in 10% hydrochloric acid methanol solution (314 mL) was added concentrated hydrochloric acid (10 mL). After stirring at room temperature for 26 h, the mixture was concentrated to about 50 mL in vacuo. The residue was basified with an excess of sodium carbonate and then insoluble material was filtered off. The filtrate was concentrated azeotropically with ethanol and diluted with a mixture of dichloromethane and methanol (5:1, 200 mL). The formed inorganic solid was filtered off again. The filtrate was concentrated in vacuo to give a pale yellow amorphous, which was crystallized from ethanol to afford 4.79 g (45%) of the title compound as an off-white solid. Furthermore, 5.09 g (48%) of the compound was obtained from the mother liquid.

MS (ESI) m/z: 336.17 (M+H)$^+$, 334.14 (M–H)$^-$. m.p. (TG/DTA): 153° C. IR (KBr) ν: 3387, 3300, 3188, 2964, 1639, 1605, 1562, 1514 cm$^{-1}$. $^1$H-NMR (DMSO-d$_6$) δ: 1.30–0.90 (2H, m), 1.30 (3H, t, J=7.6 Hz), 1.74–1.50 (3H, m), 2.55–2.36 (2H, m), 2.75 (2H, q, J=7.6 Hz), 3.04–2.86 (2H, m), 3.27 (2H, t, J=5.9 Hz), 7.86 (1H, s), 7.94 (1H, s), 10.05–9.94 (1H, m). Anal. Calcd. for $C_{16}H_{22}ClN_5O \cdot 2.5H_2O \cdot 0.8EtOH$: C, 50.70; H, 7.49; N, 16.80. Found: C, 50.57; H, 7.27; N, 16.80.

Step 5. 5-Amino-6-chloro-N-{l1-(3,3-dimethylbutyl) piperidin-4-yl]methyl}-2-ethylimidazo[1,2-a]pyridine-8-carboxamide To a stirred mixture of 5-amino-6-chloro-2-ethyl-N-(piperidin-4-ylmethyl)imidazo [1,2-a]pyridine-8-carboxamide (EXAMPLE 28, Step 4, 450 mg, 1.34 mmol) and 1-bromo-3,3-dimethylbutane (606 mg, 3.35 mmol) in N,N-dimethylformamide (6 mL) were added potassium carbonate (648 mg, 4.69 mmol) and sodium iodide (502 mg, 3.35 mmol). After stirring at 90° C. for 42 h, the reaction mixture was cooled and evaporated. The residue was diluted with dichloromethane (30 mL) and water (20 mL). The water phase was extracted with dichloromethane (2×30 mL). The combined extract was washed with brine, dried over magnesium sulfate, and concentrated. Flash chromatography (NH-silica gel) of the residue eluting with hexane/ethyl acetate (1:1 to 1:2) afforded a brown solid (296 mg), which was recrystallized from ethyl acetate to give 191 mg (34%) of the title compound as a pale brown solid.

MS (ESI) m/z: 420 (M+H)$^+$, 418 (M–H)$^-$. m.p. (TG/DTA): 234° C. IR (KBr) ν: 3136, 2947, 1636, 1607, 1558 cm$^{-1}$. $^1$H-NMR (CDCl$_3$) δ: 0.89 (9H, s), 1.36 (3H, t, J=7.5 Hz), 1.98–1.36 (9H, m), 2.37–2.26 (2H, m), 2.83 (2H, q, J=7.5 Hz), 3.02–2.92 (2H, m), 3.45 (2H, t, J=6.2 Hz), 4.96 (2H, bsv), 7.12 (1H, s), 8.20 (1H, s), 10.17 (1H, bs). Anal. Calcd. for $C_{22}H_{34}ClN_5O$: C, 62.91; H, 8.16; N, 16.68. Found: C, 62.71; H, 8.20; N, 16.62.

Example 29

5-Amino-6-chloro-2-ethyl-N-{[1-(2-methoxy-2-methylpropyl)piperidin-4-yl]methyl}imidazo[1,2-a] pyridine-8-carboxamide Step 1. tert-Butyl 4-[(Dibenzylamino)carbonyl] piperidine-1-carboxylate To a stirred mixture of 1-(tert-butoxycarbonyl)piperidine-4-carboxylic acid (*J. Med. Chem.* 1998, 41, 2492–2502, 3.0 g, 13.1 mmol), dibenzylamine (2.5 mL, 13.1 mmol) and diisopropylethylamine (3.4 mL, 19.7 mmol) in dichloromethane (150 mL) was added Pybrop (bromo-tris-pyrrolidinophosophonium hexafluorophosphate) (6.1 g, 15.7 mmol) was added at 0° C. The mixture was stirred at ambient temperature for 18 h and partitioned between dichloromethane and water. After extraction with dichloromethane, the combined organic phase was dried over magnesium sulfate and concentrated. The residue was purified by flash column chromatography on silica gel eluting with hexane/ethyl acetate (6:1) to afford 4.0 g (75%) of the title compound as a colorless amorphous.

$^1$H-NMR (CDCl$_3$) δ: 1.43 (9H, s), 1.50–1.74 (4H, m), 1.78–1.95 (2H, m), 2.58–2.75 (2H, m), 4.45–4.51 (1H, m), 7.11–7.44 (10H, m).

Step 2. N,N-Dibenzylpiperidine-4-carboxamide

To a stirred solution of tert-butyl 4-[(dibenzylamino) carbonyl]piperidine-1-carboxylate (EXAMPLE 29, Step 1, 4.0 g, 10.0 mmol) in methanol (550 mL) was added 4N HCl dioxane solution (80 mL, 320 mmol) at 0° C. The mixture was stirred for 6 h and evaporated. The resulting amorphous was dissolved in aqueous ammonia and the mixture was extracted with dichloromethane. The combined extract was dried over magnesium sulfate, and concentrated to afford 3.0 g (99%) of the title compound as a colorless amorphous.

MS (ESI) m/z: 309 (M+H)$^+$, 307 (M−H)$^-$.

Step 3. N,N-Dibenzyl-N-(piperidin-4-ylmethyl)amine

To a suspension of lithium aluminum hydride (min.80%, 1.50 g, 40.0 mmol) in tetrahydrofuran (50 ml) was added dropwise a solution of N,N-dibenzylpiperidine-4-carboxamide (EXAMPLE 29, Step 2, 3.08 g, 10.0 mmol) in tetrahydrofuran (50 ml) at 0° C. over 15 min. The mixture was stirred at 0° C. for 30 min and at 40° C. for 4 h. After cooling to 0° C., water (3.3 ml), 15% NaOH aqueous solution (3.3 ml), and then water (10 ml) were carefully added dropwise. The resulting mixture was filtered through a pad of Celite and the filtrate was concentrated in vacuo to give 2.85 g (97%) of the title compound as a pale yellow oil.

MS (ESI) m/z: 295 (M+H)$^+$, 293 (M−H)$^-$. $^1$H-NMR (CDCl$_3$) δ: 0.90–1.10 (2H, m), 1.70–1.92 (4H, m), 2.20 (2H, d, J=7.2 Hz), 2.78 (1H, s), 2.86 (2H, d, J=1.5 Hz), 3.48 (4H, s), 7.16–7.35 (10H, m).

Step 4. 1-{4-[(Dibenzylamino)methyl]piperidin-1-yl}-2-methylpropan-2-ol

A mixture of N,N-dibenzyl-N-(piperidin-4-ylmethyl) amine (EXAMPLE 29, Step 3, 3.3 g, 11.21 mmol) and 2,2-dimethyloxirane (12.1 mL, 134.5 mmol) in methanol (40 mL) and tetrahydrofuran (5 mL) was heated at 40° C. with stirring for 17 h. The volatile components were removed and the residue was purified by flash column chromatography on amine gel eluting with hexane/ethyl acetate (50:1) to afford 3.0 g (73%) of the title compound as a colorless amorphous MS (ESI) m/z: 367 (M+H)$^+$.

Step 5. N,N-Dibenzyl-N-{[1-(2-methoxy-2-methylpropyl)piperidin-4-yl]methyl}amine To a suspension of sodium hydride (abt. 60% in mineral oil, 342 mg, 8.6 mmol) in a mixture of tetrahydrofuran (20 mL) and N,N-dimethylformamide (10 mL) was added a solution of 1-{4-[(dibenzylamino)methyl]piperidin-1-yl}-2-methylpropan-2-ol (EXAMPLE 29, Step 4, 3.0 g, 8.2 mmol) in tetrahydrofuran (20 ml) at 0° C. The mixture was stirred at ambient temperature for 3 days. The mixture was partitioned between ethyl acetate and water. After extraction with ethyl acetate, the combined organic phase was dried over magnesium sulfate, and concentrated. The residue was purified by flash column chromatography on amine gel eluting with hexane/ethyl acetate (100:1) to afford 0.76 g (24%) of the title compound as colorless amorphous.

MS (ESI) m/z: 381 (M+H)$^+$. $^1$H-NMR (CDCl$_3$) δ: 1.12 (6H, s), 0.99–1.19 (2H, m), 1.43–1.60 (1H, m), 1.69–1.74 (2H, m), 2.01–2.11 (2H, m), 2.11–2.26 (4H, m), 2.84–2.91 (2H, m), 3.18 (3H, s), 3.50 (3H, s), 7.18–7.37 (10H, m).

Step 6. [1-(2-Methoxy-2-methylpropyl)piperidin-4-yl]methylamine

To a solution of N,N-dibenzyl-N-{[1-(2-methoxy-2-methylpropyl)piperidin-4-yl]methyl}amine (EXAMPLE 29, Step 5, 756 mg, 1.85 mmol) and ammonium formate (583 mg, 9.24 mmol) in methanol (40 mL) and water (15 mL) was added 10% palladium on carbon (185 mg) at ambient temperature. The mixture was heated at 80° C. for 6 h. After cooling, the mixture was filtered through a pad of Celite and the filtrate was concentrated in vacuo. The obtained residue was partitioned between dichloromethane and aqueous ammonia. After extraction with dichloromethane, the combined organic phase was dried over magnesium sulfate and concentrated to give 275 mg (66%) of the title compound as a pale yellow oil. $^1$H-NMR (CDCl$_3$) δ: 1.15 (6H, s), 1.17–1.26 (2H, m), 1.58–1.68 (1H, m), 2.05–2.19(2H, m), 2.28 (2H, s), 2.53–2.56 (2H, m), 2.90–2.98 (2H, m), 3.20 (3H, s).

Step 7, 5-Amino-6chloro-2-ethyl-N-{[1-(2-methoxy-2-methylpropyl)piperidin-4-yl]methyl}imidazo[1,2-a] pyridine-8-carboxamide The title compound was prepared, according to the procedure described in the step 2 in EXAMPLE 28, using 5-amino-6-chloro-2-ethylimidazo[1, 2-a]pyridine-8-carboxylic acid (EXAMPLE 28, Step 2) and [1-(2-methoxy-2-methylpropyl)piperidin-4-yl]methylamine (EXAMPLE 29, Step 6).

MS (ESI) m/z: 422 (M+H)$^+$, 420(M−H)$^-$. m.p.: 211° C. IR (KBr) ν: 3466, 3250, 2955, 2930, 2918, 1632, 1620, 1600, 1545, 1437, 1319, 1268, 1146, 1105, 998 cm$^{-1}$. $^1$H-NMR (CDCl$_3$) δ: 1.16 (6H, s), 1.35 (3H, t, J=7.5 Hz), 1.71–1.76 (2H, m), 2.29(2H, s), 2.82 (2H, q, J=7.5 Hz), 2.46 (3H, s), 2.93–2.97 (2H, m), 3.43 (2H, t, J=6.4 Hz), 4.97 (2H, brs), 7.14 (1H, s), 8.19 (1H, s), 10.08 (1H, br). Anal. Calcd. for C$_{21}$H$_{32}$ClN$_5$O.0.5H$_2$0: C, 59.14; H, 7.68; N, 16.42. Found: C, 59.03; H, 7.62; N, 16.24.

Example 30

5-Amino-6-chloro-2-methyl-N-{[1-(2-methoxy-2-methylpropyl)piperidin-4-yl]methyl}imidazo[1,2-A] pyridine-8-carboxamide Step 1, 5-Amino-6-chloro-2-methyl-N-{l1-(2-methoxy-2-methylpropyl)piperidin-4-yl]methyl}imidazo[1,2-a] pyridine-8-carboxamide The title compound was prepared according to the procedure described in the step 2 in EXAMPLE 28 from 5-amino-6-chloro-2-methylimidazo[1,2-a]pyridine-8-carboxylic acid (EXAMPLE 26, Step 5) and [1-(2-methoxy-2-methylpropyl)piperidin-4-yl]methylamine (EXAMPLE 29, Step 6).

MS (ESI) m/z: 408 (M+H)$^+$, 406 (M−H)$^-$. m.p.: 211° C. IR (KBr) ν: 3470, 3342, 3208, 2940, 2918, 1655, 1601, 1555, 1545, 1437, 1319, 1288, 1266, 1147 cm$^{-1}$. $^1$H-NMR (CDCl$_3$) δ: 1.16 (6H, s), 1.39–1.47 (2H, m), 1.71–1.76 (2H, m), 2.16 (2H, t, J=11.0 Hz), 2.29 (2H, s), 2.46 (3H, s), 2.93–2.97 (2H, m), 3.20 (3H, s), 3,43 (2H, t, J=6.4 Hz), 4.97 (2H, br s), 7.14 (1H, s), 8.19 (1H, s), 10.08 (1H, br s). Anal. Calcd. for C$_{21}$H$_{32}$ClN$_5$O$_2$: C, 58.89; H, 7.41; N, 17.17. Found: C, 58.62; H, 7.38; N, 16.93.

What is claimed is:

1. A compound of the formula (I):

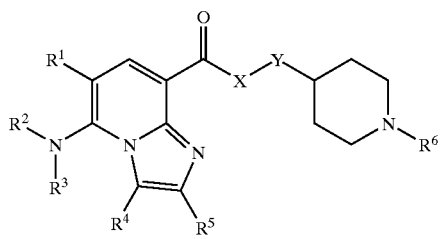

or the pharmaceutically acceptable salts thereof wherein
$R^1$ is hydrogen, halo or $C_{1-6}$ alkyl;
$R^2$ and $R^3$ are independently hydrogen, $C_{1-6}$ alkyl, $C_{2-6}$ alkenyl, $C_{2-6}$ alkynyl, mono- or di-($C_{1-5}$)alkyl amino, amino($C_{1-5}$)alkyl or hydroxy($C_{1-5}$)alkyl; or $R^2$ and $R^3$ taken together with the nitrogen atom to which they are attached may form substituted or non-substituted nitrogen-containing hetrocyclic;
$R^4$ is hydrogen, halo, $C_{1-8}$ acyl, amino, amido, substituted or non-substituted aryl, substituted or non-substituted aryl($C_{1-6}$)alkyl, or substituted or non-substituted heterocyclic;
$R^5$ is hydrogen, halo, $C_{1-6}$ alkyl, $C_{2-6}$ alkenyl, $C_{2-6}$ alkynyl, $C_{1-8}$ acyl, amino, amido, substituted or non-substituted aryl, substituted or non-substituted aryl($C_{1-6}$)alkyl, or substituted or non-substituted heterocyclic;
$R^6$ is hydrogen, $C_{1-6}$ alkyl or $C_{1-6}$ alkoxy ($C_{1-6}$)alkyl;
X is $NR^9$ wherein $R^9$ is hydrogen or $C_{1-6}$ alkyl; and
Y is $(CR^7R^8)_n$ wherein $R^7$ and $R^8$ are independently hydrogen or $C_{1-6}$ alkyl, and n is an integer from 0 to 5.

2. A compound according to claim 1, wherein
$R^1$ is hydrogen, halo or $C_{1-3}$ alkyl;
$R^2$ and $R^3$ are independently hydrogen, $C_{1-3}$ alkyl, mono- or di-($C_{1-5}$)alkyl amino, amino($C_{1-5}$)alkyl or hydroxy ($C_{1-5}$)alkyl; or $R^2$ and $R^3$ taken together with the nitrogen atom to which they are attached may form substituted or non-substituted nitrogen-containing hetrocyclic;
$R^4$ is hydrogen, halo, $C_{1-3}$ acyl, substituted or non-substituted aryl, substituted or non-substituted aryl($C_{1-3}$)alkyl, or substituted or non-substituted heterocyclic;
$R^5$ is hydrogen, halo, $C_{1-3}$ alkyl, $C_{1-3}$ acyl, amido, substituted or non-substituted aryl, substituted or non-substituted aryl($C_{1-3}$)alkyl, or substituted or non-substituted heterocyclic;
$R^6$ is hydrogen, $C_{1-5}$ alkyl or $C_{1-3}$ alkoxy ($C_{15}$)alkyl;
X is $NR^9$; and Y is $(CR^7R^7)_n$, wherein $R^7$, $R^8$ and $R^9$ are independently hydrogen or $C_{1-3}$ alkyl, and n is an integer from 0 to 3.

3. A compound according to claim 1, wherein
$R^1$ is hydrogen or halo;
$R^2$ and $R^3$ are independently hydrogen or $C_{1-3}$ alkyl; or $R^2$ and $R^3$ taken together with the nitrogen atom to which they are attached may form hetrocyclic selected from morpholino, piperazino, piperidino, pyrrolidino, azetidino, pyrazolidino, (1,2,3,4)-tetrahydroisoqunolino and perhydroisoquinolino, which may be optionally substituted with halo, $C_{1-3}$ alkyl, $C_{1-3}$ alkoxy, mono- or di-($C_{1-3}$)alkyl amino or $C_{1-3}$ alkoxy($C_{1-3}$) alkyl;

$R^4$ is hydrogen, halo, $C_{1-3}$ acyl, aryl selected from phenyl and naphthyl, arylalkyl selected from phenyl $C_{1-3}$ alkyl and naphthyl $C_{1-3}$ alkyl, or heteroaryl selected from piperidino, morpholino, thiamorpholino, pyrrolidino, pyrazolino, pyrazolidino, pyrazoryl, piperazinyl, furyl, thienyl, oxazolyl, tetrazolyl, thiazolyl, imidazolyl, imidazolinyl, pyrazolyl, pyridyl, pyrimidinyl, pyrrolyl, pyrrolidinyl and quinolyl, wherein said aryl, arylalkyl or heteroaryl may optionally be substituted with halo, $C_{1-3}$ alkyl, $C_{1-3}$ alkoxy, mono- or di-($C_{1-3}$)alkyl amino or $C_{1-3}$ alkoxy($C_{1-3}$) alkyl;
$R^5$ is hydrogen, halo, $C_{1-3}$ alkyl, $C_{1-3}$ acyl, amido, aryl selected from phenyl and naphthyl, arylalkyl selected from phenyl $C_{1-3}$ alkyl and naphthyl $C_{1-3}$ alkyl, or heteroaryl selected from piperidino, morpholino, thiamorpholino, pyrrolidino, pyrazolino, pyrazolidino, pyrazoryl, piperazinyl, furyl, thienyl, oxazolyl, tetrazolyl, thiazolyl, imidazolyl, imidazolinyl, pyrazolyl, pyridyl, pyrimidinyl, pyrrolyl, pyrrolidinyl and quinolyl, wherein said aryl, arylalkyl or heteroaryl may optionally be substituted with halo, $C_{1-3}$ alkyl, $C_{1-3}$ alkoxy, mono- or di-($C_{1-3}$)alkyl amino or $C_{1-3}$ alkoxy($C_{1-3}$) alkyl;
$R^6$ is $C_{1-5}$ alkyl or $C_{1-3}$ alkoxy ($C_{1-5}$)alkyl;
X is $NR^9$; and Y is $(CR^7R^8)_n$, wherein $R^7$, $R^8$ and $R^9$ are independently hydrogen or methyl, and n is an integer from 0 to 2.

4. A compound according to claim 1, wherein
$R^1$ is halo;
$R^2$ and $R^3$ are independently hydrogen or $C_{1-3}$ alkyl; or $R^2$ and $R^3$ taken together with the nitrogen to which they are attached may form hetrocyclic selected from morpholino, piperazino and piperidino;
$R^4$ is hydrogen, halo, $C_{1-3}$ acyl, phenyl, naphthyl, benzyl, piperidino, morpholino, pyrrolidino, pyrazolino, pyrazoryl, piperazinyl, furyl, thienyl, oxazolyl, tetrazolyl, thiazolyl, imidazolyl, pyridyl, pyrimidinyl or pyrrolyl;
$R^5$ is hydrogen, halo, $C_{1-3}$ alkyl, $C_{1-3}$ acyl, amido, phenyl, naphthyl, benzyl, piperidino, morpholino, pyrrolidino, pyrazolino, pyrazoryl, piperazinyl, furyl, thienyl, oxazolyl, tetrazolyl, thiazolyl, imidazolyl, pyridyl, pyrimidinyl or pyrrolyl;
$R^6$ is $C_{1-4}$ alkyl or $C_{1-3}$ alkoxy ($C_{1-4}$)alkyl;
X is NH; and
Y is chemical bond or methylene.

5. A compound according to claim 1, wherein
$R^1$ is chloro;
$R^2$ and $R^3$ are independently hydrogen or $C_{1-3}$ alkyl;
$R^4$ is hydrogen or halo;
$R^5$ is hydrogen, halo or $C_{1-3}$ alkyl;
$R^6$ is $C_{3-4}$ alkyl or methoxy ($C_{1-4}$)alkyl;
X is NH; and
Y is methylene.

6. A compound according to claim 1 selected from
5-amino-N-[(1-butyl-4-piperidinyl)methyl]-6-chloroimidazo[1,2-a]pyridine-8-carboxamide;
5-amino-N-[(1-butyl-4-piperidinyl)methyl]imidazo[1,2-a]pyridine-8-carboxamide;
5-amino-6-chloro-N-[(1-(3-methoxypropyl)-4-piperidinyl]imidazo[1,2-a]pyridine-8-carboxamide;
5-amino-N-[(1-(3-methoxypropyl)-4-piperidinyl]imidazo[1,2-a]pyridine-8-carboxamide;

5-amino-N-[(1-butyl-4-piperidinyl)methyl]-6-chloro-2-methylimidazo[1,2-a]pyridine-8-carboxamide;

5-amino-6-chloro-2-methyl-N-{1-[3-(methyloxy)propyl]-4-piperidinyl}imidazo[1,2-a]pyridine-8-carboxamide;

5-amino-6-chloro-2-methyl-N-({1-[3-(methyloxy)propyl]-4-piperidinyl}methyl)imidazolo[1,2-a]pyridine-8-carboxyamide; and salts thereof.

7. A compound according to claim 6 selected from 5-amino-N-[(1-butyl-4-piperidinyl)methyl]-6-chloroimidazo[1,2-a]pyridine-8-carboxamide;

5-amino-6-chloro-N-[(1-(3-methoxypropyl)-4-piperidinyl]imidazo[1,2-a]pyridine-8-carboxamide; and salts thereof.

8. A pharmaceutical composition for the treatment of disease conditions mediated by 5-$HT_4$ receptor activity, in a mammalian subject, which comprises a therapeutically effective amount of a compound of claim 1 and a pharmaceutically acceptable carrier.

9. A pharmaceutical composition for the treatment of gastroesophageal reflux disease, gastrointestinal disease, gastric motility disorder, upper gut motility disorder, non-ulcer dyspepsia, Functional dyspepsia, irritable bowel syndrome, constipation, dyspepsia, esophagitis, gastroesophageal disease, nausea, central nervous system disease, alzheimers disease, cognitive disorder, emesis, migraine, neurological disease, pain, ischaemic stroke, anxiety or cardiovascular disorder, which comprises a therapeutically effective amount of a compound of claim 1 and a pharmaceutically acceptable carrier.

10. A method for the treatment of disease conditions mediated by 5-$HT_4$ receptor activity, in a mammalian subject, which comprises administering to said subject a therapeutically effective amount of a compound according to claim 1.

11. A method for the treatment of gastroesophageal reflux disease, gastrointestinal disease, gastric motility disorder, upper gut motility disorder, non-ulcer dyspepsia, Functional dyspepsia, irritable bowel syndrome, constipation, dyspepsia, esophagitis, gastroesophageal disease, nausea, central nervous system disease, alzheimers disease, cognitive disorder, emesis, migraine, neurological disease, pain, ischaemic stroke, anxiety or cardiovascular disorder, which comprises administering to said subject a therapeutically effective amount of a compound according to claim 1.

* * * * *